United States Patent
Yano et al.

(10) Patent No.: US 7,615,233 B2
(45) Date of Patent: *Nov. 10, 2009

(54) PARTICULATE CONSTRUCT COMPRISING POLYHYDROXYALKANOATE AND METHOD FOR PRODUCING IT

(75) Inventors: Tetsuya Yano, Kanagawa (JP); Tsuyoshi Nomoto, Tokyo (JP); Shinya Kozaki, Tokyo (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 684 days.

This patent is subject to a terminal disclaimer.

(21) Appl. No.: 10/191,563

(22) Filed: Jul. 10, 2002

(65) Prior Publication Data

US 2003/0194443 A1 Oct. 16, 2003

(30) Foreign Application Priority Data

| Jul. 10, 2001 | (JP) | 2001-210040 |
| Jul. 10, 2001 | (JP) | 2001-210041 |
| Jul. 10, 2001 | (JP) | 2001-210043 |
| Jul. 10, 2001 | (JP) | 2001-210055 |

(51) Int. Cl.
 *A01N 25/34* (2006.01)
(52) U.S. Cl. ..................... 424/408; 435/142
(58) Field of Classification Search ............ 435/41, 435/131, 135, 155, 142; 424/408, 463, 489, 424/490
See application file for complete search history.

(56) References Cited

U.S. PATENT DOCUMENTS

| 4,690,682 | A | * | 9/1987 | Lim ........................... 424/497 |
| 5,064,655 | A | | 11/1991 | Uster et al. ................ 424/450 |
| 5,169,636 | A | | 12/1992 | Nanba et al. ............... 424/450 |
| 5,393,530 | A | | 2/1995 | Schneider et al. .......... 424/450 |
| 5,863,789 | A | | 1/1999 | Komatsu et al. ............ 435/262 |
| 6,146,665 | A | | 11/2000 | Marchessault et al. ...... 424/497 |
| 6,872,564 | B1 | | 3/2005 | Doi et al. .................. 435/252.3 |
| 7,153,622 | B2 | * | 12/2006 | Honma et al. ............... 430/105 |
| 7,186,459 | B2 | * | 3/2007 | Nomoto et al. ............. 428/403 |
| 2003/0145518 | A1 | * | 8/2003 | Noda et al. ............. 47/58.1 SE |

FOREIGN PATENT DOCUMENTS

| EP | 0 172 422 | 2/1986 |
| EP | 0 535 534 | 4/1993 |
| EP | 0 586238 A2 | 3/1994 |
| EP | O 765660 A2 | 4/1997 |
| EP | 1 253 160 | 10/2002 |
| EP | 1 253 476 | 10/2002 |
| JP | 57-118512 | 7/1982 |
| JP | 60-100516 | 6/1985 |
| JP | 61-43119 | 3/1986 |
| JP | 61-63613 | 4/1986 |
| JP | 62-201816 | 9/1987 |
| JP | 1-163135 | 6/1989 |
| JP | 1-57087 | 12/1989 |
| JP | 2-124814 | 5/1990 |
| JP | 2-503315 | 10/1990 |
| JP | 3-94774 | 4/1991 |
| JP | 4-321622 | 11/1992 |
| JP | 5-7492 | 1/1993 |
| JP | 5-93049 | 4/1993 |
| JP | 5-294839 | 11/1993 |
| JP | 6-15604 | 3/1994 |
| JP | 7-14352 | 2/1995 |
| JP | 7-265065 | 10/1995 |
| JP | 8-19227 | 2/1996 |
| JP | 8-151321 | 6/1996 |
| JP | 8-151322 | 6/1996 |
| JP | 8-217691 | 8/1996 |
| JP | 9-191893 | 7/1997 |
| JP | 11-199514 | 7/1999 |
| JP | 2989175 | 12/1999 |
| JP | 2001-69968 | 3/2001 |
| JP | 2001-78753 | 3/2001 |
| JP | 2001-178484 | 7/2001 |
| WO | WO 94/10982 | 11/1993 |
| WO | 96/15815 | 5/1996 |
| WO | 01/11014 | 2/2001 |

OTHER PUBLICATIONS

"Preparation and properties of a novel class of polyhydroxyalkanoate copolymer," Biomacromolecules (2005) 6: 580-586.*

Lee et al. Effect of side chains on thermal degradation of poly(3-hydroxyalkanoates). Macromol. Che. Phys. (2001; published on the Web on Apr. 26, 2001) 202(7): 1257-1261.*

Y. B. Kim, et al., "Preparation and Characterization of Poly(β-hydroxyalkanoates) Obtained from *Pseudomonas oleovorans* Grown with Mixtures of 5-Phenylvaleric Acid and n-Alkanoic Acids", Macromolecules, vol. 24, pp. 5256-5260 (1991).

(Continued)

*Primary Examiner*—Sandra Saucier
*Assistant Examiner*—Susan Hanley
(74) *Attorney, Agent, or Firm*—Fitzpatrick, Cella, Harper & Scinto

(57) ABSTRACT

The invention provides a particulate construct comprising a polyhydroxyalkanoate to serve as microcapsules containing a drug, and serving a slow releasing preparation not associated with a practically unacceptable initial burst release but showing a practically acceptable zero-order release for a certain period and a producing method for such particulate construct, and a slow releasing preparation of a high drug content capable of stably incorporating the drug in the particulate construct such as microcapsules, and a producing method for such preparation.

22 Claims, 1 Drawing Sheet

OTHER PUBLICATIONS

Philip E. Vercoe, et al., "Nucleotide sequence and transcriptional analysis of the celD β-glucanase gene from *Ruminococcus flavefaciens* Fd-1", Canadian Journal of Microbiology, vol. 41, No. 1, pp. 27-34, (1995).

Kazuhiko Juni, et al., "Controlled Release Of Aclarubicin, An Anticancer Antibiotic, From Poly-β-Hydroxybutyric Acid Microspheres", Journal of Controlled Release, vol. 4, pp. 25-32 (1986).

Alexander Steinbüchel, et al., "Diversity of bacterial polyhydroxyalkanoic acids", FEMS Microbiology Letters, vol. 128, pp. 219-228 (1995).

Y. Yamamoto et al., "An Experimental Study on the Releasing Rate of Poly (3-hydroxybutyrate) microspheres-II", Drug Delivery System 8(2):131-6 (1993).

P.E. Vercoe, et al., "Nucleotide Sequence and Transcriptional Analysis of the celD β-glucanase Gene from *Ruminococcus flavefaciens* Fd-1", Can. J.I Microbiol 41(1): 27-34(1995).

Ralf Jossek and Alexander Steinbüchel, "In vitro synthesis of poly(3-hydroxybutyric acid) by using an enzymatic coenzyme A recycling system", FEMS Microbiology Letters vol. 168, 319-324 (1998).

Geoffrey A. R. Nobes, et al., "Growth and kinetics of in vitro poly([R]-(−)-3-hydroxybutyrat) granules interpreted as particulate polymerization with coalescence", Macromol. Rapid Commun. vol. 21, 77-84 (2000).

John L. Speier, et al., "The Addition of Silicon Hydrides to Olefinic Double Bonds. Part I. Th Use of Phenylsilane, Diphenylsilane, Phenylmethylsilane, Amylsilane and Tribromosilan", J. Amer. Chem. Soc., vol. 78, 2278-81 (May 20, 1956).

Henry J. Vogel and David M. Bonner, "Acetylornithinase of *Escherichia coli*: Partial Purification and Some Properties", Department of Microbiology, Yale University, New Haven, Connecticut, 97-106 (Jun. 8, 1955).

Won Ho Park, et al., "Epoxidation of Bacterial Polyesters with Unsaturated Side Chains. I. Rate of Epoxidation and Polymer Properties", Journal of Polymer Science Part A: Polymer Chemistry, vol. 36, 2381-2387 (1998).

Milena Reháková, et al., "Depolymerization reactions of hyaluronic acld in solution", Int. J. Biol. Macromol. vol. 16, 121-124 (1994).

Y.B. Kim, et al., "Preparation and Characterization of Poly(β-hydroxyalkanoates) Obtain d from *Pseudomonas olevorans* Grown with Mixtures of 5-Phenylvaleric Acid and n-Alkanoic Acids", Macromolecules vol. 24, 5256-5260 (1991).

Anthony G. Ostle, "Nile Blue A as a Fluorescent Stain for Poly-β-Hydroxybutyrate," App. Environ. Microbiol. vol. 44(1):238-41 (1982).

M. Yamaguchi et al., "Oxidation of ω-(Benzoyloxy)alkanols with an Oxoaminium Salt," J. Org. Chem., vol. 55:1490-2 (1990).

S.M. Arostegui et al., "Bacterial Polyesters Produced by *Pseudomonas oleovorans* Containing Nitrophenyl Groups," Macromolecules vol. 32:8315-18 (1999).

H. Okada and H. Toguchi, "Biodegradable Microspheres in Drug Delivery," Crit. Rev. Therap. Drug Carrier Sys., vol. 12(1):1-99(1995).

D. Pelletier and C.S. Harwood, "2-Hydroxyclohexanecarboxyl Coenzyme A Dehydrogenase, an Enzyme Characteristic of the Anaerobic Benzoate Degradation Pathway Used by *Rhodopseudomonas palustris*," J. Bacteriol. vol. 182(10):2753-60 (2000).

G. Spenlehauer et al., Formation and Characterization of Cisplatin Loaded Poly(*d-1*-Lactide) Microspheres for Chemoembolization, J. Pharm. Sci. vol. 75(8):750-55 (1986).

Katharina Fritzsche, et al., "An unusual bacterial polyester with a phenyl pendant group", Makromol. Chem. vol. 191, 19571965 (1990).

Joanne M. Curley, et al., "Production of Poly(3-hydroxyalkanoates) Containing Aromatic Substituents by *Pseudomonas oleovrans*", Macromolecules vol. 29, 1762-1766 (1996).

Yasuo Takagi, et al, "Biosynthesis of Polyhydroxyalkanoate with a Thiophenoxy Side Group Obtained from *Psuedomonas putida*", Macrtomolecules vol. 32, 8315-8318 (1999).

Q. Qi, et al., "In vitro synthesis of poly(3-hydroxydecanoate): purification and enzymatic characterization of type II polyhydroxyalkanoate synthases PhaC1 and PhaC2 from *Pseudomonas aeruginosa*", Appl. Microbiol. Biotechnol vol. 54, 37-43 (2000).

Robert W. Lenz, et al., Extracellular polymerization of 3-hydroxyalkanoate monomers with the polymerase of *Alcaligenes eutrophus*, International Journal of Biological Macromol cules vol. 25, 55-60 (1999).

J. Sambrook, et al, "Molecular Cloning", 1,572, Cold Spring Harbor Laboratory Press 1989.

K. Fritzsche and RW Lenz, "Production of unsaturated polyesters by *Pseudomonas oleovorans*", Int. J. Biol. Macromol. vol. 12:85-91 (1990).

Bha Rehm et. al., "A New Metabolic Link Between Fatty Acid de nova Synthesis and Polyhdroxyalkanoic Acid Synthesis," J. Biol. Chem. vol. 273:24044-24051 (1998).

H. Ritter and A.G. von Spee, "Poly(3-hydroxy-5-phenoxypentanoate-*co*-3-hydroxy-9-ph noxy-nonanoate) from *Pseudomonas oleovorans*," Macromol. Chem. Phys. vol. 195:1665-72 (1994).

W.H. Park et al., "Epoxidation of Bacterial Polyesters with Unsaturated Side Chains. I. Production and Epoxidation of Polyesters from 10-Undecenoic Acid", Macromolecules vol. 31:1480-6(1998).

M.N. Kraak, "In vitro activities of granule-bound poly[(R)-3-hydroxyalkanoate] polymerase C1 of *Pseudomonas oleovorans*", Eur. J. Biochem. vol. 250:432-9 (1997).

S. Antoun et al., "Production of a Chiral Polyester by *Pseudomonas oleovorans* Grown with 5-Phenyl-2,4-Pentadienoic Acid", Chirality vol. 3:492-4 (1991).

T.U. Gerngross and D.P. Martin, "Enzyme-catalyzed synthesis of poly[(R)-(−)-3-hydroxybutyrate]: Formation of macroscopic granules in vitro", Proc. Natl. Acad. Sci. vol. 92:6279-83 (1995).

Be Ramsay et al., "Effect of Nitrogen Limitation on Long-Side-Chain Poly-β-Hydroxyalkanoate Synthesis by *Pseudomonas resinovorans*", Appl. Environ. Microbiol. vol. 58(2):744-6 (1992).

Y. Yamamoto, et al., "An Experimental Study on the Releasing Rate of Poly (3-hydroxybutyrate) microspheres", Drug Delivery System vol. 7(5):367-71(1992).

T. U. Gerngross, et al., "Enzyme-catalyzed synthesis of poly [(R)-(—)-3-hydroxybutyrate]: Formation of macroscopic granules in vitro", Proc. Natl. Acad. Sci., vol. 92, Jul. 1995, pp. 6279-6283.

Robert W. Lenz, et al., "Extracellular polymerization of 3-hydroxyalkanoate monomers with the polymerase of *Alcaligenes eutrophus*", International Journal of Biological Macromolecules, vol. 25, 1999, pp. 55-60.

Lara L. Madison, et al., "Metabolic Engineering of Poly(3-Hydroxyalkanoates): From DNA to Plastic", Microbiology and Molecular Biology Reviews, vol. 63, No. 1, Mar. 1999, pp. 21-53.

* cited by examiner

FIGURE
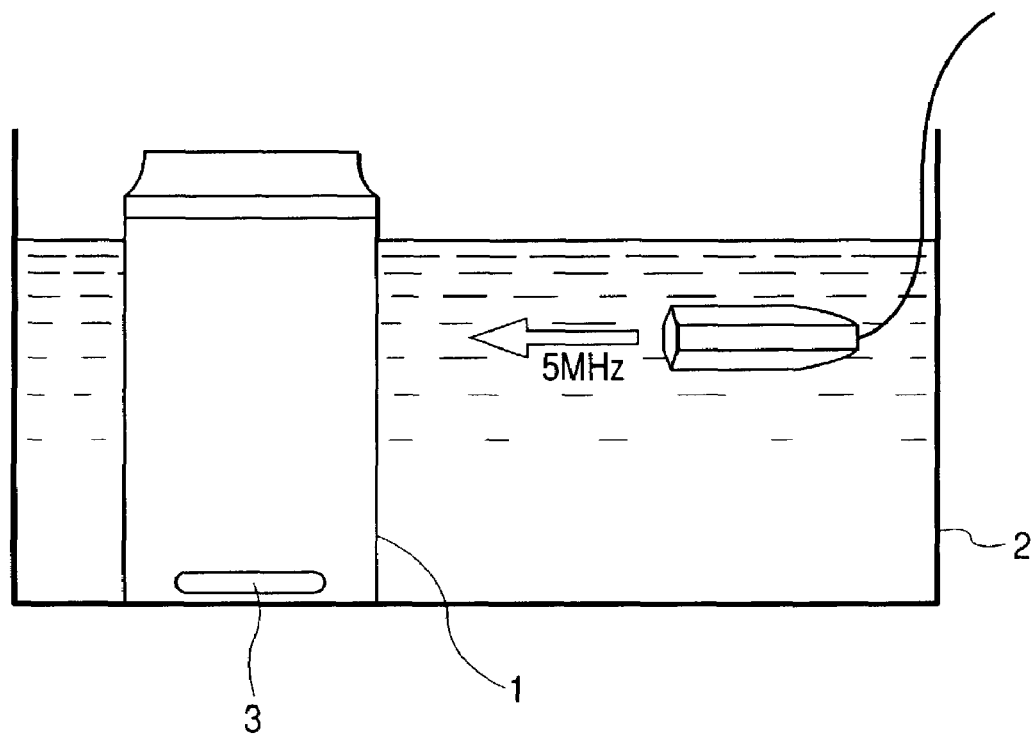

PARTICULATE CONSTRUCT COMPRISING POLYHYDROXYALKANOATE AND METHOD FOR PRODUCING IT

BACKGROUND OF THE INVENTION

1. Field of the Invention

The present invention relates to particulate construct such as microcapsules featured in that a solid phase containing polyhydroxyalkanoate (which may hereinafter be abbreviated as PHA) which at least contains 3-hydroxyalkanoic acid as a monomer unit incorporates at least one of solid phase, liquid phase and gaseous phase, and particulate construct such as microcapsules featured in that the aforementioned PHA coats at least one of solid phase, liquid phase and gaseous phase. The present invention also relates to a method for producing particulate construct such as microcapsuleas featured by causing, from w/o type emulsion consisting of water phase and oil phase containing at least PHA or w/o/w type emulsion obtained by emulsifying such w/o type emulsion in water phase, PHA to incorporate or coat at least one of solid phase, liquid phase and gaseous phase, for example a method for producing particulate construct such as microcapsules by in-liquid drying, phase separation, spray drying or a similar method.

The present invention further relates to a producing method of executing encapsulation with PHA from o/w type emulsion consisting of oil phase containing at least PHA and water phase, wherein such encapsulation is coating, for example a method for producing particulate construct such as microcapsules by in-liquid drying, phase separation, spray drying or a similar method.

The present invention further relates to a method for producing particulate construct such as microcapsules featured, in w/o type emulsion consisting of water phase and oil phase containing at least PHA or w/o/w type emulsion obtained by emulsifying such w/o type emulsion in water phase, by synthesizing PHA utilizing PHA synthesizing enzyme and 3-hydroxyacyl coenzyme A contained in the water phase thereby causing PHA to incorporate or coat at least one of solid phase, liquid phase and gaseous phase, wherein the encapsulation is coating.

The present invention further relates to a method for producing particulate construct such as microcapsules featured, in w/o type emulsion consisting of oil phase and water phase containing at least PHA synthesizing enzyme and 3-hydroxyacyl coenzyme A, by polymerizing 3-hydroxyacyl coenzyme A by the PHA synthesizing enzyme in the water phase to synthesize PHA thereby executing encapsulation with PHA, wherein the encapsulation is coating.

The present invention further relates to particulate construct such as slow-releasing microcapsules containing a chemical substance such as pharmaceuticals or agricultural chemicals, and a method for producing the particulate construct such as the above-mentioned microcapsules.

The present invention further relates to particulate construct containing pigment, dye, hemoglobin, cosmetic component or fertilizer component, and a producing method thereof. It further relates to an ink composition, a blood cell composition, a cosmetic composition or a fertilizer composition containing such particulate construct, and a producing method thereof.

The present invention further relates to hollow particulate construct such as hollow microcapsules incorporating gaseous phase, a producing method thereof, and an ultrasonic contrast medium utilizing such hollow particulate construct as an ultrasonic reflecting member. In addition, the present invention relates to the application of the hollow particulate construct such as the above-mentioned hollow microcapsules to the ultrasonic contrast medium administered orally or non-orally into a living organism and utilized for ultrasonic diagnosis.

2. Related Background Art

Microcapsules have been studied in various fields such as pharmaceuticals, agricultural chemicals, foods, adhesives and liquid crystals. For example, in the pharmaceutical field, application as a slow-releasing preparation has been studied to improve drugs of a short action period for prolonged action period, where not only prolonged pharmacological effects but also other effects such as decrease in the dosage, adverse effects, and improvement in the non-compliance are expected. Recently, various controlled release pharmaceutical preparations have been proposed that can release chemicals at a constant rate, substantially at zero-order. Such controlled release preparations are being developed as preparations for oral administration, injection, and skin patch application.

Microcapsules are also studied in various other fields, for example, in the cosmetic field, as means for delivering an unstable effective component to the desired site and releasing it slowly; in the agricultural field, as chemicals and fertilizers having slow-releasing function; and in the field of recording materials, as encapsulated inks.

In the pharmaceutical field, U.S. Pat. No. 6,146,665 discloses a method of producing fine porous particles of polyhydroxyalkanoate entrapping a hydrophilic drug therein, and a pharmaceutical composition comprising a core material being an oil drop dissolving therein a lipophilic drug encapsulated by a polyhydroxyalkanoate shell.

Although oral preparations have been widely investigated and developed and many preparations have been commercialized, injection preparations are limited to the depot preparations of insulin. This is ascribable to the lack of development of the polymer compound for conferring slow releasing function. In case of oral preparations, the polymer compound need not be decomposed in the body, but, in case of injection preparations, the polymer compound is absolutely required to be decomposed in, metabolized in and excreted from the body without expressing toxicity therein, and also required are other strict conditions such as absence of local disturbance in the injection site.

Under such circumstances, recently investigated are various polymer compounds, especially polylactic acid, lactic acid-glycolic acid copolymer and hydroxybutyric acid-glycolic acid copolymer, those employed as sewing thread in surgical operation, are expected as safe and useful polymer compounds (Japanese Patent Publication No. 1-57087, WO 94/10982 and Japanese Patent Applications Laid-open Nos. 8-151322 and 8-217691).

In fact, there have been reported various micro encapsulation techniques to prepare slow release preparations entrapping a hydrophilic drug in these polymer compounds. Also for poly-3-hydroxybutyric acid (which may hereinafter be abbreviated as PHB), there are reported microcapsules for controlled release of the active peptide component, and microcapsules containing lactide (Japanese Patent Application Laid-open No. 61-431119, Drug Delivery System 7(5), 367-371, 1992 and ibid., 8(2), 131-136, 1993). Also for 3-hydroxybutyric acid/4-hydroxybutyric acid copolymer, there is disclosed a slow release preparation capable of controlling the release rate of a physiologically active substance with the monomer ratio (Japanese Patent Application Laid-open No. 11-199514).

Most of these technologies are to include water-soluble drugs. For example, Japanese Patent Application Laid-open Nos. 60-100516 and 62-201816 disclose a method of producing highly dispersible slow release microcapsules of a water-soluble drug by using the in-water drying method at a high trapping rate. Also Japanese Patent Application Laid-open Nos. 1-163135 and 2-124814 disclose a method of including a water-soluble drug in a prophylactic acid-glycolic acid copolymer, and Japanese Patent Application Laid-open Nos. 2-124814 and 5-294839 disclose slow release preparations including a physiologically active polypeptide and cisplatin respectively. Also Japanese Patent Application Laid-open No. 4-321622 discloses long-term slow releasing microcapsules including copolymer or homopolymer of which lactic acid/glycolic acid ratio is 80/20 to 100/0 and weight-averaged molecular weight is 7,000 to 30,000, capable of releasing polypeptides at zero-order over two months or more.

The conventional production methods for the microcapsules can be largely classified into chemical methods such as interfacial polymerization and in-situ polymerization, physicochemical methods such as phase separation (coacervation), interfacial precipitation, in-liquid drying and orifice method, and mechanical methods such as spray drying and dry mixing. Among these methods, the interfacial polymerization, in-situ polymerization, in-liquid drying, orifice method and phase separation (coacervation) have been applied for microencapsulating water-soluble agents.

Although many reports have been made on the slow-releasing microcapsules containing various physiologically active polypeptides or water-soluble low molecular weight drugs (Critical Reviews in Therapeutic Drug Carrier Systems, 12, pp 1-9 (1995); Japanese Patent Publication No. 2-503315; EPA 0586238; J. Pharm. Sci., 75, pp 750-755 (1986); and Japanese Patent Application Laid-open No. 57-118512), most of such microcapsules are unsatisfactory in view of long-term slow releasing properties according to the applications, since (1) the drug leakage to the external water phase is high during the production process resulting in low trapping rate, (2) the obtained microcapsules are generally porous and show a large initial release, or (3) the physiologically active substance is modified during the production process leading to insufficient bioavailability.

As regards improvement of the slow releasing properties of microcapsules, Japanese Patent Application Laid-open No.61-63613 discloses, in microcapsules utilizing polylactic acid as the base material, to uniformly dissolve an oil-soluble additive (medium chain fatty acid triglyceride, lower fatty acid triglyceride etc.), being soluble in an organic solvent and digestable in the living body, in a solution of polylactic acid in such an organic solvent, in order to prevent the decrease of the releasing speed of the active component in the polylactic acid-based microcapsules after a certain time from the administration. However it does not teach preparation of microcapsules using other base materials or an aqueous solution of the active component. Japanese Patent Application Laid-open No. 8-151321 discloses microcapsules containing a polymer and an amorphous, water-soluble physiologically active substance, being produced from an S/O/W type emulsion, but it does not teach at all a production method of microcapsules containing an aqueous solution of a drug as the internal water phase or a method utilizing a metal complex of a water-soluble physiologically active peptide. Also EP 0765660 discloses microcapsules containing an amorphous 2-piperazinone-1-acetic acid derivative and use of an s/o/w emulsion in the preparation thereof, but does not teach a production method of microcapsules using an aqueous solution of a drug as the internal water phase or a method utilizing a metal complex of water-soluble physiologically active peptide. In general, in preparation of microcapsules containing a water soluble physiologically active substance, w/o type is superior to s/o type where the drug is used in solid state, in consideration of uniform drug content and operability. Thus, w/o type is preferable in the industrial scale mass production.

A problem often pointed out in the drug release control using a slow releasing preparation is a phenomenon called initial burst phenomenon, drug release in a large amount at a time in the initial releasing stage after administration of the preparation to the subject. If such an initial burst occurs, the drug concentration in the blood may exceed the permissible upper limit, endangering the subject. Although initial burst can be prevent to a certain extent by selecting the kind of the drug compound and structure of the biodegradable polymer, there has not been found a basic solution for preventing initial burst yet. On the other hand, there is a requirement for including a drug compound at a concentration as high as possible in microcapsules, in order to achieve slow release of the drug compound over a long period or to formulate an expensive drug in a certain amount of preparation as small as possible for economic advantage.

However, by the conventionally known methods for producing microcapsules, percentage of drug compound trapped in the microcapsules (trapping rate) tends to be lowered. In case of a water-soluble drug, especially, a serious problem is that the drug tends to escape outside the membrane, resulting in a low trapping rate. On the other hand, microcapsules prepared by a method enabling a high trapping rate have a drawback that initial burst tends to occur in the drug release.

Meantime, in the ultrasonic diagnosis or inspection, it is proposed to administer microballoons, which are small polymer spheres, into the living body as an ultrasonic reflecting agent. Small bubbles dispersed in liquid, i.e., microbubbles, are conventionally known to be a very effective ultrasonic reflector for the ultrasonic diagnosis or inspection. However, such microbubbles will disappear in a short time, in several minutes at longest even when a stabilizing agent is added. For this reason, microbubbles have to be administered in the patient immediately after preparation, and are therefore difficult to use in the actual medical locations. In addition, in order to facilitate permeation through the blood vessel after the administration into the body, the size of the bubbles has to be within a range of about 1 to 10 μm. Most of the generated microbubbles are within a range of 40 to 50 μm, so that such microbubbles are not necessarily suitable for administration to the body for the purpose of ultrasonic diagnosis.

In order to solve these drawbacks of microbubbles, it has been proposed administration of microballoons, small polymer spheres, to the body (for example, Japanese Patent Application Laid-open No. 3-94774). However, microballoons prepared by the conventional method must be administered in a large amount in order to obtain a high contrast effect. Partcularly, for the cardiac muscle, there is no effective contrast medium that can provide the required high contrast effect. This is primarily because such balloons often do not have hollow structure inside and it is difficult to obtain uniform small particles containing bubbles inside. Besides, such microballoons when administered in a large amount may give an excessive burden to the body, thus having a safety problem to be solved.

Meanwhile, active studies have been done to produce polymer compounds by using biotechnology, and partly in practice. For example, known microbial polymers include poly-hydroxyalkanoates (PHAs) such as poly-3-hydroxy-n-butyric acid (PHB), and copolymers of 3-hydroxy-n-butyric acid and 3-hydroxy-n-valeric acid (PHB/V); polysaccharides such as bacterial cellulose and pullulan; and polyamino acids such as poly-γ-glutamic acid and polylysine. Particularly, PHA can be processed into various products by melt-preparation etc., just like other existing plastics. In addition, because of excellent biocompatibility, application of PHA as medical soft materials is also expected.

It has beep reported that many microorganisms produce PHA and accumulate it within cells. For example, microbial productions of PHB/V by *Alcaligenes eutrophus* H16 (ATCC No. 17699), *Methylbacterium* sp., *Paracoccus* sp., *Alcaligenes* sp., and *Pseudomonas* sp. have been reported (for example, Japanese Patent Application Laid-Open No 5-7492, Japanese Patent Publication Nos. 6-15604, 7-14352, and 8-19227). Furthermore, *Comamonas acidovorans* IFO 13852 produces PHA comprised of monomer units of 3-hydroxy-n-butyric acid and 4-hydroxy-n-butyric acid (Japanese Patent Application Laid-Open No. 9-191893), and *Aeromonas caviae* produces a copolymer of 3-hydroxy-n-butyric acid and 3-hydroxyhexanoic acid (Japanese Patent Application Laid-Open Nos. 5-93049 and 7-265065).

Biosynthesis of these PHB and PHB/V is an enzymatic polymerization reaction using as a substrate (R)-3-hydroxybutyryl CoA or (R)-3-hydroxyvaleryl CoA that is synthesized from various carbon sources through various metabolic pathways within a living organism. The enzyme that catalyzes this polymerization reaction is PHB synthetase (this can be referred to as PHB polymerase or PHB synthase). CoA is an abbreviation for coenzyme A, and its chemical structure is represented by the following chemical formula.

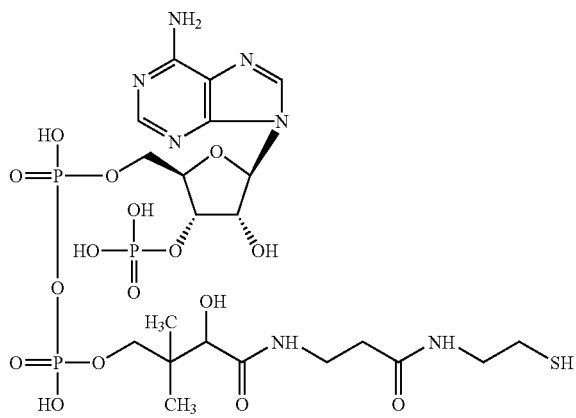

Recently, active studies on polyhydroxyalkanoate comprised of 3-hydroxyalkanoic acid units of medium-chain-length (about 3 to 12 carbon atoms) (mcl-PHA) have been conducted.

For example, Japanese Patent No. 2642937 discloses that *Pseudomonas oleovorans* ATCC 29347 can produce PHA comprised of 3-hydroxyalkanoic acid monomer units of 6 to 12 carbon atoms from non-cyclic aliphatic hydrocarbons. In addition, it has been reported, in Appl. Environ. Microbiol., 58, 746 (1992), that *Pseudomonas resinovorans* produces PHA of which monomer units are 3-hydroxy-n-butyric acid, 3-hydroxyhexanoic acid, 3-hydroxyoctanoic acid, and 3-hydroxydecanoic acid using octanoic acid as a sole carbon source, and it also produces PHA of which monomer units are 3-hydroxy-n-butyric acid, 3-hydroxyhexanoic acid, 3-hydroxyoctanoic acid, and 3-hydroxydecanoic acid using hexanoic acid as sole carbon source. Here, the 3-hydroxyalkanoic acid monomer units longer than the raw material fatty acid are considered derived from the fatty acid synthesizing pathway described below.

Int. J. Biol. Macromol., 16 (3), 119 (1994) reported that *Pseudomonas* sp. Strain 61-3 produces PHA comprised of monomer units of 3-hydroxyalkanoic acids such as 3-hydroxy-n-butyric acid, 3-hydroxyhexanoic acid, 3-hydroxyoctanoic acid, and 3-hydroxydecanoic acid, and 3-hydroxyalkenoic acids such as 3-hydroxy-5-cis-decenoic acid and 3-hydroxy-5-cis-dodecenoic acid, using sodium gluconate as a sole carbon source.

The above-described PHAs are comprised of monomer units having alkyl groups as the side chain (usual-PHAs). However, when wider application of PHA, e.g., as a functional polymer, is intended, PHA having side chains other than alkyl groups (for example, side chains having substituents such as phenyl group, unsaturated hydrocarbons, ester groups, allyl group, cyano group, halogenated hydrocarbons, and epoxides) is extremely useful (unusual-PHA).

As for biosynthesis of unusual-PHA having phenyl groups, it was reported that *Pseudomonas oleovorans* produced PHA having 3-hydroxy-5-phenylvaleric acid units from 5-phenylvaleric acid (Macromolecules, 24, 5256-5260 (1991), Macromol. Chem., 191, 1957-1965 (1990); Chirality, 3, 492-494 (1991)). Polymers, 29, 1762-1766 (1996) reported that *Pseudomonas oleovorans* produced PHA having 3-hydroxy-5-(4-tolyl)valeric acid units from 5-(4-tolyl)valeric acid (5-(4-methylphenyl)valeric acid). Further, Polymers, 32, 2889-2895 (1999) reported that *Pseudomonas oleovorans* produced PHA having 3-hydroxy-5-(2,4-dinitrophenyl) valeric acid units and 3-hydroxy-5-(4-nitrophenyl)valeric acid units from 5-(2,4-dinitrophenyl)valeric acid.

As for unusual-PHA having phenoxy groups, Macrocol. Chem. Phys., 195, 1665-1672 (1994) reported that *Pseudomonas oleovorans* produced PHA having 3-hydroxy-5-phenoxyvaleric acid units and 3-hydroxy-9-phenoxynonanoic acid units from 11-phenoxyundecanoic acid. Also, Polymers, 29, 3432-3435 (1996) reported that *Pseudomonas oleovorans* produced a PHA having 3-hydroxy-4-phenoxybutyric acid units and 3-hydroxy-6-phenoxyhexanoic acid units from 6-phenoxyhexanoic acid, a PHA having 3-hydroxy-4-phenoxybutyric acid units, 3-hydroxy-6-phenoxyhexanoic acid units, and 3-hydroxy-8-phenoxyoctanoic acid units from 8-phenoxyoctanoic acid, and a PHA having 3-hydroxy-5-phenoxyvaleric acid unit and 3-hydroxy-7-phenoxyheptanoic acid units from 11-phenoxyundecanoic acid. Further, Can. J. Microbiol., 41, 27-34 (1995) reported that *Psudomonas oleovorans* ATCC 29347 and *Pseudomonas putida* KT 2442 produced PHA having 3-hydroxy-p-cyanophenoxyhexanoic acid units and PHA having 3-hydroxy-p-nitrophenoxyhexanoic acid units from p-cyanophenoxyhexanoic acid and p-nitrophenoxyhexanoic acid respectively. Japanese Patent No. 2989175 describes a homopolymer comprised of 3-hydroxy-5-(monofluorophenoxy)valeric acid units or 3-hydroxy-5-(difluorophenoxy)valeric acid units and a copolymer containing at least 3-hydroxy-5-(monofluorophenoxy)pentanoate unit or 3-hydroxy-5-(difluorophenoxy)pentanoate unit and a method for producing such homopolymer or copolymer, reciting that such homopolymer and copolymer can provide water-repellency and stereoregularity with high melting point and good workability.

As an example of unusual-PHA having a cyclohexyl group, Polymers, 30, 1611-1615 (1997) reported that *Pseudomonas oleovorans* produced such PHA from cyclohexylbutyric acid or cyclohexylvaleric acid.

Among the PHAs having a substituent in the side chain, development of PHA having a sulfide (—S—) sulfur atom in the side chain was reported in Macromolecules, 32, 8315-8318(1999) utilizing *Pseudomonas putida* 27N01 strain and also utilizing octanoic acid and 11-(phenylsulfanyl) undecanoic acid as substrate to produce PHA containing 3-hydroxy-5-(phenylsulfanyl) valeric acid and 3-hydroxy-7-(phenylsulfanyl) heptanoic acid as monomer units. In this process there was employed a method of preculturing the *Pseudomonas putida* 27N01 strain in a culture medium containing only octanoic acid as the growth substrate, and inoculating the obtained seed culture in a culture medium containing only 11-(phenylsulfanyl) undecanoic acid as the substrate.

Also Polymer Preprints, Japan, Vol. 49, No. 5, 1034(2000) reported production utilizing *Pseudomonas putida* 27N01 strain and utilizing 11-[(phenylmethyl)sulfanyl] heptanoic acid as the substrate to produce PHA consisting of two monomer units, namely 3-hydroxy-5-benzylthio-valeric acid and 3-hydroxy-87-[(phenylmethyl)sulfanyl] heptanoic acid. In this process there was employed a method of preculturing the *Pseudomonas putida* 27N01 strain in a culture medium containing octanoic acid only as the proliferating substrate, and inoculating the obtained culture liquid in a culture medium containing 11-[(phenylmethyl)sulfanyl] undecanoic acid only as the substrate.

These mcl-PHA and unusual-PHA are synthesized through an enzymatic polymerization reaction using (R)-3-hydroxyacyl CoA as a substrate. Such 3-hydroxyacyl CoAs are produced through various metabolic pathways (for example, β-oxidation pathway or fatty acid synthesis pathway) in a living organism from different alkanoic acids. The enzyme that catalyzes this polymerization reaction is PHA synthetase (this can be referred to as PHA polymerase or PHA synthase). The following is the reaction route from alkanoic acid to PHA via the β-oxidation pathway and polymerization reaction by PHA synthetase.

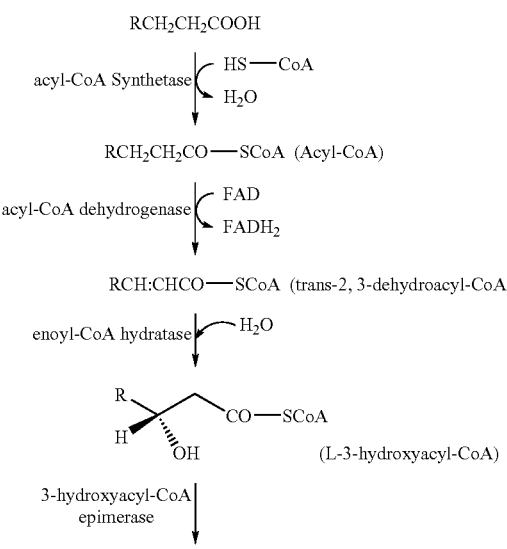

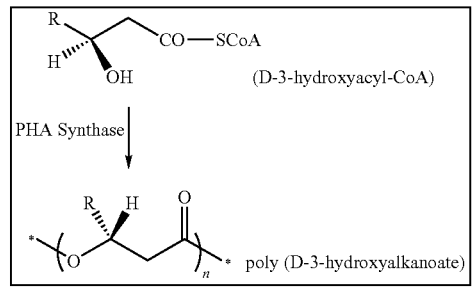

On the other hand, when the production is performed through the fatty acid synthesis pathway, it is considered that (R)-3-hydroxyacyl-ACP (ACP means acyl carrier protein) generated in this pathway is converted to (R)-3-hydroxyacyl CoA from which PHA is synthesized by PHA synthetase.

Recently, attempts have been made to synthesize PHA in vitro using PHB synthetase or PHA synthetase isolated from cells.

For example, Proc. Natl. Acad. Sci. USA, 92, 6279-6283 (1995) describes that PHB comprised of 3-hydroxy-n-butyric acid units has been successfully synthesized by using PHB synthetase derived from *Alcaligenes eutrophus* and 3-hydroxybutyryl CoA as a substrate. In addition, Int. J. Biol. Macromol., 25, 55-60 (1999) describes that PHA comprised of 3-hydroxy-n-butyric acid units or 3-hydroxy-n-valeric acid units has been successfully synthesized by reacting PHB synthetase derived from *Alcaligenes eutrophus* with 3-hydroxybutyryl CoA or 3-hydroxyvaleryl CoA. Further, this report mentions that, when racemic 3-hydroxybutyryl CoA was reacted with PHB synthetase, PHB comprised of only (R) 3-hydroy-n-butyric acid units was successfully synthesized due to the stereoselectivity of the enzyme. Macromol. Rapid Commun., 21, 77-84 (2000) reported in vitro PHB synthesis using PHB synthetase derived from *Alcaligenes eutrophus*.

FEMS Microbiol. Lett., 168, 319-324 (1998) describes that PHB comprised of 3-hydroxy-n-burytic acid units was successfully synthesized by reacting PHB synthetase derived from *Chromatium vinosum* with 3-hydroxybutyryl CoA.

In Appl. Mirobiol. Biotechnol., 54, 37-43 (2000), PHA comprised of 3-hydroxydecanoic acid is synthesized by reacting PHA synthetase derived from *Pseudomonas aeruginosa* with 3-hydroxydecanoyl CoA.

[Problems to Be Solved]

As described above, application of biotechnological methods to polymer synthesis may enable synthesis of new polymer compounds which can not be made by conventional organic synthesis or enable imparting new functions and constructs to polymer compounds. In addition, there are many cases where conventional multi-step reaction can be replaced with only one step reaction, so that simplification of the production process, cost reduction, and time saving are expected. Further, this enables consumption reduction of organic solvents, acids, alkalis, surfactants, etc., moderate reaction conditions, and synthesis from non-petroleum raw materials or crude raw materials, thus enables a synthesis process of lower environmental burden and of resource-recycling type. In more detail with synthesis from the crude raw materials, the substrate specificity of the enzyme used as a catalyst in biotechnological synthesis is high in general, so that it is possible to selectively promote a desired reaction even when the low purity raw material is used. Thus, use of waste materials or recycled materials can be expected.

Meantime, the present inventors were paying attention to microcapsules of a drug coated with a polymer compound as an elementary technology to confer a large additional value upon a polymer compound. By coating a drug with a polymer compound, the obtained microcapsules acquire very useful functionalities, particularly slow releasing ability. Conventionally, such microcapsules have been mostly prepared by organic synthesis.

If such microcapsules can be produced by a bioengineering method as explained above, it is expected to enable utilization of novel polymer compounds and realization of novel functions and structures, and also to realize a manufacturing process of low environmental burden and resource recycling with a low cost. For example, utilizing very strict molecular recognizing ability and stereo selectivity specific to the catalytic action of living organisms, there can be produced microcapsules covered with a novel functional polymer compound or a polymer compound of extremely high chirality by an extremely simple process of environmentally low burden.

Therefore, the object of the present invention is to provide particulate construct such as microcapsules utilizing the aforementioned highly functional polymer compound and a producing method therefor, and a method for producing particulate construct such as microcapsules by a bioengineering process.

As explained in the foregoing, the inclusion of a water-soluble drug in microcapsules comprised of polylactic acid or lactic acid-glycollic acid copolymer which are biodegradable polymers still has many issues in the drug releasing characteristics. Also the water-soluble drug has a drawback of tending to be easily dispersed and not effectively contained in the particulate construct or not microencapsulated.

The present invention is conceived to resolve the drawbacks of the aforementioned conventional technologies, and the object of the present invention is to provide a slow releasing preparation not showing practically defective initial release and showing practically acceptable zero-order release for a predetermined period even in case of particulate construct such as microcapsules including a drug, particularly a water-soluble drug, or microcapsules including a water-insoluble drug (including drugs generally called hardly soluble in water), and a producing method therefor. Also the present invention is to provide a slow releasing preparation of a high drug content stably including a drug, particularly a water-soluble drug, in particulate preparation such as microcapsules, and a producing method therefor.

For example, the fine particles disclosed in the U.S. Pat. No. 6,146,665 are those trapping a hydrophilic drug in porous granules consisting of polyhydroxyalkanoate free of toxicity, biodegradable and capable of in situ trapping the drug, but, because of porous structure, they rapidly release the hydrophilic drug by diffusion, so that the slow releasing property is difficult to control.

A problem to be resolved by the present invention is to optimize the drug holding ability and slow releasing ability by optimizing the structure of polyhydroxyalkanoate, thereby providing drug holding particles excellent in holding ability and capable of controlling the slow releasing ability even for hydrophilic drugs, other water-soluble substances, oleophilic drugs or other hydrophobic substances.

Further, the present invention provides particulate construct including a pigment, a dye, an agricultural chemical component, hemoglobin, a cosmetic component or a fertilizer component in the aforementioned particulate construct and a producing method therefor. It further provides an ink composition, an agricultural chemical composition, a hemocyte composition, a cosmetic composition or a fertilizer composition including such particulate construct, and a producing method therefor.

Also, as explained in the foregoing, the microballoons obtained in the conventional method, in which the particles do not have hollow structure inside and uniform fine particles including many bubbles are difficult to obtain, have to be administered in a large amount in order to obtain a high contrast effect in the ultrasonic diagnosis or inspection, and, particularly in contrast formation of the cardiac muscles, there has not been an effective contrast medium capable of sufficiently meeting the desired high contrast effect. The administration of such microballoons in a large amount may give an excessive burden to the living organism in certain cases and there are problems to be solved in terms of safety.

In consideration of the foregoing, the present invention is to provide a method for producing hollow particulate construct such as hollow microcapsules, capable of selectively obtaining fine particles having a hollow structure of microcapsule shape having a single PHA membrane in order to include many bubbles in the fine particles, and also provides an ultrasonic contrast medium exhibiting high contrast effect utilizing the hollow particulate constructe such as hollow microcapsules and a producing method therefor. More specifically, it provides an ultrasonic contrast medium of high contrast effect, usable for ultrasonic diagnosis or inspection of cardiac muscles, cardiac cavity and liver.

SUMMARY OF THE INVENTION

The particulate construct of the present invention is featured by being comprised of a solid phase containing polyhydroxyalkanoate which contains a 3-hydroxyalkanoic acid unit and including at least one solid phase, liquid phase and gaseous phase.

The present invention also relates to a bioengineering method of adding 3-hydroxyacyl CoA to a reaction system containing PHA synthesizing enzyme to synthesize desired PHA at the water/oil interface to produce particulate construct in which at least one of solid phase, liquid phase and gaseous phase is encapsulated or coated with PHA.

The preparation of the present invention is a preparation containing the aforementioned particulate construct. Also the method of the present invention for producing the preparation is a method of producing the preparation including the producing process of the aforementioned particulate construct. Such preparation shows a low initial release of the drug, particularly a substantially water-insoluble drug, and is suitable as a slow releasing preparation of a high drug content, showing satisfactory slow releasing property over a long period. Also such preparation shows a low initial release for the drug, particularly a water-soluble drug, and is suitable as a slow releasing preparation of a high drug content, showing satisfactory slow releasing property over a long period.

Also the present inventors have found, as a result of intensive investigation for developing an ultrasonic contrast medium of high contrast effect, that the hollow particulate construct of the present invention is suitable as hollow particulate construct capable of containing many bubbles in the fine particles, and that a contrast medium of higher ultrasonic contrast effect in the living organism by dispersing the aforementioned hollow particulate construct in water, then drying it under a reduced pressure and filling the drying equipment with perfluorocarbon gas thereby filling the interior of the hollow structure, namely the bubbles, of the hollow particulate construct with the aforementioned gas, whereby the ultrasonic contrast medium of the present invention is attained.

Thus, the ultrasonic contrast medium of the present invention is an ultrasonic contrast medium containing the aforementioned hollow particulate construct. The ultrasonic contrast medium of the present invention is useful in contrast formation of cardiac muscles, cardiac cavities (such as ventricle and atrium constituting heart) and liver.

BRIEF DESCRIPTION OF THE DRAWINGS

FIGURE is a schematic view showing the principle of a test method in an experimental example 16.

DETAILED DESCRIPTION OF THE PREFERRED EMBODIMENTS

The particulate construct of the present invention (hereinafter also called microcapsules but not limited to a two-layered structure and including any structure in which at least one of solid phase, liquid phase and gaseous phase is incorporated in solid phase) can be microcapsules of a configuration in which at least one of solid phase, liquid phase and gaseous phase is encapsulated or coated with PHA including a monomer unit of various structures having a substituent in a side chain, and is extremely useful as highly functional microcapsules. Now the present invention will be detailedly explained in the following.

<Microcapsules>

The term "microcapsule" used in the present specification completely includes the general concept in the drug delivery system (DDS) or in polymer chemistry, but is not necessarily equivalent thereto. Under scanning electron microscopy observation, the "microcapsules" in the appended claims and the specification have various shapes, such as raspberries or a candy having thorns (known as confeito in Portuguese) having many projections, discs like an erythrocyte, rotary oval bodies like a rugby ball or spindle body like *E. coli*. The "microcapsules" in the present specification also have the properties of microspheres constituting a polymer emulsion or a latex or polymer suspension. In this manner, the term "microcapsules" used in the appended claims and specification of the present application is not necessary equivalent to the concept generally used in the drug delivery system (DDS) or in the polymer chemistry, but is used conveniently to refer to the essential "configuration" of the heteropolymer system of the present invention.

For example, the relationship between the inclusion in solid, liquid or gas phase and the solid substrate PHA in the microcapsules of the present invention includes:

(1) Monolithic type consisting of a single mixed phase in which at least one inclusion substance in solid, liquid or gas phase is dispersed and mixed in PHA constituting the solid substrate of the microspheres; and (2) Reservoir type consisting of two phases, namely an external thin PHA film (coating layer) and an interior containing at least one substance in solid, liquid or gas phase.

In the present invention, the configuration 2) is preferred from the standpoint of including a large amount of inclusion in the microcapsules. For example, when a liquid is contained, the liquid can be oil and/or water, and it is possible for one capsule contains a mixture of water and oil in it. "Oil (oil phase)" and "water (water phase)" respectively designate "a substance having properties of oil phase" and "a substance having properties of water phase" in an emulsion. Non-restrictive examples of the oil phase component that can form an emulsion with water and can be suitably used in the present invention to hold a drug etc. include vegetable oils such as soybean oil, sesame oil, cotton seed oil, olive oil, safflower oil, corn oil, or peanut oil, medium-chain fatty acid triglyceride (for example triglycerides of fatty acid with 6 to 12 carbon atoms such as caprylic acid, capric acid or lauric acid (e.g., Panasate 800, 810, 1000 or 1200 manufactured by Nippon Yushi Co.) and liquid hydrocarbons such as liquid paraffin, squalene or squalane. When microencapsulation is carried out by dissolving PHA in the oil phase including the oil phase in the microcapsules, an oil phase capable of dissolving PHA is used as explained later. For forming water phase, there can be employed aqueous solvent principally based on water. The microcapsules of desired functions can be obtained by dissolving desired substances in these phases.

The microcapsules of the present invention can be small spherical microcapsules of a diameter within a range of 1 to 10 μm.

Also in case of holding the drug or the like as a solid substance, there can also advantageously be utilized monolithic particulate construct (microspheres). For example, the mutual relationship between the drug (A) to be included in the slow releasing preparation of the particulate construct of the present invention and PHA (B) includes, for example, the following configurations 1) to 4):

1) a configuration of microcapsules having a core/shell structure in which the drug (A) is contained in a single core portion and PHA (B) is included in the shell;

2) a configuration of microcapsules having a core/shell structure in which the drug (A) is contained in plural core portions and PHA (B) is included in the shell;

3) a configuration of microcapsules having a core/shell structure in which the drug (A) is contained in plural island portions and PHA (B) is included in a ocean-like portion; and 4) a configuration having a micro phase separated structure in which the drug (A) and PHA (B) are mutually dissolved.

In these configurations, the core portion may be comprised of the drug only or a combination with other components, and the shell portion may be comprised of the PHA only or a combination with other components.

The particulate construct of the present invention includes, for example, a microspherical preparation having a diameter in a range of 10 to 100 nm (nanometers), composed of a composition at least including an effective drug and PHA. From the standpoint of self-emulsifiability, there is preferably employed a sub micron size (average particle size not exceeding 1 μm).

Also the hollow particulate construct of the present invention comprises an outer particle-forming portion containing PHA and an inner hollow portion, wherein a partition wall portion consisting of PHA and the hollow portion may be mixed in the interior. Such configuration includes, for example, 1) monolithic hollow particles composed of fine particles of PHA and basically of a single phase in which the hollow portions are dispersed or scattered in PHA (also called microspheres), and 2) hollow microcapsules of reservoir type consisting of clearly divided two phases of outer and inner portions, that is, an external thin film containing PHA (coat or shell) and an inside hollow portion (core) enclosed and protected by the shell.

The "hollow particulate construct" of the present invention can be comprised, for example, of a micro spherical fine particles having a diameter in a range of 1 to 10 μm, of which the external covering is composed of a composition at least containing PHA.

Also the configuration of the PHA-containing shell and the hollow portion in the hollow particulate construct of the present invention, more specifically, the relationship between the bubble (A) and PHA (B), includes the following configurations 1) to 4):

1) a configuration of microcapsules having a core/shell structure in which the bubble (A) is contained in a single core portion and PHA (B) is included in the shell;
2) a configuration of microcapsules having a core/shell structure in which the bubble (A) is contained in plural core portions and PHA (B) is included in the shell;
3) a configuration of microcapsules having a core/shell structure in which the bubble (A) is contained in plural island portions and PHA (B) is included in a sea portion; and
4) a configuration having a micro phase separated structure in which the bubble (A) and PHA (B) are intermixed.

In these configurations, the core portion may be comprised of the bubble only or a combination with other components, and the shell portion may be comprised of the PHA only or a combination with other components.

The particulate construct of the present invention may also be featured in that the monomer unit composition of polyhydroxyalkanoate changes in the direction from the interior to the exterior of the external covering of the particulate construct.

Also the particulate construct may be featured in that at least a part of polyhydroxyalkanoate is subjected to chemical modification.

For example, polyhydroxyalkanoate subjected to the aforementioned chemical modification can include polyhydroxyalkanoate having a graft chain. Such graft chain can be introduced to an epoxy group to polyhydroxyalkanoate containing a monomer unit at least including an epoxy group. Also the graft chain can be a graft chain composed of a compound having an amino group. For example, the aforementioned compound having amino group is preferably a compound modified with an end amino group. The compound having an amino group at the end can be, for example, at least a polymer selected from polyvinyl amine, polyethylene imine, and amino end-modified polysiloxane.

The aforementioned chemically modified polyhydroxyalkanoate can be polyhydroxyalkanoate at least partly crosslinked. For example, the aforementioned crosslinked polyhydroxyalkanoate can be executing a crosslinking reaction on an epoxy group to polyhydroxyalkanoate containing a monomer unit having at least an epoxy group. The crosslinking reaction can be done, for example, by at least a method using a diamine compound, succinic anhydride, 2-ethyl-4-methylimidazole, or electron beam irradiation. For example, the aforementioned diamine compound is preferably hexaethylene diamine.

The aforementioned microcapsules can be prepared in general by a w/o/w (water in oil in water) type emulsion method or an o/w (oil in water) type emulsion method.

More specifically, another invention in the present application is a method for producing microcapsules comprised of PHA and at least one substance of solid, liquid or gas, by 1) dissolving PHA in an organic solvent such as chloroform, and emulsifying it by adding an aqueous solution to obtain an w/o emulsion, 2) if necessary charging the emulsion in a large amount of water and emulsifying it to obtain a w/o/w emulsion, and 3) removing the organic solvent by, for example, evaporation under a reduced pressure to precipitate small spherical particles, which are subjected to recovery and drying, if necessary.

Still another invention in the present application is a method for producing microcapsules containing at least one of solid phase, liquid phase and gaseous phase, and PHA, by 1) dissolving PHA in organic solvent such as chloroform, 2) charging such organic phase in a large amount of water and executing emulsification thereby obtaining o/w emulsion, and 3) removing the organic solvent to an extent exceeding solubility of PHA for example evaporation under a reduced pressure to generate precipitate of small spherical shape, which is recovered and dried if necessary.

Still another invention in the present application is a method for producing microcapsules containing at least one of solid phase, liquid phase and gaseous phase, and PHA, by 1) adding aqueous solution containing PHA synthesizing enzyme and 3-hydroxyacyl CoA to organic solvent and executing emulsification thereby obtaining w/o emulsion, and 2) executing PHA synthesizing reaction to generate precipitate of small spherical shape, which is recovered and dried if necessary.

Still another invention in the present application is a method for producing microcapsules containing at least one of solid phase, liquid phase and gaseous phase, and PHA, by 1) adding the aqueous solution to organic solvent and executing emulsification thereby obtaining w/o emulsion, 2) charging such emulsion into a large amount of water containing PHA synthesizing enzyme and 3-hydroxyacyl CoA to obtain a w/o/w emulsion and 3) executing PHA synthesizing reaction to generate precipitate of small spherical shape, which is recovered and dried if necessary.

Still another invention in the present application is a method for producing microcapsules containing at least one of solid phase, liquid phase and gaseous phase, and PHA, by 1) adding aqueous solution containing PHA synthesizing enzyme and 3-hydroxyacyl CoA to organic solvent and executing emulsification thereby obtaining w/o emulsion, charging such emulsion into a large amount of water containing PHA synthesizing enzyme and 3-hydroxyacyl CoA and executing emulsification to obtain a w/o/w emulsion and 3) executing PHA synthesizing reaction to generate precipitate of small spherical shape, which is recovered and dried if necessary.

Still another invention in the present application is a method for producing microcapsules containing at least one of solid phase, liquid phase and gaseous phase, and PHA, by 1) adding aqueous solution containing PHA synthesizing enzyme and 3-hydroxyacyl CoA to organic solvent and executing emulsification thereby obtaining w/o emulsion, charging such emulsion into a large amount of water and executing emulsification to obtain a w/o/w emulsion and 3) executing PHA synthesizing reaction to generate precipitate of small spherical shape, which is recovered and dried if necessary.

Still another invention in the present application is a method for producing microcapsules containing at least one of solid phase, liquid phase and gaseous phase, and PHA, by 1) charging organic solvent to a large amount of water containing PHA synthesizing enzyme and 3-hydroxyacyl CoA and executing emulsification to obtain o/w emulsion and 2) executing PHA synthesizing reaction to generate precipitate of small spherical shape, which is recovered and dried if necessary.

<Examples of PHA and Producing Method thereof>

PHA usable in the present invention may contain at least monomer units represented by the following chemical formulae [1] to [10].

$$\begin{array}{c} \text{R1} \\ | \\ (\text{CH}_2)a \\ | \\ -(\text{O}-\text{CH}-\text{CH}_2-\text{CO})- \end{array} \quad [1]$$

wherein R1 and a are selected from the group of combinations consisting of:

(1) R1 is a hydrogen atom (H) and a is any of integers from 3 to 10;

(2) R1 is a halogen atom and a is any of integers from 1 to 10;

(3) R1 is a chromophore and a is any of integers from 1 to 10;

(4) R1 is a carboxyl group or a salt thereof and a is any of integers from 1 to 10; and (5) R1 is $$-\underset{H}{\overset{O}{\underset{|}{C}}}-\text{CH}_2$$

and a is any of integers from 1 to 7.

$$\begin{array}{c} \text{R2} \\ \diagup\!\!\!\diagdown \\ \text{CH}_2 \\ | \\ (\text{CH}_2)b \\ | \\ -(\text{O}-\text{CH}-\text{CH}_2-\text{CO})- \end{array} \quad [2]$$

wherein b represents any of integers from 0 to 7 and R2 represents any one selected from the group consisting of hydrogen atom (H), halogen atoms, —CN, —NO$_2$, —CF$_3$, —C$_2$F$_5$, and —C$_3$F$_7$.

$$\begin{array}{c} \text{R3} \\ \diagup\!\!\!\diagdown \\ \text{O} \\ | \\ (\text{CH}_2)c \\ | \\ -(\text{O}-\text{CH}-\text{CH}_2-\text{CO})- \end{array} \quad [3]$$

wherein c represents any of integers from 1 to 8 and R3 represents any one selected from the group consisting of hydrogen atom (H), halogen atoms, —CN, —NO$_2$, —CF$_3$, —C$_2$F$_5$, and —C$_3$F$_7$.

$$\begin{array}{c} \text{R4} \\ \bigcirc \\ | \\ \text{CH}_2 \\ | \\ (\text{CH}_2)d \\ | \\ -(\text{O}-\text{CH}-\text{CH}_2-\text{CO})- \end{array} \quad [4]$$

wherein d represents any of integers from 0 to 7 and R4 represents any one selected from the group consisting of hydrogen atom (H), halogen atoms, —CN, —NO$_2$, —CF$_3$, —C$_2$F$_5$, and —C$_3$F$_7$.

$$\begin{array}{c} \text{R5} \\ \diagup\!\!\!\diagdown \\ \text{CO} \\ | \\ (\text{CH}_2)e \\ | \\ -(\text{O}-\text{CH}-\text{CH}_2-\text{CO})- \end{array} \quad [5]$$

wherein e represents any of integers from 1 to 8 and R5 represents any one selected from the group consisting of hydrogen atom (H), halogen atoms, —CN, —NO$_2$, —CF$_3$, —C$_2$F$_5$, —C$_3$F$_7$, —CH$_3$, —C$_2$H$_5$, and —C$_3$H$_7$.

$$\begin{array}{c} \diagup\!\!\!S\!\!\!\diagdown \\ | \\ \text{CH}_2 \\ | \\ (\text{CH}_2)f \\ | \\ -(\text{O}-\text{CH}-\text{CH}_2-\text{CO})- \end{array} \quad [6]$$

wherein f represents any of integers from 0 to $$\begin{array}{c} \diagup\!\!\!S\!\!\!\diagdown \\ | \\ \text{CO} \\ | \\ (\text{CH}_2)g \\ | \\ -(\text{O}-\text{CH}-\text{CH}_2-\text{CO})- \end{array} \quad [7]$$

wherein g represents any of integers from 1 to 8.

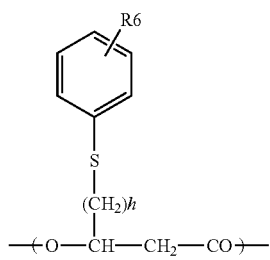

[8]

wherein h represents any of integers from 1 to 7 and R6 represents any one selected from the group consisting of hydrogen atom (H), halogen atoms, —CN, —NO$_2$, —COOR', —SO$_2$R", —CH$_3$, —C$_2$H$_5$, —C$_3$H$_7$, —CH(CH$_3$)$_2$, and —C(CH$_3$)$_3$, wherein R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$.

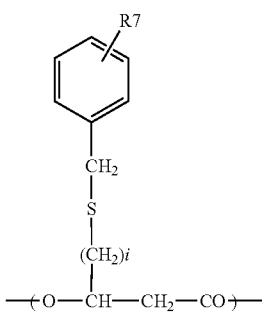

[9]

wherein i represents any of integers from 1 to 7 and R7 represents any one selected from the group consisting of hydrogen atom (H), halogen atoms, —CN, —NO$_2$, —COOR', —SO$_2$R", in which R' is selected from the group consisting of hydrogen atom (H), Na, K, —CH$_3$, and —C$_2$H$_5$, and R" is selected from the group consisting of —OH, —ONa, —OK, halogen atoms, —OCH$_3$, and —OC$_2$H$_5$.

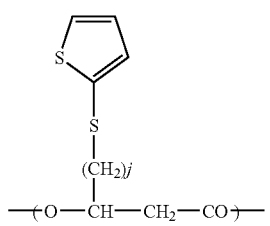

[10]

wherein j represents any of integers from 1 to 9.

In the present invention, the PHA is polyester resin having 3-hydroxyalkanoate as a monomer unit. If it is produced by a microorganism, such polyester resin is generally isotactic polymer comprised of R bodies alone, but such isotactic polymer is not essential, as long as the objects of the present invention can be attained in both the physical properties and functions, and there can also be utilized atactic polymers. PHA can also be obtained by chemical synthesis doing ring-opening polymerization of a lactone compound with an organometallic catalyst (for example an organic catalyst containing aluminum, zinc or tin).

Also when PHA is synthesized utilizing 3- hydroxyacyl CoA and PHA synthesizing enzyme in combination with the preparation of w/o, w/o/w or o/w emulsion, it can be any PHA synthesizable by the PHA synthesizing enzyme. As explained above, PHA synthesizing enzyme catalyzes the last stage of the PHA synthesizing reaction system in the living organism, and any PHA known to be synthesizable in the living organism is therefore synthesized by the catalytic action of such enzyme. Consequently, it is possible to prepare microcapsules in which at least one of solid phase, liquid phase and gaseous phase is included or coated by PHA of any kind known to be synthesized in the living organism from 3-hydroxyacyl CoA corresponding to the desired PHA by using the PHA synthesizsing enzyme.

Also in the present invention, in the side-chain structures R1 to R7, there can be selected one or more atoms or functional groups selected from a group consisting of various atoms and functional groups. Also as to the substituting positions of R2 to R7, there can be obtained PHA comprised of the corresponding monomer unit in the ortho, meta or para position, but, if there is no large difference in the functionality or physical properties in these isomers, advantageously employed is a metha- or para-substituted isomer in consideration of the yield or ease of intake into the polymer.

In the above formulas 1 to 10, halogen atoms can be fluorine, chlorine, or bromine. The chromophores are not particularly limited as long as the 3-hydroxyacyl CoA having the chromophore is catalyzed by PHA synthetase, but it is preferable that a methylene chain of 1 to 5 carbon atoms is present between the chromophore and the carboxyl group to which CoA is bonded, in view of steric hindrance at the time of polymer synthesis. When the light absorption wavelength of the chromophore is within a visible range, a colored construct can be obtained and when the light absorption wavelength is outside the visible range, the construct may be used as various electronic materials. Such chromophores include nitroso, nitro, azo, diarylmethane, triarylmethane, xanthene, acridine, quinoline, methine, thiazole, indamine, indophenol, lactone, aminoketone, hydroxyketone, stilbene, azine, oxazine, thiazine, anthraquinone, phthalocyanine, and indigoid.

As PHA which is used for the present invention, random copolymers or block copolymers which include a plurality of the above described monomer units can be used. Therefore, it becomes possible to control physical properties of PHA and add some functions to the PHA by utilizing properties of each monomer unit or functional groups included therein, and also possible to manifest new functions obtained by utilizing interaction between functional groups.

It is also possible, by suitably controlling the addition amounts of the monomer compounds and the addtion order thereof, to synthesize a block copolymer having an arbitrary order and an arbitrary composition ratio. Also, if necessary, chemical modification or the like may be applied after or in the course of synthesis of PHA.

Further, it is possible to change a monomer unit composition of the PHA in a radial direction in the case where a shape of the construct is like a particle and in a vertical direction in the case where a shape of the construct is like a plate, by changing the composition with time through alteration of kinds and concentrations of 3-hydroxyacyl CoA which is a base material.

By suitably selecting PHA on the surfacial layer of the microcapsules and that on the internal layer thereof, it is possible to further enhance the effects of the present invention, for example functions of holding liquid or gas, control of slow releases and self dispersibility in aqueous solution. More specifically, by suitably selecting the monomer units of PHA, it is possible to change PHA along a direction from inside to outside of the microcapsule, to form, for example, a multi-layered structure or a gradient structure.

Also by introducing a graft chain to PHA on the surface layer of the microcapsules, it is possible to exhibit functionalities based on such graft chain, for example functions to hold liquid or gas, control of slow releases and self dispersibility in aqueous solution. Also by crosslinking PHA on the surface layer of the microcapsules, improvement is possible in functions to hold liquid or gas, mechanical strength of the microcapsules and control of slow releases.

In the production of PHA of the present invention by in vivo synthesis or in vitro synthesis, the aforementioned various monomer units may be contained, of which number should be suitably selected in consideration of the functionalities and the physical properties of the desired polymer. In general, incorporation of 6 kinds of monomers or less is expected to be sufficient to attain the objects of the present invention, but more can be used when delicate control of the functionalities and physical properties is desired.

The PHA employed in the microcapsules of the present invention, synthesized by PHA producing microorganisms or in vitro by the PHA synthesizing enzyme is generally isotactic polymer comprised of R bodies alone.

In the present invention, PHA of such desired physical properties can be obtained by selecting the culture conditions of the microorganisms capable of synthesizing PHA. For example, control of the culture time etc. allows to control the number-average molecular weight. Also elimination of low molecular weight components by solvent extraction or reprecipitation allows control of the number-averaged molecular weight. Also in in vitro synthesis, various physical properties can be controlled by suitably selecting the composition of reaction solution and the reaction time.

The number averaged molecular weight of PHA is desirably within a range of about 1,000 to 10 million, preferably about 5,000 to a million. Also the dispersion (weight average molecular weight/number average molecular weight) of PHA is preferably within a range of 1 to 10, more preferably 1 to 5.

For the microcapsules, for example, those including liquid, liquid-holding function, slow releasing function and self-dispersibility in an aqueous solution are important features. The microcapsules of the present invention are most featured in satisfying these requirements. More specifically, the liquid-holding function, slow releasing function and the self-dispersibility in an aqueous solution can be controlled by controlling the kind/composition ratio/molecular weight/crystallinity of the monomer units of PHA as explained above.

Also in case of a slow releasing preparation including a drug, particularly a water-soluble drug, control of both of the initial releasing rate and subsequent releasing rate is important in controlling the release characteristics. The microcapsules of the present invention are most featured in satisfying these requirements. More specifically, the initial release amount of the drug can be controlled by controlling the kind/composition ratio/molecular weight/crystallinity of the monomer units of PHA as explained above, and the drug releasing period can also be controlled by controlling the kind/composition ratio/molecular weight/crystallinity of the monomer units of PHA. Also the slow releasing preparation of the present invention is not limited to a slow releasing preparation having zero-order release rate but can also be designed to have an arbitrarily high initial release amount or as a slow releasing preparation having a time lag in drug release, and therefore has an extremely wide application range.

Further, in case of a slow releasing preparation including a drug, particularly a substantially water-insoluble drug, control of both of the initial releasing rate and subsequent releasing rate is important in controlling the release characteristics. The microcapsules of the present invention are most featured in satisfying these requirements. More specifically, the initial release amount of the drug can be controlled by controlling the kind/composition ratio/molecular weight/crystallinity of the monomer units of PHA as explained above, and the drug releasing period can also be controlled by controlling the kind/composition ratio/molecular weight/crystallinity of the monomer units of PHA. Also the slow releasing preparation of the present invention is not limited to a slow releasing preparation having zero-order release rate but can also be designed to have an arbitrarily high initial release amount or as a slow releasing preparation having a time lag in drug release, and therefore has an extremely wide application range.

Also in case of utilization as an ultrasonic contrast medium, the bubble amount contained in the hollow particular construct and the holding function for such bubble are both important. The ultrasonic contrast medium of the present invention is most featured in utilizing the hollow particulate construct of the present invention as an ultrasonic contrast medium. More specifically, the bubble holding function can be controlled by controlling the kind/composition ratio/molecular weight/crystallinity of the monomer units of PHA as explained above.

The specific method of PHA production by microorganisms is to culture microorganisms that can produce PHA containing at least one of the monomer units of the formulae (1) to (10) from alkanoic acids corresponding to these monomer units, in a culture medium containing such alkanoic acids. The microorganism capable of producing PHA of the present invention can be one suitably selected from the microorganism capable of producing PHA or a transformant into which the gene of PHA synthesizing enzyme of such microorganisms are introduced. The culturing method will be explained later.

For example, by culturing a microorganism capable of producing polyhydroxyalkanoate containing 3-hydroxy-5-(4-fluorophenyl) valeric acid (3-HFPV) monomer unit represented by the following formula [21] from 5-(4-fluorophenyl) valeric acid (FPVA) represented by the following formula [22], it is possible to produce polyhydroxyalkanoate containing the 3HFPV monomer unit:

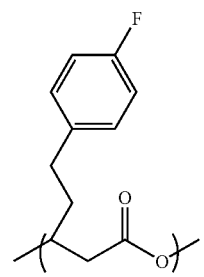

[21]

-continued

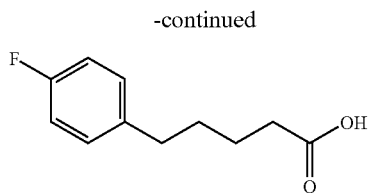
[22]

Also, by culturing a microorganism capable of producing polyhydroxyalkanoate containing a 3-hydroxy-4-phenoxy butyric acid (3-HPxB) monomer unit represented by the following formula [23] from 4-phyenoxy butyric acid (PxBA) represented by the following formula [24], it is possible to produce polyhydroxyalkanoate containing the 3HPxB monomer unit:

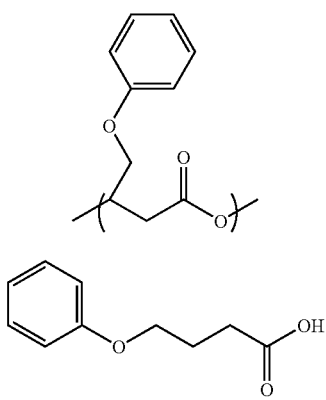
[23]

[24]

Also, by culturing a microorganism capable of producing polyhydroxyalkanoate containing a 3-hydroxy-4-cyclohexyl butyric acid (3-HCHB) monomer unit represented by the following formula [25] from 4-cyclohexyl butyric acid (CHBA) represented by the following formula [26], it is possible to produce polyhydroxyalkanoate containing the 3HCHB monomer unit:

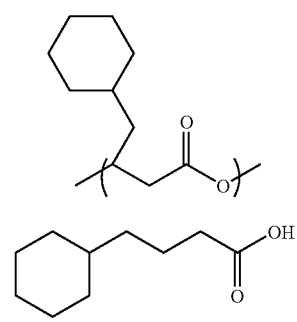
[25]

[26]

Also, by culturing a microorganism capable of producing polyhydroxyalkanoate containing a 3-hydroxy-5-benzoyl valeric acid (3-HBzV) monomer unit represented by the following formula [27] from 5-benzoyl valeric acid (BZVA) represented by the following formula [28], it is possible to produce polyhydroxyalkanoate containing the 3HBzV monomer unit:

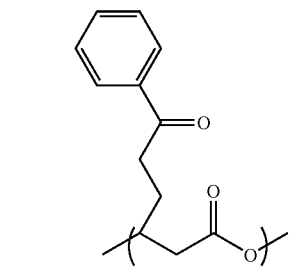
[27]

[28]

Also, by culturing a microorganism capable of producing polyhydroxyalkanoate containing a 3-hydroxy-5-(4-fluorobenzyol) valeric acid (3-HFBzV) monomer unit represented by the following formula [29] from 5-(4-fluorobenzyol) valeric acid (FBZVA) represented by the following formula [30], it is possible to produce polyhydroxyalkanoate containing the 3HFBzV monomer unit:

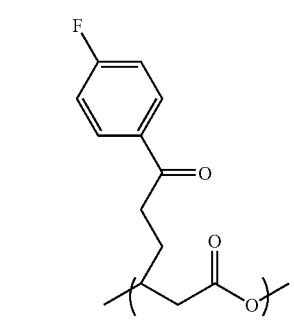
[29]

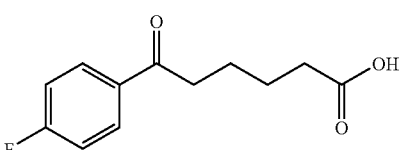
[30]

Also, by culturing a microorganism capable of producing polyhydroxyalkanoate containing a 3-hydroxy-5-thienyl valeric acid (3HTV) monomer unit represented by the following formula [31] from 5-thienyl valeric acid (TVA) represented by the following formula [32], it is possible to produce polyhydroxyalkanoate containing the 3HTV monomer unit:

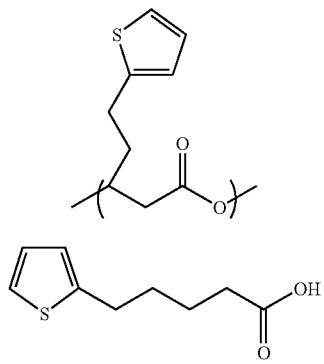

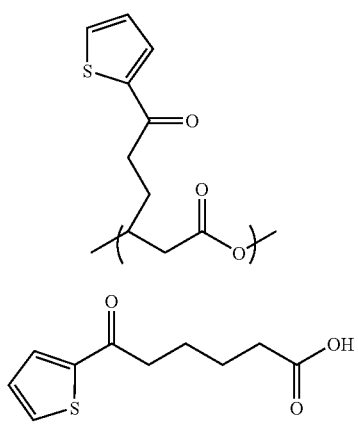

Also, by culturing a microorganism capable of producing polyhydroxyalkanoate containing a 3-hydroxy-5-thienoyl valeric acid (3HToV) monomer unit represented by the following formula [33] from 5-thienoyl valeric acid (TOVA) represented by the following formula [34], it is possible to produce polyhydroxyalkanoate containing the 3HToV monomer unit:

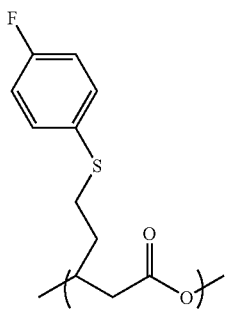

Also, by culturing a microorganism capable of producing polyhydroxyalkanoate containing a 3-hydroxy-5-(4-fluorothiophenoxy) valeric acid (3HTPxV) monomer unit represented by the following formula [35] from 5-(4-fluorothiophenoxy) valeric acid (FTPxVA) represented by the following formula [36], it is possible to produce polyhydroxyalkanoate containing the 3HFTPxV monomer unit:

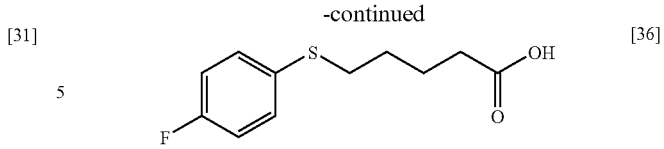

Also, by culturing a microorganism capable of producing polyhydroxyalkanoate containing a 3-hydroxy-5-[(4-fluorophenylmethyl)sulfanyl] valeric acid monomer unit represented by the following formula [37] from 5-[(4-fluorophenylmethyl)sulfanyl] valeric acid represented by the following formula [38], it is possible to produce polyhydroxyalkanoate containing the 3-hydroxy-5-[(4-fluorophenylmethyl)sulfanyl] valeric acid monomer unit:

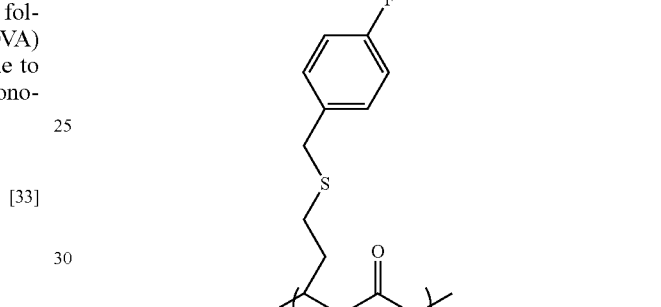

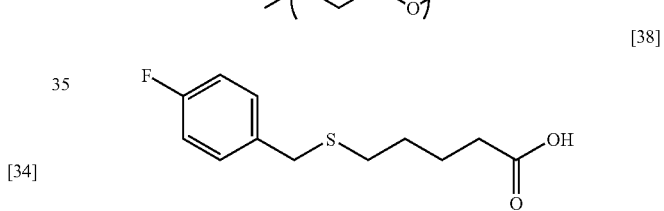

Also, by culturing a microorganism capable of producing polyhydroxyalkanoate containing a 3-hydroxy-5-thiothienoxy valeric acid (3HTTxV) monomer unit represented by the following formula [39] from 5-thiothienoxy valeric acid (FTxVA) represented by the following formula [40], it is possible to produce polyhydroxyalkanoate containing the 3HTTxV monomer unit:

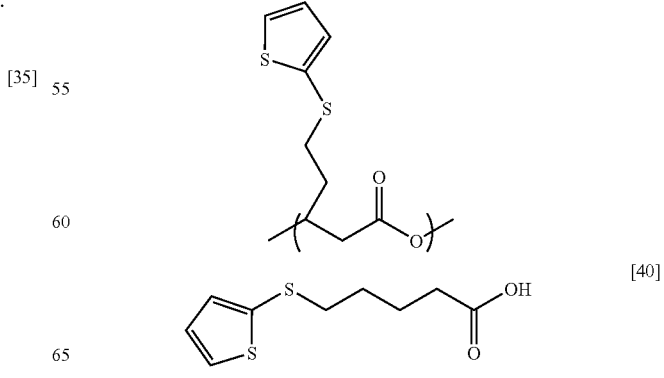

Also, by culturing a microorganism capable of producing polyhydroxyalkanoate containing a 3-hydroxy-octanoic acid (3HO) monomer unit represented by the following formula [41] from octanic acid (OA) represented by the following formula [42], it is possible to produce polyhydroxyalkanoate containing the 3HO monomer unit:

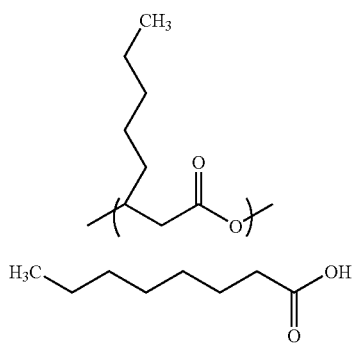

[41]

[42]

Also, by culturing a microorganism capable of producing polyhydroxyalkanoate containing a 3-hydroxy-7,8-epoxy octanoic acid monomer unit represented by the following formula [43] from octene acid represented by the following formula [44], it is possible to produce polyhydroxyalkanoate containing the 3-hydroxy-7,8-epoxy octanoic acid monomer unit:

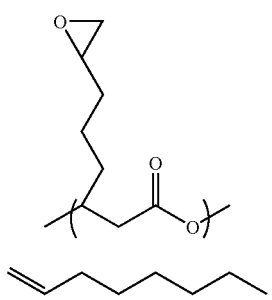

[43]

[44]

<Microorganisms>

The microorganism to be employed in the method of the present invention can be any microorganism capable of producing PHA including at least one of the units represented by the chemical formulae (1)~(10) by culture in a culture medium containing the corresponding alkanoic acid.

The microorganism for synthesizing PHA can be PHB or PHB/V producing bacteria, and such microorganism includes not only those of *Aeromonas* sp., *Comamonas* sp., *Methylobacterium* sp., *Paracoccus* sp. and *Pseudomonas* sp. but also *Burkholderia* sp. cepacia KK01 strain, *Ralstonia eutropha* TB64 strain and *Alcaligenes* sp. TL2 strain separated by the present inventors. The strains KK01, TB64 and TL2 have been deposited under the respective accession numbers: FERM BP-4235, FERM BP-6933 and FERM BP-6913 in International Patent Organism Depositary of Institute of Advanced Industrial Science and Technology, Agency of Industrial Science and Technology.

For example, mcl-PHA- or unusual-PHA-producing microorganisms can be used as the PHA synthetase-producing microorganism. Such microorganisms include, in addition to the above described *Pseudomonas oleovorans*, *Pseudomonas resinovorans*, *Pseudomonas* sp. strain 61-3, *Pseudomonas putida* KT 2442, and *Pseudomonas aeruginosa*, strains of *Pseudomonas* sp. such as *Pseudomonas putida* P91, *Pseudomonas cichorii* H45, *Pseudomonas cichorii* YN2, and *Pseudomonas jessenii* P161 all of which were isolated by the inventors, strains belonging to Burkholderia sp. such as Burkholderia sp. OK3, FERM P-17370 described in Japanese Patent Application Laid-Open No. 2001-78753 and *Burkholderia* sp. OK4, FERM P-17371 described in Japanese Patent Application Laid-Open No. 2001-69968. In addition to the above-described microorganisms, it is possible to use microorganisms of genus *Aeromonas* and *Comamonas* that can produce mcl-PHA and unusual-PHA.

Strains P91, H45, YN2 and P161 have been deposited (accession number: FERM BP-7373, FERM BP-7374, FERM BP-7375, and FERM BP-7376 respectively) in International Patent Organism Depositary of Institute of Advanced Industrial Science and Technology (former National Institute of Bioscience and Human Technology, Agency of Industrial Science and Technology), 1-3, Higashi 1-chome, Tsukuba-shi, Ibaraki-ken, 305-0046, Japan, under the Budapest Treaty on the International Recognition of the Deposit of Microorganism for the Purpose of Patent Procedure.

Microbiological properties of the above described P91, H45, YN2 and P161 are as follows. As for the strain P161, the base sequence of 16S rRNA is as SEQ ID NO: 1.

*Pseudomonas putida* P91

(1) Morphology

Form and size of the cell: rod, 0.6 μm×1.5 μm

Polymorphism of the cell: –

Mobility: +

Spore formation: –

Gram stain: negative

Colony shape: circular, smooth edge, low convex, smooth surface, lustrous, cream color (2) Physiological Properties Catalase: positive Oxidase: positive O/F test: oxidizing type Reduction of nitrate: negative Production of indole: negative Acidification of glucose: negative Arginine dihydrolase: positive Urease: negative Esculin hydrolysis: negative Gelatin hydrolysis: negative β-galactosidase: negative Fluorescent dye production on King's B agar: positive (3) Substrate Assimilation Glucose: positive L-arabinose: negative D-mannose: negative D-mannitol: negative N-acetyl-D-glucosamine: negative Maltose: negative Potassium gluconate: positive n-capric acid: positive Adipic acid: negative dl-malic acid: positive Sodium citrate: positive Phenyl acetate: positive

*Pseudomonas cichorii* H45

(1) Morphology
Form and size of the cell: rod, 0.8 μm×1.0 to 1.2 μm
Polymorphism of the cell: −
Mobility: +
Spore formation: −
Gram stain: negative
Colony shape: circular, smooth edge, low convex, smooth surface, lustrous, cream color (2) Physiological Properties
Catalase: positive
Oxidase: positive
O/F test: oxidizing type
Reduction of nitrate: negative
Production of indole: negative
Acidification of glucose: negative
Arginine dihydrolase: negative
Urease: negative
Esculin hydrolysis: negative
Gelatin hydrolysis: negative
β-galactosidase: negative
Fluorescent dye production on King's B agar: positive
Growth in 4% NaCl: negative
Accumulation of poly-β-hydroxybutyric acid: negative (3) Substrate Assimilation
Glucose: positive
L-arabinose: negative
D-mannose: positive
D-mannitol: positive
N-acetyl-D-glucosamine: positive
Maltose: negative
Potassium gluconate: positive
n-capric acid: positive
Adipic acid: negative
dl-malic acid: positive
Sodium citrate: positive
Phenyl acetate: positive

*Pseudomonas cichorii* YN2

(1) Morphology
Form and size of the cell: rod, 0.8 μm×1.5 to 2.0 μm
Polymorphism of the cell: −
Mobility: +
Spore formation: −
Gram stain: negative
Colony shape: circular, smooth edge, low convex, smooth surface, lustrous, translucent (2) Physiological Properties
Catalase: positive
Oxidase: positive
O/F test: oxidizing type
Reduction of nitrate: negative
Production of indole: positive
Acidification of glucose: negative
Arginine dihydrolase: negative
Gelatin hydrolysis: negative
β-galactosidase: negative
Fluorescent dye production on King's B agar: positive
Growth in 4% NaCl: positive (weakly growth)
Accumulation of poly-β-hydroxybutyric acid: negative
Hydrolysis of Tween 80: positive (3) Substrate Assimilation
Glucose: positive
L-arabinose: positive
D-mannose: negative
D-mannitol: negative
N-acetyl-D-glucosamine: negative
Maltose: negative
Potassium gluconate: positive
n-capric acid: positive
Adipic acid: negative
dl-malic acid: positive
Sodium citrate: positive
Phenyl acetate: positive

*Pseudomonas jessenii* P161

(1) Morphology
Form and size of the cell: spherical: φ 0.6 μm, rod: 0.6 μm×1.5 to 2.0 μm
Polymorphism of the cell: +(elongation)
Mobility: +
Spore formation: −
Gram stain: negative
Colony shape: circular, smooth edge, low convex, smooth surface, pale yellow (2) Physiological Properties
Catalase: positive
Oxidase: positive
O/F test: oxidizing type
Reduction of nitrate: positive
Production of indole: negative
Arginine dihydrolase: positive
Urease: negative
Esculin hydrolysis: negative
Gelatin hydrolysis: negative
β-galactosidase: negative
Fluorescent dye production on King's B agar: positive (3) Substrate Assimilation
Glucose: positive
L-arabinose: positive
D-mannose: positive
D-mannitol: positive
N-acetyl-D-glucosamine: positive
Maltose: negative
Potassium gluconate: positive
n-capric acid: positive
Adipic acid: negative
dl-malic acid: positive
Sodium citrate: positive
Phenyl acetate: positive For routine culture of the PHA synthetase-producing microorganisms, for example, to prepare cell stocks, to obtain sufficient cells for enzyme production or to maintain active state of the cells, one can select suitable culture medium containing ingredients necessary for the growth of microorganisms. Any culture medium can be used as long as it does not interfere microbial growth or vitality, including common natural media such as nutrient broth and yeast extracts, and synthetic media supplemented with nutrients.

The culture conditions such as temperature, aeration and agitation are suitably selected according to the microorganism to be used.

On the other hand, in case of causing the aforementioned PHA producing microorganisms to produce PHA including the desired 3-hydroxy-alkanoic acid unit, there can be employed for example an inorganic culture medium containing at least a carbon source for proliferation of the microorganisms in addition to the alkanoic acid corresponding to the monomer unit, as the raw material for producing PHA. The initial content of the raw material alkanoic acid is preferably selected within a range of 0.01 to 1%(w/v), more preferably 0.02 to 0.2%(w/v). The raw material alkanoic acid does not necessarily has satisfactory solubility in water but may remain in a suspended state in the use of the aforementioned microorganisms in the present invention.

In order to improve the solubility of alkanoic acid in the culture medium, it is also possible to add the alkanoic acid to the culture medium in a state dissolved or finely suspended in solvent such as 1-hexadecene or n-hexadecane. In such case, the concentration of the solvent such as 1-hexadecene or n-hexadecane should not exceed 3%(v/v).

A proliferation substrate, to be utilized for proliferation of the microorganisms, is preferably added separately to the culture medium. For such proliferation substrate, there can be used nutrition source such as enzyme extract, polypeptone or meat extract. Also, in consideration of the effectiveness as the proliferation substrate according to the strain to be used, there can be suitably selected sugars, organic acids generated as intermediate products in the TCA pathway or generated by a biochemical reaction of one or two steps from the TCA pathway or salts thereof, amino acids or salts thereof. Also if the proportion of the desired monomer can be low, there can be employed straight-chain alkanoic acids with 4 to 12 carbon atoms or salts thereof. In such case, however, it is to be considered that the proportion of a simple straight-chain monomer without substituent becomes high.

Among these substrates, as the sugar, there can be advantageously utilized one or more compounds selected from aldoses such as glyceroaldehyde, erythrol, arabinose, xylose, glucose, galactose, mannose or fructose, alditols such as glycerol, erythritol or xylitol; alditols such as glycerol, erythritol or xylitol; aldonic acids such as gluconic acid; uronic acids such as glucronic acid or galacturonic acid, and disaccharides such as maltose, sucrose or lactose.

Also as organic acid or salt thereof, there can be advantageously utilized one or more compounds selected from a group consisting of piruvic acid, oxaloaccetic acid, citric acid, isocitric acid, chetoglutaric acid, succinic acid, fumalic acid, malic acid, lactic acid and salts thereof.

Also as amino acid or salts thereof, there can be advantageously utilized one or more compounds selected from a group consisting of glutamic acid, aspartic acid and salts thereof.

Among these various proliferation substrates, there are preferred polypeptone and sugars. The content of such proliferation substrate in the culture medium is preferably selected within a range of 0.1 to 5%(w/v), more preferably 0.2 to 2%(w/v).

In the culture method for causing the microorganisms to produce and accumulate PHA, the productivity may further increase, after sufficient proliferation, by transferring the bacteria to a culture medium in which the nitrogen source such as ammonium chloride is limited and executing further culture in a state including the compound constituting the substrate of the desired unit. For example there can be employed a multi-step method by connecting plural steps of different culture conditions.

The culture temperature can be any temperature at which the aforementioned strains can satisfactorily proliferate, and can be within a range of 15 to 40° C., preferably 20 to 35° C., more preferably 20 to 30° C.

The culture can be executed in any culture method such as liquid culture or solid culture, in which the employed microorganisms can proliferate and can produce, from the starting alkanoic acid contained in the culture medium. Also there may be employed any of batch culture, fed batch culture, semi-continuous culture or continuous culture as long as the raw material, proliferating substrate and oxygen can be appropriately supplied. For example for liquid batch culture, there can be employed oxygen supply method by vibration in a vibrating flask or by agitated aeration in a jar fermenter.

Any inorganic culture medium can be used for the above described culture process as long as the medium contains ingredients such as phosphorus source (phosphate etc.), and nitrogen source (ammonium salt, nitrate etc.) to support microbial growth. Therefore, MSB medium, E medium (J. Biol. Chem., 218, 97-106 (1956)), or M9 medium can be used as the inorganic salt medium, for example. Composition of M9 medium which is used in Examples is as follows.

| | |
|---|---|
| $Na_2HPO_4$: | 6.2 g |
| $KH_2PO_4$: | 3.0 g |
| NaCl: | 0.5 g |
| $NH_4Cl$: | 1.0 g |
| (per liter, pH 7.0) | |

In addition, it is preferable to add the stock solution of trace ingredients of the following composition to about 0.3% (v/v), for good proliferation and production of PHA synthetase.
Stock solution of trace ingredients

| | |
|---|---|
| Nitrilotriacetic acid: | 1.5 g |
| $MgSO_4$: | 3.0 g |
| $MnSO_4$: | 0.5 g |
| NaCl: | 1.0 g |
| $FeSO_4$: | 0.1 g |
| $CaCl_2$: | 0.1 g |
| $CoCl_2$: | 0.1 g |
| $ZnSO_4$: | 0.1 g |
| $CuSO_4$: | 0.1 g |
| $AlK(SO_4)_2$: | 0.1 g |
| $H_3BO_3$: | 0.1 g |
| $Na_2MoO_4$: | 0.1 g |
| $NiCl_2$: | 0.1 g |
| (per liter) | |

<Recovery of PHA>

The PHA can be acquired fro the culture liquid by an ordinarily employed method. It is possible to use extraction and purification from the culture liquid in case PHA is secreted i the culture medium, or extraction and purification from the bacteria in case PHA is accumulated in the bacteria. For example, the recovery of PHA from the culture bacteria body of the microorganisms is most simply executed by extraction with organic solvent such as chloroform, but there may also be employed dioxane, tetrahydrdofurane, acetonitrile or acetone. In a situation where the organic solvent is difficult to use, there can be utilized processing with a surfactant such as SDS, processing with an enzyme such as lysozyme, or chemical processing with EDTA, sodium hypochlorite, hydrogen peroxide or ammonia to eliminate the bacteria components other than PHA, thereby recovering PHA alone.

The culture of microorganisms, production of PHA by the microorganisms and accumulation therein, and recovery of PHA from the bacteria are not limited to the methods explained above. For example, the microorganisms to be employed in the PHA producing method of the present invention are not limited to those of the aforementioned four strains but there may also be employed any microorganisms having the PHA producing ability similar to that of these four strains.

<Biosynthesis with Transformant>

It is also possible to produce PHA synthetase by using a transformant to which the PHA synthetase gene of the above PHA producing strain has been introduced. Cloning of the PHA synthetase gene, construction of expression vectors and transformants can be done according to the conventional methods. To culture a transformant obtained using a bacterial host such as *Escherichia coli*, natural media such as LB medium or synthetic media such as M9 medium can be used. Cells are cultured with aeration for 8 to 27 hours at 25 to 37° C. After culture, cells are collected to recover PHA synthetase accumulated in the cells. Antibiotics such as kanamycin, ampicillin, tetracycline, chloramphenicol, and streptomycin may be added to the culture as required. In addition, if the an inducible promoter is used in the expression vector, expression may be promoted by adding a corresponding inducer to the culture medium when the transformant is cultured. Such an inducer may be isopropyl-β-D-thiogalactopyranoside (IPTG), tetracycline, or indoleacrylic acid (IAA).

<3-hydroxyacyl CoA>

Specifically, 3-hydroxyacyl CoA usable as the substrate of PHA synthetase in the present invention is represented by the following chemical formulae [11] to [20].

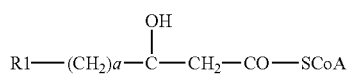

[11]

wherein —SCoA represents coenzyme A bonded to alkanoic acid, and R1 and a are as defined for the above-described chemical formula [1].

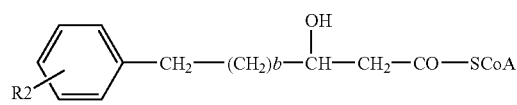

[12]

wherein —SCoA represents coenzyme A bonded to alkanoic acid, R2 and b are as defined for the above-described chemical formula [2],

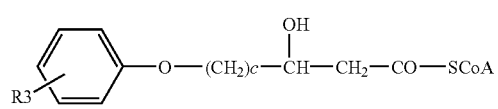

[13]

wherein —SCoA represents coenzyme A bonded to alkanoic acid, R3 and c are as defined for the above-described chemical formula [3].

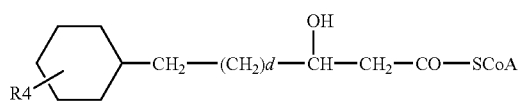

[14]

wherein —SCoA represents coenzyme A bonded to alkanoic acid, R4 and d are as defined for the above-described chemical formula [4].

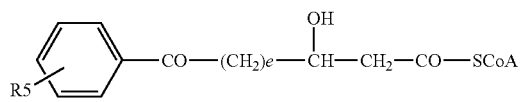

[15]

wherein —SCoA represents coenzyme A bonded to alkanoic acid, R5 and e are as defined for the above-described chemical formula [5].

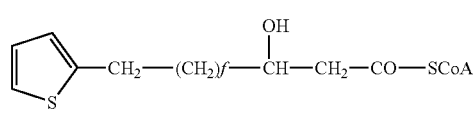

[16]

wherein —SCoA represents coenzyme A bonded to alkanoic acid, and f is as defined for the above-described chemical formula [6].

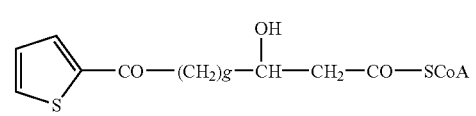

[17]

wherein, —SCoA represents coenzyme A bonded to alkanoic acid, and g represents any of integers from 1 to 8 as defined for the above-described chemical formula [7].

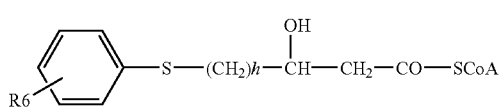

[18]

wherein, —SCoA represents coenzyme A bonded to alkanoic acid, R6 and h are as defined for the above-described chemical formula [8].

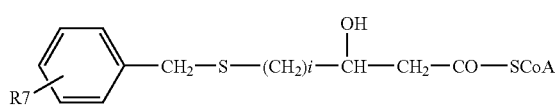

[19]

wherein, —SCoA represents coenzyme A bonded to alkanoic acid, R7 and i are as defined for the above-described chemical formula [9].

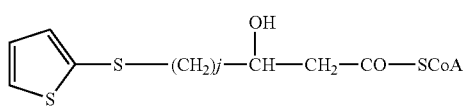 [20]

wherein, —SCoA represents coenzyme A bonded to alkanoic acid, and j represents any of integers from 1 to 9 as defined for the above-described chemical formula [10].

These 3-hydroxyacyl CoAs can be synthesized by a suitable method selected from, for example, in vitro synthesis use an enzyme, in vivo synthesis using living organisms such as microorganisms and plants, and chemical synthesis. Enzymatic synthesis, especially, is commonly used to synthesize these substrates. For example, it is known a method to use a commercially available acyl CoA synthetase (acyl CoA ligase, E. C. 6. 2. 1. 3) to catalyze the following reaction: 3-hydroxyalkanoic acid+CoA to 3-hydroxyacyl CoA (Eur. J. Biochem., 250, 432-439 (1997), Appl. Microbiol. Biotechnol., 54, 37-43 (2000) etc.). The synthesis process using enzyme or organism may be a batch process or a continuous process using immobilized enzyme or cells.

<PHA Synthetase and Production Microorganisms>

The PHA synthetase used in the present invention can be produced by using a microorganism selected from the microorganisms known to produce PHA synthetase, or by using a transformant to which the PHA synthetase gene of such a microorganism has been introduced.

<Acquisition of PHA Synthesizing Enzyme>

For routine culture of the microorganisms to be used for the production of PHA synthesizing enzyme of the present invention, for example, to prepare cell stocks, to obtain sufficient cells for enzyme production or to maintain active state of the cells, one can select suitable culture medium containing ingredients necessary for the proliferation of microorganisms.

Any culture method, such as liquid culture and solid culture, can be used as long as the subject microorganism can proliferate. It may be batch culture, fed-batch culture, semi-continuous culture, or continuous culture. Liquid batch culture includes a method of shaking a culture flask to supply oxygen, and a method using a jar fermenter that supplies oxygen by aeration. A plurality of these processes may be combined as a multistage method.

To produce PHA synthetase by using the above described PHA-producing microorganism, first the microorganism is grown on an inorganic medium containing alkanoic acid such as octanoic acid and nonanoic acid, and then the cells in the late logarithmic to early stationary growth phase are harvested by centrifugation or the like to extract the enzyme from the cells. When cells are cultured as above, mcl-PHA is synthesized in the cells from added alkanoic acid. In this case, it has been considered that PHA synthetase exists in a bound form to the fine particles of PHA synthesized in the cell. However, the inventors have found that substantial enzyme activity is present in the supernatant when the cultured cells were disrupted and centrifuged. Presumably, a certain amount of free PHA synthetase is present because this enzyme is actively synthesized during this relatively early growth phase of the late logarithmic to early stationary phase.

Any inorganic culture medium can be used for the above described culture process as long as the medium contains ingredients such as phosphorus source (phosphate etc.), and nitrogen source (ammonium salt, nitrate etc.) to support microbial growth. Therefore, MSB medium, E medium (J. Biol. Chem., 218, 97-106 (1956)), or M9 medium can be used as the inorganic salt medium, for example. Composition of M9 medium which is used in Examples is same as explained in the foregoing.

In addition, it is preferable to add the stock solution of trace ingredients of the following composition to about 0.3% (v/v), for good proliferation and production of PHA synthetase.

Culture temperature is chosen to be favorable for proliferation of the above strains, so that, for example, in the range of 14 to 40° C., preferably about 20 to 35° C.

It is also possible to produce PHA synthetase by using a transformant to which the PHA synthetase gene of the above PHA producing strain has been introduced. Cloning of the PHA synthetase gene, construction of expression vectors and transformants can be done according to the conventional methods. To culture a transformant obtained using a bacterial host such as *Escherichia coli*, natural media such as LB medium or synthetic media such as M9 medium can be used. Cells are cultured with aeration for 8 to 27 hours at 25 to 37° C. After culture, cells are collected to recover PHA synthetase accumulated in the cells. Antibiotics such as kanamycin, ampicillin, tetracycline, chloramphenicol, and streptomycin may be added to the culture as required. In addition, if the an inducible promoter is used in the expression vector, expression may be promoted by adding a corresponding inducer to the culture medium when the transformant is cultured. Such an inducer may be isopropyl-β-D-thiogalactopyranoside (IPTG), tetracycline, or indoleacrylic acid (IAA).

The PHA synthetase may be a crude enzyme such as a cell lysate or protein components precipitated with ammonium sulfate, or a purified enzyme purified by various methods. The enzyme preparation may be added with a stabilizer or activator such as metallic salts, glycerin, dithiothreitol, EDTA, and bovine serum albumin (BSA) as required.

PHA synthetase may be isolated and purified by any method as long as the enzyme activity is maintained. For example, the enzyme can be purified as follows: a crude enzyme or ammonium sulfate precipitate thereof, prepared by disrupting microbial cells by using a French press or ultrasonic homogenizer, lysozyme, or various surfactants and by centrifuging the cell lysate, is purified by affinity chromatography, cation or anion exchange chromatography, gel filtration, or a certain combination thereof. Recombinant proteins, those expressed as a fusion protein having a tag such as histidine residue at N-terminus or C terminus, can be purified easily by binding through this tag to the affinity resin. The protein of interest may be isolated from the fusion protein by treating with protease such as thrombin and blood coagulation factor Xa, by lowering pH, or by adding high concentration imidazole as a binding competitive agent. Alternatively, when pTYB1 (made by New England Biolabs Inc.) was used as an expression vector, and the tag contains inteins, the bonding may be broken under reduced conditions by using dithiothreitol. In addition to the histidine tag, glutathione S-transferase (GST), chitin binding domain (CBD), maltose binding protein (MBP), and thioredoxin are known to allow affinity purification of fusion proteins. The GST fusion protein can be purified by a GST affinity resin.

Enzyme activity of PHA synthetase can be measured various known methods. For example, the following method that measures CoA released from 3-hydroxyacyl CoA during PHA polymerization reaction catalyzed by PHA synthetase utilizing color development with 5,5'-dithiobis-(2-nitrobenzoic acid):

Reagent 1: a 3.0 mg/ml solution of bovine serum albumin (Sigma) dissolved in 0.1 M Tris-HCl buffer (pH 8.0), Reagent 2: a 3.0 mM solution of 3-hydroxyoctanoyl CoA in 0.1 M Tris-HCl buffer (pH 8.0); Reagent 3: a 10 mg/ml solution of trichloroacetic acid in 0.1 M Tris-HCl buffer (pH 8.0) Reagent 4: a 2.0 mM solution of 5,5'-dithiobis-(2-nitrobenzoic acid) in 0.1 M Tris-HCl buffer (pH 8.0).

First reaction (PHA synthesizing reaction): 100 µl of Reagent 1 is added to and mixed with 100 µl of the sample (enzyme) solution, then the mixture is pre-incubated for one minute at 30° C., to which 100 µL of Reagent 2 is added and mixed. The resultant mixture is incubated for 1 to 30 minutes at 30° C. and the reaction is stopped by adding Reagent 3.

Second reaction (color development of free CoA): The resulting first reaction solution is centrifuged (15,000×g, for 10 minutes). To 500 µl of the supernatant, 500 µl of Reagent 4 is added and incubated for 10 minutes at 30° C. Then the absorbance at 412 nm is measured.

Calculation of enzyme activity: The amount of enzyme that releases 1 µmol of CoA within one minute is defined as one unit (U).

Generally, PHA synthesized by the above described enzyme is an isotactic polymer made with R bodies alone.

<Particulate Construct Containing Hydrophilic Drug and Its Producing Method>

According to one embodiment of the present invention, the particulate construct contains at least a drug and PHA, and can assume various configurations such as microspheres or microcapsules. Specific examples are microcapsules including the drug in a core containing PHA, and microspheres in which the drug is dissolved or dispersed in PHA as solid solution in molecular state.

The particulate construct of the invention, usable for slow releasing preparation singly or with necessary additives, can be prepared from a w/o emulsion in which a solution containing a drug component constitutes the inner water phase and a solution containing PHA constitutes the oil phase, or a w/o/w emulsion which is formed by emulsifying the w/o emulsion further in an external water phase using various methods.

Such methods include in-liquid drying, phase separation, spray drying and the like.

Alternatively, the particulate construct can be prepared by in vitro synthesis, where PHA synthesis is carried out in a w/o emulsion of which inner water phase contains the drug, PHA synthesizing enzyme and 3-hydroxyacyl CoA, or in a w/o/w emulsion which is formed by emulsifying the w/o emulsion in an external water phase which may also contain PHA synthesizing enzyme and 3-hydroxyacyl CoA.

Alternatively, particulate construct can be suitably produced by PHA synthesis reaction using a w/o/w emulsion prepared by emulsifying a w/o emulsion of which inner water phase is a drug solution in an external water phase containing PHA synthesizing enzyme and 3-hydroxyacyl CoA.

<Preparation of W/O Emulsion—Incorporating Hydrophilic Drug—>

An w/o emulsion, of which inner phase is a solution containing a drug and of which oil phase is a solution containing PHA of the present invention constitutes oil phase, can be prepared in the following manner.

First, a water-soluble drug is dissolved or dispersed in water, if necessary, with a drug retaining substance such as gelatin, agar, polyvinyl alcohol or basic amino acid (such as arginine, histidine or lysine) for the inner water phase. The drug concentration therein is within the range of about 0.001 to 90 wt. %, preferably 0.01 to 80 wt. %. The drug retaining substance is added within a range of about 0.01 to 100 fold by weight, preferably 0.05 to 50 fold of the drug. It is also possible that such a drug retaining substance is first dissolved at an arbitrary concentration in water together with the drug, filtered through a filter for removing microorganisms and dusts, and lyophylized for stock, and then dissolved before use. The drug-trapping efficiency of the slow releasing preparation of the present invention is sufficiently high without a drug retaining substance in the inner phase. The inner water phase may contain a pH adjusting agent to maintain the stability and solubility of the drug, such as carboxylic acid, acetic acid, oxalic acid, citric acid, phosphoric acid, hydrochloric acid, sodium hydroxide, arginine, lysine or salts thereof. Also as a stabilizer for the drug, it may contain albumin, gelatin, trehalose, citric acid, EDTA, dextrin, cyclodextrin ($\alpha$, $\beta$, $\gamma$) or derivatives thereof (such as maltosyl $\beta$-cyclodextrin or $\beta$-cyclodextrin sulfobutyl ether), sodium hydrogen sulfite, a polyol such as polyethylene glycol, a surfactant such as polyoxyethylene sorbitan fatty acid ester (for example Tween 80 or Tween 60 (Kao, Japan) or polyoxyethylene linseed oil derivative (HCO-60 or HCO-70, Nikko Chemicals, Japan). It may also contain a common preservative agent such as paraoxybenzoic acid esters (methylparaben or propylparaben), benzyl alcohol, chlorobutanol and thymelosal.

Thus obtained inner water phase is mixed with a PHA-containing solution (oil phase) and emulsified to prepare a w/o emulsion. Emulsification can be achieved by a known method, for example, intermittent vibration method, agitation utilizing a mixer such as a propeller agitator or a turbine agitator, colloid mill method, homogenizer method or ultrasonication, or a combination thereof. The emulsification level of the w/o emulsion will affect the drug release, and insufficient emulsification tends to increase the initial burst. The finer the size of the inner water phase is, the more interaction between the drug and PHA is improved, enabling more accurate release control by PHA according to the kind/composition ratio/molecular weight/crystallinity of PHA.

The oil phase containing PHA is a solution of PHA dissolved in an organic solvent substantially immiscible with water. Solubility of the organic solvent in water does not preferably exceed 3 wt. % at normal temperature (20° C.). Also the boiling point of the organic solvent preferably does not exceed 120° C. Examples of such an organic solvent include halogenated hydrocarbons such as dichloromethane, chloroform, chloroethane, dichloroethane, trichloroethane, and carbon tetrachloride; ketones such as acetone, methylethylketone, and methylisobutyl ketone; ethers such as tetrahydrofuran, ethyl ether and isopropyl ether; esters such as ethyl acetate or butyl acetate; and aromatic hydrocarbons such as benzene, toluene and xylene; which may be employed in a mixture of two or more kinds. More preferably, the organic solvent is halogenated hydrocarbons (such as dichloromethane, chloroform, chloroethane, dichloroethane, trichloroethane, or carbon tetrachloride). The PHA concentration in the oil phase may vary depending on the kind and molecular weight of PHA and the kind of solvent, but is preferably within a range of about 0.01 to 80 wt. %, more preferably 0.1 to 70 wt. %, and most preferably 1 to 60 wt. %. In order to vary the compatibility with the inner water phase, distribution into the external water phase and evaporation of the organic solvent, a partially hydrophilic organic solvent such as ethanol, acetonitrile, acetone and tetrahydrofuran may be added to the oil phase. Also in order to dissolve or stabilize the drug inside, a surfactant such as a glucose-fatty acid ester can be added. Thus-obtained oil phase may be filtered for eliminating microbes and dust before use. The PHA-containing solution may be stored in a tightly closed container at room temperature or in a cool place according to the stability of PHA.

The mixing ratio of the aqueous solution containing the drug to the organic solvent solution containing PHA is 1: about 0.1 to 1000, preferably 1: about 1-100 (part by weight). Also the amount of the drug in the slow releasing preparation, depending on the kind, desired pharmaceutical effect and duration of effect of the drug, is within a range of about 0.01 to 50 wt. % of PHA, preferably 0.1 to 40 wt. % and more preferably 1 to 30 wt. %.

<Preparation of W/O/W Emulsion and In-Liquid Drying—Incorporating Hydrophilic Drug—>

Then, thus obtained w/o emulsion is subjected to a particulate forming process. For example, when particulate formation is carried out by in-liquid drying, the w/o emulsion is further added to a water phase (hereinafter called external water phase) to prepare a w/o/w emulsion, and then the organic solvent in the oil phase is eliminated to obtain the particulate construct such as microcapsules.

The volume of the external water phase is generally selected within a range of about 1 to 10,000 times of that of the oil phase, preferably 2 to 5,000 times and more preferably 5 to 2,000 times.

The external water phase may be added with an emulsifier, which can be any emulsifier capable of forming stable w/o/w emulsion and which can be, for example, an anionic surfactant (such as sodium oleate, sodium stearate or sodium laurylsulfate), a nonionic surfactant [such as polyoxyethylene sorbitan fatty acid ester (Tween 80 or Tween 60, Atlas Powder, U.S.) or polyoxyethylene linseed oil derivative (HCO-70, HCO-60 or HCO-50, Nikko Chemicals, Japan)], polyvinyl pyrrolidone, polyvinyl alcohol, carboxymethyl cellulose, lecithine, gelatin, hyaluronic acid or derivatives thereof. These may be used singly or as a combination of plural kinds. The concentration of emulsifier in the external water phase is within a range of about 0.01 to 20 wt. %, preferably 0.05 to 10 wt. %.

The aforementioned external water phase may also be added with an osmotic pressure-adjusting agent, which can be any substance of which aqueous solution shows osmotic pressure and including water-soluble polyhydric alcohols, water-soluble monohydric alcohols, water-soluble monosaccharides, disaccharides, oligosaccharides and derivatives thereof, water-soluble amino acids, water-soluble peptides, proteins and derivatives thereof.

The aforementioned water-soluble polyhydric alcohols include dihydric alcohols such as glycerin, pentahydric alcohols such as arabitol, xylitol or adonitol, hexahydric alcohols such as mannitol, sorbitol or zurcitol, among which preferred is hexahydric alcohol, particularly mannitol. The aforementioned water-soluble monohydric alcohols include methanol, ethanol and isopropyl alcohol, among which preferred is ethanol. The aforementioned water-soluble monosaccharides include 5-carbon sugars such as arabinose, xylose, ribose or 2-deoxyribose, and 6-carbon sugars such as glucose, fructose, galactose, mannose, sorbose, rhamnose or fucose, among which preferred are 6-carbon sugars. The aforementioned water-soluble disaccharides include maltose, cellobiose, α,α-trehalose, lactose and glucose, among which preferred are lactose and glucose. The aforementioned water-soluble oligosaccharides include trisaccharides such as maltotriose or raffinose, and tetrasaccharides such as stachyose, among which preferred are trisaccharides. The derivatives of the aforementioned water-soluble monosaccharides, disaccharides and oligosaccharides include glucosamine, galactosamine, glucuronic acid and galacturonic acid.

The aforementioned water-soluble amino acids include neutral amino acids such as glycine, alanine, valine, leucine, isoleucine, phenylalanine, tyrosine, tryptophan, serine, threonine, proline, hydroxyproline, cysteine or methionine, acidic amino acids such as aspartic acid or glutamic acid, and basic amino acids such as lysine, arginine or histidine. There may also be employed salts of such water-soluble amino acids with an acid (hydrochloric acid, sulfuric acid or phosphoric acid) or with an alkali (alkali metal such as sodium or potassium). The water-soluble peptides, proteins and derivatives thereof include casein, globulin, prolamine, albumin and gelatin. Among the aforementioned osmotic pressure-adjusting agents, preferred are water-soluble polyhydric alcohols, and water-soluble monosaccharides, disaccharides, oligosaccharides and derivatives thereof, more preferably water-soluble polyhydric alcohols and water-soluble monosaccharides, and most preferably water-soluble polyhydric alcohols. Such osmotic pressure-adjusting agents may be used singly or in a combination of two or more. Such osmotic pressure-adjusting agent is used at such concentration that the osmotic pressure of the external water phase is about 1/50 to 5 times of that of physiological saline, preferably 1/25 to 3 times. More specifically, the concentration of the osmotic pressure-adjusting agent in the external water phase is, in case of a nonionic substance, in a range of about 0.001 to 60 wt. %, preferably 0.01 to 40 wt. %, more preferably 0.05 to 30 wt. % and most preferably 1 to 10 wt. %.

In case of an ionic substance, the osmotic pressure-adjusting agent is employed at a concentration obtained by dividing the above-mentioned concentration with the total ion value. The addition amount of the osmotic pressure-adjusting agent need not be below the solubility but can be partly in a suspended state.

When the w/o/w emulsion is prepared in the method of the present invention, viscosity of the w/o emulsion is preferably adjusted within a range of 50~10,000 cp. The viscosity can be adjusted, for example by (1) adjustment of PHA concentration in the oil phase, (2) adjustment of ratio of water phase and oil phase, (3) adjustment of temperature of w/o emulsion, (4) adjustment of temperature of the external water phase, or (5) adjustment of temperature of w/o emulsion with a line heater or a cooler at the charging thereof into the external water phase. These methods may be used singly or in combination. In these methods, there is only required that the viscosity of the w/o emulsion is within a range of 50 to 10,000 cp at the conversion thereof into w/o/w emulsion. In the above-mentioned method (1), the concentration to be adjusted of PHA in the oil phase cannot be uniquely determined as it is dependent on the types of PHA and organic solvent, but is preferably about 10 to 80 wt. %. In the above-mentioned method (2), the ratio to be adjusted of water phase and oil phase cannot be determined as it is dependent on the type and amount of the drug and the property of the oil phase, but preferably w/o=about 1 to 50 vol. %. In the above-mentioned method (3), temperature of the w/o emulsion may be adjusted, for example, within a range from about −20° C. to the boiling point of the organic solvent, preferably 0 to 30° C., and more preferably 10 to 20° C. The viscosity of the w/o emulsion can be adjusted at the time of preparation thereof in the method of (1) or (2). In the above-mentioned method (4), the temperature of the external water phase may be adjusted before addition of the w/o emulsion so as to obtain a result similar to the above-mentioned method (3). The temperature of the external water phase is for example about 5 to 30° C., preferably 10 to 25° C. and more preferably 12 to 25° C.

The elimination of the organic solvent can be executed by a known method, such as a method of evaporating the organic solvent at normal pressure or at a gradually reduced pressure under agitation with a propeller agitator or a magnetic stirrer, or a method of evaporating the organic solvent under controlled vacuum and temperature for example in a rotary evaporator.

Thereafter, the particulate construct is acquired centrifugation or filtration, then washed several times with distilled water to eliminate free drug, drug retaining substance, emulsifier etc. sticking on the surface of the particulate construct, and the remaining solvent and water are removed by drying under a reduced pressure or by lyophilization after re-dispersion in distilled water.

<Phase Separation—Incorporating Hydrophilic Drug—>

In case of particulate formation by phase separation, the particulate construct is prepared by gradually adding a coacervation agent to the w/o emulsion under agitation, thereby precipitating and solidifying PHA. The coacervation agent can be any substance based on polymer, mineral oil or vegetable oil miscible with the solvent of PHA and not dissolving PHA for particulate formation, and can be, for example, silicone oil, sesame oil, soybean oil, corn oil, cotton seed oil, coconut oil, linseed oil, mineral oil, n-hexane, n-heptane, methanol or ethanol, which may also be employed in combination of two or more.

The amount of the coacervation agent with respect to w/o emulsion is for example about 0.01 to 1,000 times by volume, preferably 0.1 to 200 times by volume. The obtained particulate construct is acquired by centrifugation or filtration, then washed repeatedly with washing liquid such as hexane or heptane to eliminate the coacervation agent, and the washing liquid is evaporated by heating or under a reduced pressure. Thereafter, if desired, the free drug and the organic solvent are removed as in the aforementioned case of in-liquid drying.

<Spray Drying—Incorporating Hydrophilic Drug—>

In case of particulate formation by spray drying, the w/o emulsion or the w/o/w emulsion prepared in the same manner as in the in-liquid drying is sprayed from a nozzle into a drying chamber of a spray drier to evaporate the organic solvent and water in the pulverized liquid droplets within an extremely short time, thereby preparing the particulate construct such as microcapsules in fine powder state. The nozzle can be a two-fluid nozzle, a pressurized nozzle or a rotary disk type. The obtained particulate construct is washed, if desired, several times with distilled water to eliminate free drug, drug retaining substance, emulsifier etc. sticking on the surface of the particulate construct. Then, the washed microcapsules may be subjected to elimination of the organic solvent by drying under a reduced pressure or by lyophilization after re-dispersion in distilled water.

<Particulate Construct and Its Producing Method—Incorporating Oleophilic Drug—>

The particulate construct of the present invention is particulate construct containing at least a drug and PHA, and can assume various configurations such as microspheres or microcapsules. Specific examples include microcapsules including the drug in a core containing PHA, and particulate construct (microspheres) in which the drug is dissolved or dispersed in PHA as solid solution in molecular state.

The particulate construct of the present invention can be prepared by eliminating organic solvent from the oil phase containing the drug, PHA and organic solvent. In the method of the present invention, for preparing organic solvent liquid containing (a) drug and (b) PHA, there may be adopted any method in which (a) and (b) are finally uniformly dissolved or dispersed in a solvent system. Examples of such method include (1) a method of mixing a solution or a dispersion of (a) in a solvent, and a solution or a dispersion of (b) in a solvent, (2) a method of mixing a solution or a dispersion of (a) in a solvent, and (b), (3) a method of mixing a solution or a dispersion of (b) in a solvent, and (a), and (4) a method of mixing (a), (b) and a solvent to form a solution of (a), (b) in a solvent. The above-mentioned solvents are suitably so selected that (a) and (b) are retained in dissolved state after the mixing of the solvents. More specifically, the above-mentioned solvent can be obtained by one of the aforementioned organic solvents or by mixing two or more thereof at a suitable proportion, and, if desired, by adding the aforementioned organic solvent to such an extent not hindering the dissolution of (a) and (b).

The particulate construct of the present invention such as microcapsules can be produced by eliminating organic solvent from the oil phase comprised of solution or dispersion of the drug and PHA.

More specifically there can be employed the already known method for preparing the particulate construct such as microcapsules, such as a method of evaporating the solvent thereby solidifying the particulate construct (in-liquid drying), a method of adding, to the aforementioned solution or suspension, a solvent miscible therewith but not dissolving PHA (so-called poor solvent) under agitation to achieve phase separation of PHA thereby forming solidified particulate construct, a method of obtaining particular construct by spray drying, a gaseous crushing method of crushing a solid, obtained by eliminating the organic solvent from the aforementioned oil phase, with a jet mill or the like, or a similar method.

There can also be advantageously employed a method (in vitro synthesis) of dissolving and/or suspending the drug in organic solvent, charging and emulsifying such organic phase in a large amount of water containing PHA synthesizing enzyme and 3-hydroxyacyl CoA to obtain o/w emulsion and executing PHA synthesizing reaction to prepare the particulate construct such as microcapsules.

<Examples of Organic Solvent—Incorporating Oleophilic Drug—>

As the aforementioned organic solvent, there is preferred organic solvent having solubility in water not exceeding 3 wt. % at normal temperature (20° C.). Also the boiling point of the organic solvent preferably does not exceed 120° C. Examples of such organic solvent include halogenated hydrocarbons (such as dichloromethane, chloroform, chloroethane, dichloroethane, trichloroethane, or carbon tetrachloride), ketones (such as acetone, methylethylketone, or methylisobutyl ketone), ethers (such as tetrahydrofuran, ethyl ether or isopropyl ether), esters (such as ethyl acetate or butyl acetate), and aromatic hydrocarbons (such as benzene, toluene or xylene), which may be employed in a mixture of two or more kinds. More preferably, the organic solvent is halogenated hydrocarbon (such as dichloromethane, chloroform, chloroethane, dichloroethane, trichloroethane, or carbon tetrachloride).

<Drug/PHA Concentration—Incorporating Oleophilic Drug—>

The amount of the drug is dependent on the kind of the drug and the desired duration of effect, but the concentration in solution is within a range of about 0.001 to 200 w/w %, preferably 0.001 to 100 w/w % and more preferably 0.01 to 50 w/w %. Also the amount of the drug in the preparation, through dependent on the kind of the drug, desired pharmaceutical effect and duration of effect, is within a range of about 0.01 to 60 w/w % with respect to PHA, preferably 0.1 to 55 wt. % and more preferably 1 to 50 wt. %. The PHA concentration is variable depending on the molecular weight of PHA and the kind of solvent, but is preferably within a range of about 0.01 to 80 w/w %, more preferably 0.1 to 70 w/w %, and most preferably 1 to 60 w/w %.

<In-Liquid Drying—incorporating Hydrophilic Drug—>

The preparation of particulate construct such as microcapsules by in-liquid drying is usually achieved by dispersing an oil phase containing the drug, PHA and organic solvent in a water phase to form o/w emulsion, and then eliminating the solvent in the oil phase. The volume of the water phase is generally selected within a range of about 1 to 10,000 times of that of the oil phase, preferably 2 to 5,000 times and more preferably 5 to 2,000 times. The temperature of the water phase may be adjusted in advance for example to about 5 to 30° C., preferably 10 to 25° C., more preferably 10 to 20° C. The water phase may be added with an emulsifier, which can be any emulsifier capable of forming stable o/w emulsion and which can be, for example, an anionic surfactant (such as sodium oleate, sodium stearate or sodium laurylsulfate), a nonionic surfactant such as polyoxyethylene sorbitan fatty acid ester (Tween 80 or Tween 60, Atlas Powder, U.S.) or polyoxyethylene linseed oil derivative (HCO-70, HCO-60 or HCO-50, Nikko Chemicals, Japan)], polyvinyl pyrrolidone, polyvinyl alcohol, carboxymethyl cellulose, lecithine, gelatin, hyaluronic acid or derivatives thereof. These may be used singly or as a combination of plural kinds. The concentration of emulsifier in the external water phase is within a range of about 0.01 to 20 wt. %, preferably 0.05 to 10 wt. %. The volume of the water phase is generally selected within a range of about 1 to 10,000 times of that of the oil phase, preferably 2 to 5,000 times, more preferably 5 to 2,000 times, and most preferably 5 to 1,000 times. The water phase may be added with an emulsifier, which can be any emulsifier capable of forming stable o/w emulsion.

The emulsifier is preferably a non-toxic and non-antigen emulsifier and can be, for example, an anionic surfactant (such as sodium oleate, sodium stearate or sodium laurylsulfate), a cationic surfactant (such as lauryltrimethylammonium chloride) an amphoteric surfactant (such as N-laurylglycine), a nonionic surfactant such as polyoxyethylene sorbitan fatty acid ester (Tween 80 or Tween 60, Tween 40 or Tween 20, Atlas Powder, U.S.) or polyoxyethylene linseed oil derivative (HCO-70, HCO-60 or HCO-50, Nikko Chemicals, Japan)], polyvinyl pyrrolidone, polyvinyl alcohol, methyl cellulose, carboxymethyl cellulose, hydroxyethyl cellulose, lecithin, starch, casein, pectin, gelatin, alginic acid, alginate, locust bean gum, guar gum, gum Arabic, xanthane gum, agar, carrageenan, hyaluronic acid, bile acid salt, sodium colate, or polyoxyethylene ether. These may be used as a mixture of two or more in a suitable proportion.

The concentration of emulsifier at use can be suitably selected within a range of about 0.001 to 20 w/v %, preferably 0.01 to 10 w/v %, and more preferably 0.05 to 5 w/v %. The emulsification can be achieved by a known method, for example intermittent vibration, agitation utilizing a mixer such as a propeller agitator or a turbine agitator, high-speed rotation with a narrow gap between a rotor and a stator, ultrasonic vibration, ultrasonic passage through a narrow gap, or passage through an inorganic membrane obtained by sintering silace balloons and having fine pores.

Such w/o emulsion affects the drug release by the level of emulsification, and, if it is insufficient, tends to increase the initial burst, and, an inner water phase finer than a certain level is preferable as it increases the interaction of the drug and PHA and enables more accurate release control by PHA depending on the biodegradability of PHA.

The supply of constituents in the preparation of o/w emulsion of the present invention can assume various modes according to the known technologies, such as a method of charging PHA solution in a container and adding water phase containing the emulsifier, a method of inverting the order of addition, or a method of continuously supplying both at a constant ratio. In case of mixing by rotation, the order mentioned at first is preferable. In such case, there is initially formed w/o emulsion in which the PHA constitutes the continuous phase and the water phase constitutes the dispersed phase, and the emulsion is converted from the w/o type to the o/w type with an increase in the added amount of the water phase component, thereby accelerating the particulate formation of the oil phase.

The elimination of the organic solvent can be executed by a known method, such as a method of evaporating the organic solvent at normal pressure or at a gradually reduced pressure under agitation with a propeller agitator or a magnetic stirrer, or a method of evaporating the organic solvent under controlled vacuum for example in a rotary evaporator. In the in-liquid drying of o/w emulsion, the particulate construct is solidified whereby the structure thereof is determined. The particulate construct thus obtained is acquired by centrifugation or filtration, then washed several times with distilled water to eliminate free drug, drug retaining substance, emulsifier etc. sticking on the surface of the particulate construct, then re-dispersed in distilled water etc. and lyophilized.

<Phase Separation—Incorporating Oleophilic Drug—>

In case of preparation of particulate construct such as microcapsules by phase separation, a coacervation agent is gradually added to an organic solvent containing the drug and PHA at a constant rate under agitation, thereby precipitating and solidifying PHA. Such a coacervation agent is added in an amount of 0.01 to 1,000 fold of the organic solvent solution of drug and PHA, preferably 0.05 to 500 times, more preferably 0.1 to 200 times. The coacervation agent can be any substance based on polymer, mineral oil or vegetable oil miscible with the solvent of PHA and not dissolving PHA for particulate formation, and can be, for example, silicone oil, sesame oil, soybean oil, corn oil, cotton seed oil, coconut oil, linseed oil, mineral oil, n-hexane, n-heptane, methanol or ethanol.

These may also be employed in combination of two or more. The obtained particulate construct such as microcapsules is acquired by filtration, then washed repeatedly with heptane etc. to eliminate the coacervation agent, and then subjected to the elimination of the free drug and the organic solvent.

<Particulate Construct and Its Producing Method—Incorporating Liquid Phase—>

The microcapsules of the present invention can be fine particles containing at least a drug and PHA, and can assume configurations explained in the foregoing.

The microcapsules of the present invention can be prepared by microencapsulating w/o emulsion, comprised of an inner water phase and a solution containing the drug and constituting the inner water phase, or w/o/w emulsion which is formed by emulsifying the w/o emulsion further in an external water phase, or o/w emulsion comprised of an oil phase containing PHA and an external water phase. Such microencapsulation can be achieved for example by in-liquid drying, phase separation, spray drying or a similar method.

There can also be advantageously employed a method of producing microcapsules (in vitro synthesis) by forming w/o emulsion, in which a solution containing PHA synthesizing enzyme and 3-hydroxyacyl CoA constitute the inner water phase, or w/o/w emulsion which is formed by emulsifying the w/o emulsion further in an external water phase which may contain PHA synthesizing enzyme and 3-hydroxyacyl CoA, or o/w emulsion in which a solution containing PHA synthesizing enzyme and 3-hydroxyacyl CoA constitutes an external water phase and by executing PHA synthesizing reaction.

<Preparation of W/O Emulsion—Incorporating Liquid Phase—>

The w/o emulsion, comprised of an inner water phase and an oil phase containing PHA of the present invention can be prepared in the following manner.

At first water of the inner water phase can be aqueous solution of an inorganic or organic salt, in order to match the specific gravity with that of the organic solvent solution of the external oil phase. The inorganic salt can be, for example, calcium chloride, sodium chloride, potassium chloride, calcium bromide, sodium bromide, sodium carbonate, sodium hydrogen carbonate, potassium carbonate or potassium hydrogen carbonate. Also the organic salt can be, for example, sodium or potassium salt of an organic acid such as acetic acid, oxalic acid, citric acid, tartaric acid, succinic acid, phosphoric acid or ascorbic acid. Among these, aqueous solution of calcium chloride is desirable in the present invention, in consideration of economy, ease of specific gravity matching and ease of washing. Such inorganic or organic salt is added to water in an amount of about 1 to 60 w/v %, preferably 20 to 50 w/v %, so as to match the specific gravity with that of the organic solvent solution of PHA. In this manner there can be obtained w/o emulsion in which the water droplets are uniformly dispersed in the oil phase.

Thus obtained inner water phase and PHA-containing solution (oil phase) are mixed and emulsified to prepare w/o emulsion. The emulsification can be achieved by a known method, for example intermittent vibration, agitation utilizing a mixer such as a propeller agitator or a turbine agitator, colloid mill method, homogenizer method or ultrasonic irradiation, or a combination thereof. The primary emulsification for preparing the w/o emulsion is important in ensuring the uniformity of the final microcapsule structure, and it is necessary, at this stage, to disperse the inner water phase as uniformly as possible in the organic solvent solution of PHA. For this purpose it is preferred to reduce as far as possible the diameter of the water droplets of the inner water phase, and there is advantageously employed ultrasonic irradiation combined with another dispersion method.

The aforementioned solution (oil phase) containing PHA is comprised of solution of PHA dissolved in organic solvent substantially immiscible with water. The solubility of such organic solvent in water does not preferably exceed 3 wt. % at normal temperature (20° C.). Also the boiling point of the organic solvent preferably does not exceed 120° C. Examples of the organic solvent include halogenated hydrocarbons (such as dichloromethane, chloroform, chloroethane, dichloroethane, trichloroethane, or carbon tetrachloride), ketones (such as acetone, methylethylketone, or methylisobutyl ketone), ethers (such as tetrahydrofuran, ethyl ether or isopropyl ether), esters (such as ethyl acetate or butyl acetate), and aromatic hydrocarbons (such as benzene, toluene or xylene), which may be employed in a mixture of two or more kinds. More preferably, the organic solvent is halogenated hydrocarbons (such as dichloromethane, chloroform, chloroethane, dichloroethane, trichloroethane, or carbon tetrachloride). The PHA concentration in the oil phase is variable depending on the kind and molecular weight of PHA and the kind of solvent, but is preferably within a range of about 0.01 to 80 wt. %, more preferably 0.1 to 70 wt. %, and most preferably 1 to 60 wt. %. In order to vary the mutual solubility with the inner water phase, distribution of the organic solvent to the external water phase and evaporation of the organic solvent, the oil phase may be partly added with hydrophilic organic solvent such as ethanol, acetonitrile, acetone or tetrahydrofuran. Thus obtained oil phase may be filtered for eliminating bacteria and dust before use. Also, though dependent on the stability of PHA, the solution containing PHA may be stored in a tightly closed container at room temperature or in a cool place.

The mixing ratio of the aqueous solution and the organic solvent solution containing PHA is, with respect to 1 part by weight of the former, within a range of about 0.1 to 1000 parts by weight of the latter, preferably about 1 to 100 parts by weight.

<Preparation of W/O/W Emulsion and In-Liquid Drying—Incorporating Liquid Phase—>

Then, thus obtained w/o emulsion is subjected to a microencapsulation process. For example, when microencapsulation is carried out by in-liquid drying, the w/o emulsion is further added to a water phase (hereinafter called external water phase) to prepare a w/o/w emulsion, and then the organic solvent in the oil phase is removed to obtain microcapsules.

The volume of the external water phase is generally selected within a range of about 1 to 10,000 times of that of the oil phase, preferably 2 to 5,000 times and more preferably 5 to 2,000 times.

The external water phase may be added with an emulsifier, which can be any emulsifier capable of forming stable w/o/w emulsion and which can be, for example, an anionic surfactant (such as sodium oleate, sodium stearate or sodium laurylsulfate), a nonionic surfactant [such as polyoxyethylene sorbitan fatty acid ester (Tween 80 or Tween 60, Atlas Powder, U.S.) or polyoxyethylene linseed oil derivative (HCO-70, HCO-60 or HCO-50, Nikko Chemicals, Japan)], polyvinyl pyrrolidone, polyvinyl alcohol, carboxymethyl cellulose, lecithine, gelatin, hyaluronic acid or derivatives thereof. These may be used singly or as a combination of plural kinds. The concentration of emulsifier in the external water phase is within a range of about 0.01 to 20 wt. %, preferably 0.05 to 10 wt. %.

The aforementioned external water phase may also be added with an osmotic pressure-adjusting agent, which can be any substance of which aqueous solution shows osmotic pressure including water-soluble polyhydric alcohols, water-soluble monohydric alcohols, water-soluble monosaccharides, disaccharides, oligosaccharides and derivatives thereof, water-soluble amino acids, water-soluble peptides, proteins and derivatives thereof.

The aforementioned water-soluble polyhydric alcohols include dihydric alcohols such as glycerin, pentahydric alcohols such as arabitol, xylitol or adonitol, hexahydric alcohols such as mannitol, sorbitol or zurcitol, among which preferred is hexavalent alcohol, particularly mannitol. The aforementioned water-soluble monohydric alcohols include methanol, ethanol and isopropyl alcohol, among which preferred is ethanol. The aforementioned water-soluble monosaccharides include 5-carbon sugars such as arabinose, xylose, ribose or 2-deoxyribose, and 6-carbon sugars such as glucose, fructose, galactose, mannose, sorbose, rhamnose or fucose, among which preferred are 6-carbon sugars. The aforementioned water-soluble disaccharides include maltose, cellobiose, α,α-trehalose, lactose and glucose, among which preferred are lactose and glucose. The aforementioned water-soluble oligosaccharides include trisaccharides such as maltotriose or raffinose, and tetrasaccharides such as stachyose, among which preferred are trisaccharides. The derivatives of the aforementioned water-soluble monosaccharides, disaccharides and oligosaccharides include glucosamine, galactosamine, glucuronic acid and galacturonic acid.

The aforementioned water-soluble amino acids include neutral amino acids such as glycine, alanine, valine, leucine, isoleucine, phenylalanine, tyrosine, tryptophan, serine, threonine, proline, hydroxyproline, cysteine or methionine, acidic amino acids such as aspartic acid or glutamic acid, and basic amino acids such as lysine, arginine or histidine. There may also be employed salts of such water-soluble amino acids with an acid (hydrochloric acid, sulfuric acid or phosphoric acid) or with an alkali (alkali metal such as sodium or potassium). The water-soluble peptides, proteins and derivatives thereof include casein, globulin, prolamine, albumin and gelatin. Among the aforementioned osmotic pressure-adjusting agents, preferred are water-soluble polyhydric alcohols, and water-soluble monosaccharides, disaccharides, oligosaccharides and derivatives thereof, more preferably water-soluble polyhydric alcohols and water-soluble monosaccharides, and most preferably water-soluble polyhydric alcohols. Such osmotic pressure-adjusting agents may be used singly or in a combination of two or more. Such osmotic pressure adjusting agent is used at such concentration that the osmotic pressure of the external water phase is about 1/50 to 5 times of that of physiological saline, preferably 1/25 to 3 times. More specifically, the concentration of the osmotic pressure-adjusting agent in the external water phase is, in case of a nonionic substance, in a range of about 0.001 to 60 wt. %, preferably 0.01 to 40 wt. %, more preferably 0.05 to 30 wt. % and most preferably 1 to 10 wt. %. In case of an ionic substance, the osmotic pressure-adjusting agent is employed at a concentration obtained by dividing the above-mentioned concentration with the total ion value. The addition amount of the osmotic pressure-adjusting agent need not be below the solubility but can be partly in a suspended state.

In the emulsification of w/o emulsion into water, agitation is executed after w/o emulsion is dispersed in water. Agitation can be executed by any of the aforementioned emulsifying methods, but the use of a homogenizer is preferable in obtaining microcapsules of an organic solvent solution having a structure in which a single layer of organic solvent liquid phase incorporates water. In case of using the homogenizer, the agitation is executed at 100 to 100,000 rpm, preferably 1,000 to 50,000 rpm for 0.1 to 30 minutes, preferably 0.5 to 20 minutes.

By such operation, the diameter of the w/o emulsion drops in the external water phase is reduced. Thus, the agitation with the homogenizer is effective in reducing the diameter of the w/o emulsion droplets without changing the dispersion state of the water phase in the w/o emulsion droplets. It is important to reduce the diameter of w/o emulsion drops to 1 to 20 µm in order to obtain a single polymer membrane structure in the final fine particles. Then, the emulsion is let to stand in this state under agitation for example with a propeller agitator. In such state, since the inner water phase in the w/o emulsion drops is unstable, it is united to form a large single water drop before the solidification of PHA. On the other hand, since the w/o emulsion itself is stabilized by the emulsifier in the external water phase, there is formed, as a result, a capsule structure in which the inner water phase is surrounded by a single layer of organic solvent solution phase of PHA.

For accelerating the formation of w/o emulsion drops having such capsule structure, it is preferred to suitably adjust the kind and amount of the salt in the inner water phase, concentration of polymer in the oil phase, temperature of the oil phase (w/o emulsion drops) and of the emulsifying external water phase, and the ratio of the oil phase and the water phase. In particular, the use of an inorganic salt in the inner water phase increases the surface tension of the inner water phase, thereby unstabilizing the water phase to cause uniting of the water phase in the w/o emulsion drops in the course of particle formation, whereby the proportion of the emulsion of single membrane structure increases.

In preparing w/o/w emulsion in the method of the present invention, the viscosity of the w/o emulsion is preferably adjusted within a range of 50 to 10,000 cp. The viscosity can be adjusted, for example by (1) adjustment of PHA concentration in the oil phase, (2) adjustment of ratio of water phase and oil phase, (3) adjustment of temperature of w/o emulsion, (4) adjustment of temperature of the external water phase, or (5) adjustment of temperature of w/o emulsion with a line heater or a cooler at the charging thereof into the external water phase. These methods may used singly or in combination. In these methods, there is only required that the viscosity of the w/o emulsion is within a range of 50 to 10,000 cp at the conversion thereof into w/o/w emulsion. In the above-mentioned method (1), the concentration to be adjusted of PHA in the oil phase cannot be uniquely determined as it is dependent on the types of PHA and organic solvent, but is preferably about 10 to 80 wt. %. In the above-mentioned method (2), the ratio to be adjusted of water phase and oil phase cannot be determined as it is dependent on the property of the oil phase etc., but preferably w/o=about 1 to 50 vol. %. In the above-mentioned method (3), the temperature to be adjusted of the w/o emulsion is for example within a range from about −20° C. to the boiling point of the organic solvent, preferably 0 to 30° C., and more preferably 10 to 20° C. The viscosity adjustment of the w/o emulsion can be executed at the preparation thereof in case of (1) or (2). In case of the above-mentioned method (4), the temperature of the external water phase may be adjusted in advance at the addition thereto of the w/o emulsion so as to obtain a result similar to the above-mentioned method (3). The temperature of the external water phase is for example about 5 to 30° C., preferably 10 to 25° C. and more preferably 12 to 25° C.

The elimination of the organic solvent can be executed by a known method, such as a method of evaporating the organic solvent at normal pressure or at a gradually reduced pressure under agitation with a propeller agitator or a magnetic stirrer, or a method of evaporating the organic solvent under controlled vacuum and temperature for example in a rotary evaporator.

Thereafter, the microcapsules are acquired by centrifugation or filtration if necessary, then washed several times with distilled water to eliminate free drug, drug retaining substance, emulsifier etc. sticking on the surface of the particulate construct, and the remaining solvent and water are removed by drying under a reduced pressure or by lyophilization after re-dispersion in distilled water. Otherwise the microcapsule slurry prepared in the foregoing steps may directly dispersed in a suitable dispersion medium.

In case of re-dispersion in distilled water, a dispersant may be added. The dispersant has a function of preventing coagulation of the fine particles. The dispersant can be, for example, a Tween-80 like surfactant, sucrose fatty acid ester, mannitol, sorbitol, glucose, galactose or sucrose. Such dispersant is used by dissolving in water at a concentration of about 0.001 to 30 wt. %.

The generated fine particles having the single PHA membrane structure may be directly re-dispersed, but they may be centrifuged at a low speed after washing for separation into precipitate and non-precipitate, since they contain particles having porous structure. Such centrifugation is executed at a revolution of about 50 to 3,000 rpm for 1 to 60 minutes, and is preferably executed several times.

By the centrifugation, the microcapsules having the single membrane structure consisting of PHA are collected in the non-precipitate phase. Also for obtaining dry fine particles, there can be used drying under a reduced pressure with heating if necessary or lyophilization, but the latter is preferred.

In this manner obtained are microcapsules of a particle diameter of 1 to 10 μm. As will be described in the following examples, the microcapsules have a spherical shape without pores on the capsule surface.

<Phase Separation—Incorporating Liquid Phase—>

In case of preparation of microcapsules by phase separation, a coacervation agent is gradually added to organic solvent solution of the drug and PHA at a constant rate under agitation, thereby precipitating and solidifying PHA. The coacervation agent can be any substance based on polymer, mineral oil or vegetable oil miscible with the solvent of PHA and not dissolving PHA for particulate formation, and can be, for example, silicone oil, sesame oil, soybean oil, corn oil, cotton seed oil, coconut oil, linseed oil, mineral oil, n-hexane, n-heptane, methanol or ethanol. These may also be employed in combination of two or more. Such coacervation agent is added in a volume amount of 0.01 to 1,000 times of the volume of the organic solvent solution of drug and PHA, preferably 0.1 to 200 times. The obtained microcapsules are acquired by filtration or centrifuging, then washed repeatedly with heptane etc. to eliminate the coacervation agent, and then subjected to the elimination of the washing liquid by heating or under a reduced pressure. If desired, the organic solvent is eliminated in a similar manner as in the aforementioned case of in-liquid drying.

<Spray Drying—Incorporating Liquid Phase—>

In case of microencapsulation by spray drying, the w/o emulsion or the w/o/w emulsion prepared in the same manner as in the in-liquid drying is sprayed from a nozzle into a drying chamber of a spray drier to evaporate the organic solvent and water in the pulverized liquid droplets within an extremely short time, thereby preparing the microcapsules in fine powder state. The nozzle can be a two-fluid nozzle, a pressurized nozzle or a rotary disk type. The obtained microcapsules are washed, if desired, several times with distilled water to eliminate the emulsifier sticking on the surface of the microcapsules. Then, the washed microcapsules may be subjected to elimination of the organic solvent by drying under a reduced pressure or by lyophilization after re-dispersion in distilled water.

<Preparation of O/W Emulsion—Incorporating Liquid Phase—>

Microencapsulation by in-liquid drying from w/o emulsion is executed by dispersing an oil phase containing PHA and organic solvent in a water phase to form w/o emulsion, and then eliminating the solvent in the oil phase. The volume of the water phase is generally selected within a range of about 1 to 10,000 times of that of the oil phase, preferably 2 to 5,000 times and more preferably 5 to 2,000 times. The temperature of the water phase may be adjusted in advance to about 5 to 30° C., preferably 10 to 25° C., more preferably 10 to 20° C. The water phase may be added with an emulsifier, which can be any emulsifier capable of forming stable o/w emulsion and the aforementioned emulsifiers can be advantageously employed. The concentration of emulsifier in the external water phase is within a range of about 0.001 to 20 wt. %, preferably 0.01 to 10 wt. %, and more preferably 0.05 to 5 wt. %. Also the aforementioned known mixing apparatus can be employed for the emulsification step.

The emulsification for preparing the w/o emulsion is important in ensuring the uniformity of the final microcapsule structure, and it is necessary, at this stage, to disperse the inner oil phase containing PHA as uniformly as possible in the external water phase. For this purpose it is preferred to reduce as far as possible the diameter of the drops of the inner oil phase, and there is advantageously employed ultrasonic irradiation combined with another dispersion method.

The supply of constituents in the preparation of o/w emulsion of the present invention can assume various modes according to the known technologies, such as a method of charging PHA solution in a container and adding water phase containing the emulsifier, a method of inverting the order of addition, or a method of continuously supplying both at a constant ratio. In case of mixing by rotation, the order mentioned at first is preferable. In such case, there is initially formed w/o emulsion in which the PHA constitutes the continuous phase and the water phase constitutes the dispersed phase, and the emulsion is converted from the w/o type to the o/w type with an increase in the added amount of the water phase component, thereby accelerating the particulate formation of the oil phase.

The elimination of the organic solvent can be executed by the aforementioned method.

Thereafter, the microcapsules are collected by centrifugation or filtration if necessary, then washed several times with distilled water to eliminate the emulsifier etc. sticking on the surface of the microcapsules, and lyophilized after re-dispersion in distilled water. Otherwise the microcapsule slurry prepared in the foregoing steps may directly be dispersed in a suitable dispersion medium.

<Hollow Particulate Construct and Its Producing Method>

The hollow particulate construct of the present invention contains at least a bubble (hollow) therein and contains PHA in the outer coat (shell), and can assume configurations as explained above.

The hollow particulate construct of the present invention applicable to ultrasonic contrast medium can be prepared by solidifying PHA in the oil phase of a w/o emulsion of which oil phase containing an organic solvent and PHA, or of a w/o/w emulsion prepared by emulsifying the above w/o emulsion further in an external water phase, or of an o/w emulsion of which inner oil phase contains PHA and an organic solvent. For such microencapsulation, in-liquid drying, phase separation, spray drying or a similar method can be used, for example.

Alternatively, advantageously employed is a method of in vitro synthesis, where PHA synthesis is carried out in the water phase containing PHA synthesizing enzyme and 3-hydroxyacyl CoA, using a w/o emulsion, a w/o/w emulsion prepared by emulsifying the w/o emulsion in an external water phase which may also contain PHA synthesizing enzyme and 3-hydroxyacyl CoA, or an o/w emulsion of which external water phase contains PHA synthetase and 3-hydroxyacyl CoA.

There can also be advantageously employed a method of producing hollow particulate construct by carrying out PHA synthesis in the external water phase of a w/o/w emulsion, formed by emulsifying a w/o emulsion in an external water phase containing PHA synthetase and 3-hydroxyacyl CoA.

<Preparation of W/O Emulsion—Hollow Particulate Construct—>

The w/o emulsion, to be utilized in the preparation of the hollow particulate construct of the present invention and comprised of an inner water phase and an oil phase containing PHA, can be prepared in the following manner.

First, the inner water phase can be an aqueous solution of an inorganic or organic salt, in order to match the specific gravity with that of the organic solvent solution of the external oil phase. The inorganic salt can be, for example, calcium chloride, sodium chloride, potassium chloride, calcium bromide, sodium bromide, sodium carbonate, sodium hydrogen carbonate, potassium carbonate or potassium hydrogen carbonate. Also the organic salt can be, for example, sodium or potassium salt of an organic acid such as acetic acid, oxalic acid, citric acid, tartaric acid, succinic acid, phosphoric acid or ascorbic acid. Among these, an aqueous solution of calcium chloride is desirable in the present invention, in consideration of economy, ease of specific gravity matching and ease of washing. Such inorganic or organic salt is added to water in an amount of about 1 to 60 w/v %, preferably 20 to 50 w/v %, so as to match the specific gravity with that of the organic solvent solution of PHA. In this manner, by matching the specific gravity of the aqueous solution with that of the oil phase containing PHA, there can be obtained w/o emulsion in which the water droplets are uniformly dispersed in the oil phase.

Thus obtained aqueous solution subjected to the aforementioned specific gravity adjustment to be the inner water phase and a PHA-containing solution (oil phase) are mixed and emulsified to prepare a w/o emulsion. The emulsification can be achieved by a known method, for example intermittent vibration, agitation utilizing a mixer such as a propeller agitator or a turbine agitator, colloid mill method, homogenizer method or ultrasonic irradiation, or a combination thereof. The primary emulsification for preparing the w/o emulsion is important in ensuring the uniformity of the final microcapsule structure, since the water droplet diameter of the inner water phase of the w/o emulsion define the hollow portion of the hollow particulate construct to be formed and the external size thereof. It is therefore necessary, at this stage, to disperse the inner water phase as uniformly as possible in the organic solvent solution of PHA, in order to provide each hollow particulate construct with a single membrane hollow structure of a similar level. In addition, in order to use the prepared hollow particulate construct as an ultrasonic contrast medium, it is desirable to limit the external diameter of the hollow particulate construct not exceeding 10 μm. In consideration of these factors, it is preferred to reduce as small as possible the diameter of the water droplets of the inner water phase, so that it is advantageous to employ ultrasonic irradiation in combination with another dispersion method.

The aforementioned solution (oil phase) contains PHA dissolved in an organic solvent substantially immiscible with water. The solubility of such organic solvent in water does not preferably exceed 3 wt. % at normal temperature (20° C.). Also the boiling point of the organic solvent preferably does not exceed 120° C. Examples of the organic solvent include halogenated hydrocarbons (such as dichloromethane, chloroform, chloroethane, dichloroethane, trichloroethane, or carbon tetrachloride), ketones (such as acetone, methylethylketone, or methylisobutyl ketone), ethers (such as tetrahydrofuran, ethyl ether or isopropyl ether), esters (such as ethyl acetate or butyl acetate), and aromatic hydrocarbons (such as benzene, toluene or xylene), which may be employed in a mixture of two or more kinds. More preferably, the organic solvent is halogenated hydrocarbons (such as dichloromethane, chloroform, chloroethane, dichloroethane, trichloroethane, or carbon tetrachloride). The PHA concentration in the oil phase is variable depending on the kind and molecular weight of PHA and the kind of solvent, but is preferably within a range of about 0.01 to 80 wt. %, more preferably 0.1 to 70 wt. %, and most preferably 1 to 60 wt. %.

In order to vary the mutual solubility with the inner water phase, distribution of the organic solvent to the external water phase and evaporation of the organic solvent, the oil phase may be partly added with hydrophilic organic solvent such as ethanol, acetonitrile, acetone or tetrahydrofuran. Thus obtained oil phase by dissolving PHA may be filtered if necessary for eliminating bacteria and dust before use. Also, though dependent on the stability of PHA, the solution containing PHA may be stored in a tightly closed container at room temperature or in a cool place.

The mixing ratio of the aqueous solution and the organic solvent solution containing PHA is, with respect to 1 part by weight of the former, within a range of about 0.1 to 1000 parts by weight of the latter, preferably about 1 to 100 parts by weight.

<Preparation of W/O/W Emulsion and In-Liquid Drying—Hollow Particulate Construct—>

Then, thus obtained w/o emulsion is subjected to a hollow microencapsulation process. For example in case of hollow microencapsulation by in-liquid drying, the w/o emulsion is further added to water phase (hereinafter represented as external water phase) to prepare w/o/w emulsion, and the organic solvent in the oil phase is eliminated to obtain the hollow particulate construct.

The volume of the external water phase is generally selected within a range of about 1 to 10,000 times of that of the oil phase, preferably 2 to 5,000 times and more preferably 5 to 2,000 times.

The external water phase may be added with an emulsifier, which can be any emulsifier capable of forming stable w/o/w emulsion and which can be, for example, an anionic surfactant (such as sodium oleate, sodium stearate or sodium laurylsulfate), a nonionic surfactant [such as polyoxyethylene sorbitan fatty acid ester (Tween 80 or Tween 60, Atlas Powder, U.S.) or polyoxyethylene linseed oil derivative (HCO-70, HCO-60 or HCO-50, Nikko Chemicals, Japan)], polyvinyl pyrrolidone, polyvinyl alcohol, carboxymethyl cellulose, lecithine, gelatin, hyaluronic acid or derivatives thereof. These may be used singly or as a combination of plural kinds. The concentration of emulsifier in the external water phase is within a range of about 0.01 to 20 wt. %, preferably 0.05 to 10 wt. %.

The aforementioned external water phase may also be added with a permeation pressure adjusting agent, which can be any substance showing a permeation pressure in aqueous solution and of which examples include water-soluble polyhydric alcohols, water-soluble monohydric alcohols, water-soluble monosaccharides, disaccharides, oligosaccharides and derivatives thereof, water-soluble amino acids, water-soluble peptides, proteins and derivatives thereof.

The aforementioned water-soluble polyhydric alcohols include dihydric alcohols such as glycerin, pentahydric alcohols such as arabitol, xylitol or adonitol, hexahydric alcohols such as mannitol, sorbitol or zurcitol, among which preferred is hexavalent alcohol, particularly mannitol. The aforementioned water-soluble monohydric alcohols include methanol, ethanol and isopropyl alcohol, among which preferred is ethanol. The aforementioned water-soluble monosaccharides include 5-carbon sugars such as arabinose, xylose, ribose or 2-deoxyribose, and 6-carbon sugars such as glucose, fructose, galactose, mannose, sorbose, rhamnose or fucose, among which preferred are 6-carbon sugars. The aforementioned water-soluble disaccharides include maltose, cellobiose, α,α-trehalose, lactose and glucose, among which preferred are lactose and glucose. The aforementioned water-soluble oligosaccharides include trisaccharides such as maltotriose or raffinose, and tetrasaccharides such as stachyose, among which preferred are trisaccharides. The derivatives of the aforementioned water-soluble monosaccharides, disaccharides and oligosaccharides include glucosamine, galactosamine, glucuronic acid and galacturonic acid.

The aforementioned water-soluble amino acids include neutral amino acids such as glycine, alanine, valine, leucine, isoleucine, phenylalanine, tyrosine, tryptophan, serine, threonine, proline, hydroxyproline, cysteine or methionine, acidic amino acids such as aspartic acid or glutamic acid, and basic amino acids such as lysine, arginine or histidine. There may also be employed salts of such water-soluble amino acids with an acid (hydrochloric acid, sulfuric acid or phosphoric acid) or with an alkali (alkali metal such as sodium or potassium). The water-soluble peptides, proteins and derivatives thereof include casein, globulin, prolamine, albumin and gelatin.

Among the aforementioned permeation pressure adjusting agents, preferred are water-soluble polyhydric alcohols, and water-soluble monosaccharides, disaccharides, oligosaccharides and derivatives thereof, more preferably water-soluble polyhydric alcohols and water-soluble monosaccharides, and most preferably water-soluble polyhydric alcohols. Such permeation pressure adjusting agents may be used singly or in a combination of two or more. Such permeation pressure adjusting agent is used at such concentration that the permeation pressure of the external water phase is about $1/50$ to 5 times of that of physiological saline, preferably $1/25$ to 3 times. More specifically, the concentration of the permeation pressure adjusting agent in the external water phase is, in case of a nonionic substance, in a range of about 0.001 to 60 wt. %, preferably 0.01 to 40 wt. %, more preferably 0.05 to 30 wt. % and most preferably 1 to 10 wt. %. In case of an ionic substance, the permeation pressure adjusting agent is employed at a concentration obtained by dividing the above-mentioned concentration with the total ion value. The addition amount of the permeation pressure adjusting agent need not be below the solubility but can be partly in a suspended state.

In the emulsification of w/o emulsion into water, agitation is executed after w/o emulsion is dispersed in water. Agitation can be executed by any of the aforementioned emulsifying methods, but the use of a homogenizer is preferable in obtaining emulsion particles (microcapsules) of an organic solvent solution having a structure in which a single layer of organic solvent liquid phase incorporates water. In case of using the homogenizer, the agitation is executed at 100 to 100,000 rpm, preferably 1,000 to 50,000 rpm for 0.1 to 30 minutes, preferably 0.5 to 20 minutes.

By such operation, the diameter of the w/o emulsion drops in the external water phase is reduced. Thus, the agitation with the homogenizer is effective in reducing the diameter of the w/o emulsion droplets without changing the dispersion state of the water phase in the w/o emulsion droplets. It is important to reduce the diameter of w/o emulsion drops to 1~20 μm in order to obtain a single polymer membrane structure in the final fine particles. Then, the emulsion is let to stand in this state under agitation for example with a propeller agitator. In such state, since the inner water phase in the w/o emulsion drops is unstable, it is united to form a large single water droplet prior to the solidification of PHA. On the other hand, since the w/o emulsion itself is stabilized by the emulsifier in the external water phase, there is formed, as a result, a capsule structure in which the inner water phase is surrounded by a single layer of organic solvent solution phase of PHA.

For facilitating the formation of w/o emulsion drops having such capsule structure, it is preferred to suitably adjust the kind and amount of the salt in the inner water phase, concentration of polymer in the oil phase, temperature of the oil phase (w/o emulsion drops) and of the emulsifying external water phase, and the ratio of the oil phase and the water phase. In particular, the use of an inorganic salt in the inner water phase increases the surface tension of the inner water phase, thereby unstabilizing the water phase to cause uniting of the water phase in the w/o emulsion drops in the course of particle formation, whereby the proportion of the emulsion of single membrane structure increases.

In preparing w/o/w emulsion in the method of the present invention, the viscosity of the w/o emulsion is preferably adjusted within a range of 50 to 10,000 cp. The viscosity can be adjusted, for example by (1) adjustment of PHA concentration in the oil phase, (2) adjustment of ratio of water phase and oil phase, (3) adjustment of temperature of w/o emulsion, (4) adjustment of temperature of the external water phase, or (5) adjustment of temperature of w/o emulsion with a line heater or a cooler at the charging thereof into the external water phase. These methods may used singly or in combination. In these methods, there is only required that the viscosity of the w/o emulsion is within a range of 50 to 10,000 cp at the conversion thereof into w/o/w emulsion. In the above-mentioned method (1), the concentration to be adjusted of PHA in the oil phase cannot be uniquely determined as it is dependent on the types of PHA and organic solvent, but is preferably about 10 to 80 wt. %. In the above-mentioned method (2), the ratio to be adjusted of water phase and oil phase cannot be determined as it is dependent on the property of the oil phase etc., but preferably w/o=about 1 to 50 v/v %. In the above-mentioned method (3), the temperature to be adjusted of the w/o emulsion is for example within a range from about $-20°$ C. to the boiling point of the organic solvent, preferably 0 to 30° C., and more preferably 10 to 20° C. The viscosity adjustment of the w/o emulsion can be executed at the preparation thereof in case of (1) or (2). In case of the above-mentioned method (4), the temperature of the external water phase may be adjusted in advance at the addition thereto of the w/o emulsion so as to obtain a result similar to the above-mentioned method (3). The temperature of the external water phase is for example about 5 to 30° C., preferably 10 to 25° C. and more preferably 12 to 25° C.

The elimination of the organic solvent can be executed by a known method, such as a method of evaporating the organic solvent at normal pressure or at a gradually reduced pressure under agitation with a propeller agitator or a magnetic stirrer, or a method of evaporating the organic solvent under controlled vacuum and temperature for example in a rotary evaporator.

Thereafter, the fine particles are collected by centrifuging or filtration, then washed several times with distilled water to eliminate emulsifier etc. sticking on the surface of the fine particulate, and the remaining solvent and water are removed by drying under a reduced pressure or by lyophilization after re-dispersion in distilled water.

In case of re-dispersion in distilled water, a dispersant may be added. The dispersant has a function of preventing coagulation of the fine particles. The dispersant can be, for example, a Tween-80 like surfactant, sucrose fatty acid ester, mannitol, sorbitol, glucose, galactose or sucrose. Such dispersant is used by dissolving in water at a concentration of about 0.001 to 30 wt. %.

The generated fine particles having the single PHA membrane structure may be directly re-dispersed, but they may be centrifuged at a low speed after washing for separation into precipitate and non-precipitate, since they contain particles having porous structure. Such centrifugation is executed at a revolution of about 50~3,000 rpm for 1 to 60 minutes, and is preferably executed several times.

By the centrifugation, the hollow particulate constructs having the single membrane structure of PHA are collected in the non-precipitate phase. The ultrasonic contrast medium utilizing the hollow particulate construct of such single membrane structure exhibits a high ultrasonic contrast effect. Also for obtaining dry fine particles, there can be used drying under a reduced pressure with heating if necessary or lyophilization, but the latter is preferred.

In this manner obtained are hollow particulate construct of a particle diameter of 1 to 10 μm. As will be described in the following examples, the hollow particulate constructs have a spherical shape without pores on the capsule surface and containing a large proportion of hollow portion.

<Phase Separation—Hollow Particulate Construct—>

In case of preparation of hollow microcapsules by phase separation, a coacervation agent is gradually added to organic solvent solution of the drug and PHA at a constant rate under agitation, thereby precipitating and solidifying PHA and preparing hollow particulate construct. The coacervation agent can be any substance based on polymer, mineral oil or vegetable oil miscible with the solvent of PHA and not dissolving PHA for particulate formation, and can be, for example, silicone oil, sesame oil, soybean oil, corn oil, cotton seed oil, coconut oil, linseed oil, mineral oil, n-hexane, n-heptane, methanol or ethanol. These may also be employed in combination of two or more. Such coacervation agent is added in a volume amount of 0.01~1,000 times of the volume of the organic solvent solution of drug and PHA, preferably 0.1~200 times. The obtained microcapsules are acquired by filtration or centrifuging, then washed repeatedly with heptane etc. to eliminate the coacervation agent, and then subjected to the elimination of the washing liquid by heating or under a reduced pressure. If desired, the organic solvent is eliminated in a similar manner as in the aforementioned case of in-liquid drying.

<Spray Drying—Hollow Particulate Construct—>

In case of hollow microencapsulation by spray drying, the w/o emulsion or the w/o/w emulsion prepared in the same manner as in the in-liquid drying is sprayed from a nozzle into a drying chamber of a spray drier to evaporate the organic solvent and water in the pulverized liquid droplets within an extremely short time, thereby preparing the microcapsules in fine powder state. The nozzle can be a two-fluid nozzle, a pressurized nozzle or a rotary disk type. The obtained microcapsules are washed, if desired, several times with distilled water to eliminate the emulsifier sticking on the surface of the microcapsules. Then, the washed microcapsules may be subjected to elimination of the organic solvent by drying under a reduced pressure or by lyophilization after re-dispersion in distilled water.

<Preparation of O/W Emulsion—Hollow Particulate Construct—>

Preparation of hollow particulate construct by in-liquid drying from w/o emulsion is executed by dispersing an oil phase containing PHA and organic solvent in a water phase to form w/o emulsion, and then eliminating the solvent in the oil phase. The volume of the water phase is generally selected within a range of about 1 to 10,000 times of that of the oil phase, preferably 2 to 5,000 times and more preferably 5 to 2,000 times. Particularly preferable is about 50 to 1000 times. The temperature of the water phase may be adjusted in advance to about 5 to 30° C., preferably 10 to 25° C., more preferably 10 to 20° C. The water phase may be added with an emulsifier, which can be any emulsifier capable of forming stable o/w emulsion and the aforementioned emulsifiers can be advantageously employed. The concentration of emulsifier in the external water phase is within a range of about 0.001 to 20 w/v %, preferably 0.01 to 10 w/v %, and more preferably 0.05 to 5 w/v %. Also the aforementioned known mixing apparatus can be employed for the emulsification step.

The emulsification for preparing the w/o emulsion is important in ensuring the uniformity of the hollow structure of the final hollow particulate construct, since the liquid drop diameter of the oil phase defines the external size thereof and the structure of the hollow portion thereof. In order to provide each hollow particulate construct with the hollow structure of a similar level, it is necessary, at this stage, to disperse the internal oil phase containing PHA as uniformly as possible in the external water phase. For this purpose it is preferred to reduce as far as possible the diameter of the liquid drops of the internal oil phase, and there is advantageously employed ultrasonic irradiation combined with another dispersion method.

The supply of constituents in the preparation of o/w emulsion of the present invention can assume various modes according to the known technologies, such as a method of charging PHA solution in a container and adding water phase containing the emulsifier, a method of inverting the order of addition, or a method of continuously supplying both at a constant ratio. In case of mixing by rotation, the order mentioned at first is preferable. In such case, there is initially formed w/o emulsion in which the PHA constitutes the continuous phase and the water phase constitutes the dispersed phase, and the emulsion is converted from the w/o type to the o/w type with an increase in the added amount of the water phase component, thereby accelerating the particulate formation of the oil phase.

The elimination of the organic solvent can be executed by the aforementioned methods applicable for the w/o emulsion. Thereafter, the hollow particulate construct is collected by centrifuging or filtration, then washed several times with distilled water to eliminate emulsifier etc. sticking on the surface of the microcapsules, and lyophilized after re-dispersion in distilled water.

<In vitro Synthesis>

The process for producing particulate construct by in vitro synthesis includes at least a step of preparing w/o emulsion, or w/o/w emulsion from such w/o emulsion, or o/w emulsion, and a step of reacting 3-hydroxyacyl CoA with PHA synthetase to synthesize PHA.

The enzyme protein such as PHA synthetase is a polypeptide comprised of a plurality of amino acids, and shows hydrophilicity by amino acids having a free ionic group such as lysine, hystidine, arginine, aspartic acid or glutamic acid but also has hydrophobicity by amino acids having a free hydrophobic group such as alanine, valine, leucine, isoleucine, methionine, triptophane, phyenylalanine or proline and also by being an organic polymer. Therefore, though variable in the level, hydrophilicity and hydrohobicity can be exhibited at the water/oil interface.

Since the polarity and amount of surface charge and the hydrophobicity of PHA synthetase change depending on the pH, salt concentration and temperature of the reaction liquid (water phase), it is desirable to adjust the reaction liquid within a range permitted by the enzymatic activity. For example a decrease in the salt concentration allows to increase the charge amount of the PHA synthetase. Also a change in pH allows to increase the opposite charge. Also an increase in the salt concentrtion allows to increase the hydrophobicity. Also the solution conditions suitable for reaction can be selected by checking the charge state or the hydrophobicity of the PHA synthetase, by executing electrophoresis or wetting angle measurement in advance. It is also possible to determine the conditions by directly measuring the amount of the PHA synthetase present at the water/oil interface in the w/o emulsion, w/o/w emulsion or o/w emulsion. The amount present at the interface can be measured, for example, by preparing w/o emulsion, w/o/w emulsion or o/w emulsion with PHA synthetase solution of a known concentration and then measuring the concentration of free PHA synthetase in the water phase.

By defining 1 unit (U) of the amount of the PHA synthetase releasing 1 μmol/minute of CoA in the PHA synthesis reaction by polymerization of 3-hydroxyacyl CoA, the amount of enzyme to be used in the reaction is selected within a range of 10 to 1,000 U per 1 g of oil phase, preferably 50 to 500 U.

The particulate construct in which water phase is covered by PHA as the internal water phase is prepared by PHA synthesis at the water/oil interface in the reaction liquid containing the aforementioned PHA synthetase and 3-hydroxyacyl CoA serving as the raw material of the desired PHA. The aqueous phase in the aforementioned w/o or o/w emulsion should be constructed as a reaction system adjusted to the conditions capable of exhibiting the activity of the PHA synthetase, and is prepared with a buffer normally within a pH range of 5.5 to 9.0, preferably 7.0 to 8.5. However the condition may be set outside the aforementioned range, depending on the optimum pH or pH stability of the PHA synthetase to be employed. Such buffer can be selected suitably according to the desired pH range, as long as the activity of the employed PHA synthetase can be exhibited, but there can be advantageously employed ordinary buffer utilized in the biochemical reactions, such as acetic acid buffer, phosphoric acid buffer, potassium phosphate buffer, 3-(N-morpholino) propane sulfonic acid (MOPS) buffer, N-tris(hydroxymethyl) methyl-3-aminopropane sulfonic acid (TAPS) buffer, trishydrochloric acid buffer, glycin buffer, 2-(cyclohexylamino) ethane sulfonic acid (CHES) buffer etc. The concentration of the buffer is not particularly limited as long as the activity of the employed PHA synthetase can be exhibited, but is advantageously selected within a range of 5.0 mM to 1.0 M, preferably in a range of 0.1 to 0.2 M. The reaction temperature is suitably selected according the characteristics of the PHA synthetase to be employed, but is normally selected within a range of 4 to 50° C., preferably 20 to 40° C. However the condition may be set outside the aforementioned range, depending on the optimum temperature or the heat resistance of the PHA synthetase to be employed.

The reaction time, though dependent on the stability of the PHA synthetase to be employed, is normally within a range of 1 minute to 24 hours, more desirably 30 minutes to 3 hours. The concentration of 3-hydroxyacyl CoA in the reaction liquid is suitably selected within a range capable of exhibiting the activity of the PHA synthetase to be employed, but is normally selected within a range of 0.1 mM to 1.0 M, preferably 0.2 mM to 0.2 M. Since pH of the reaction liquid tends to become lower when the concentration of 3-hydroxyacyl CoA in the reaction liquid is high, it is preferable to have a higher concentration in the aforementioned buffer if a high concentration is selected for 3-hydroxyacyl CoA.

Also in the above-mentioned process, by varying in time the composition such as type and concentration of the 3-hydroxyacyl CoA in the aqueous reaction liquid, the monomer unit composition of the PHA constituting the particulate construct can be varied in a direction from the inner side to the outer side. In case forming a microcapsule structure, the monomer unit composition of PHA constituting the shell can be changed in a direction from the inner side to the outer side.

In such particulate construct showing change in the monomer unit composition, there can be assumed a microcapsule configuration in which the single-layered PHA shows continuous change in the composition, involves a gradient composition in the radial direction in the direction from the inner side to the outer side. Such configuration can be realized, for example in the course of synthesis of PHA, by adding 3-hydroxyacyl CoA of another composition.

There can also be another configuration, in which the PHA film has stepwise changes in the composition and the drug is covered by plural layers of PHA with different compositions. Such configuration can be realized for example by synthesizing PHA with a certain composition of 3-hydroxyacyl CoA, then collecting the microcapsules under preparation from the reaction liquid for example by centrifuging, and adding again reaction liquid having a different composition of 3-hydroxyacyl CoA.

In the foregoing there has been explained preparation of particulate construct from o/w emulsion and from w/o emulsion, but the particulate construct can be similarly prepared also from w/o/w emulsion. It is possible to include PHA synthetase and 3-hydroxyacyl CoA both in the internal water phase and in the external water phase, but it is also preferable to synthesize PHA only in the external water phase in order to elevate the drug trapping rate. The PHA synthetase and 3-hydroxyacyl CoA can be made present in the internal and external water phases in four combinations, but such combinations may be suitably selected in consideration of the drug trapping rate, drug release characteristics, and ease and cost of the process.

The particulate construct obtained in the aforementioned reaction is subjected, if necessary to a washing step. The washing method for the particulate construct is not particularly limited as long as it does not provide the particulate construct with a change undesirable for the object of preparation of the particulate construct such as microcapsules. For example, after collection by filtration, it is repeatedly washed with heptane or the like to eliminate the free drug and the solvent. Also the unnecessary components contained in the reaction liquid can be eliminated by precipitating the particulate construct by centrifugation and removing the supernatant. Further washing is possible by adding a washing agent, such as heptane, in which HPA is insoluble, and executing centrifugation. Further, the particulate construct may be subjected to a drying step if necessary, or to various secondary processes or chemical modification.

For example, by applying chemical modification to the PHA on the surface of the particulate construct such as microcapsules, there can be obtained the particulate construct having more useful functions and characteristics. For example by introducing a graft chain, there can be obtained particulate construct improved in various characteristics, derived from such graft chain, such as control of slow releasing ability or holding ability for the liquid or gaseous phase. Also by crosslinking the PHA on the surface of the particulate construct such as microcapsules, there can be improved the slow releasing ability or the holding ability of the liquid or gaseous phase.

The method of chemical modification is not particularly limited as long as it can attain the desired functions and structure, but there can be advantageously employed a method of synthesizing PHA having a reactive functional group in the side chain and executing chemical modification utilizing the chemical reaction of such functional group.

The type of the aforementioned reactive functional group is not particularly limited as long as it can attain the desired functions and structure, but the aforementioned epoxy group can be cited as an example. The PHA having an epoxy group in the side chain can be subjected to chemical conversion as in the ordinary polymer having an epoxy group. More specifically, there can be executed conversion into a hydroxyl group or introduction of a sulfon group. It is also possible to add a compound having thiol or amine, and, more specifically, the graft chain of the polymer can be formed by reaction under addition of a compound having an end amino group highly reactive with the epoxy group.

Examples of the compound having an amino group at the end include amino-modified polymers such as polyvinylamine, polyethylenimine or amino-modified polysiloxane (amino-modified silicone oil). Among these, amino-modified polysiloxane can be commercially available modified silicone oil or can be synthesized by the method described for example in J. Amer. Chem. Soc., 78, 2278(1956), and is expected to provide effects by the addition of a graft chain in the polymer, such as improvement in the control of the slow releasing function, holding function of the liquid or gaseous phase or self dispersibility in the aqueous solution.

Other examples of chemical conversion of the polymer having an epoxy group include crosslinking reaction with a diamine compound such as hexamethylene diamine, succinic anhydride or 2-ethyl-4-methylimidazole, and examples of physicochemical conversion include crosslinking reaction by electron beam irradiation. Among these, the reaction between PHA having an epoxy radical in the side chain and hexamethylene diamine proceeds in the following manner to produce crosslinked polymer:

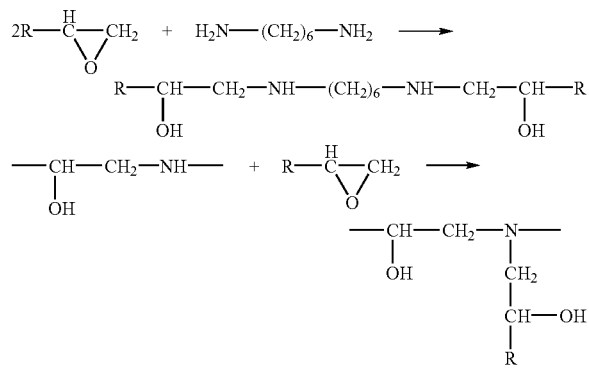

In the particulate construct thus obtained, the volume ratio of the internally incorporated portion in the entire particle is about 10 to 90%, but a range of about 35 to 85% is more preferred in consideration of the function, mechanical strength etc. of the particulate construct.

In the particulate construct such as microcapsules, the covering of the drug by PHA can be confirmed by a method of combining the composition analysis with gas chromatography and the morphological observation under an electron microscope, or a method of judging the structure by employing time of flight secondary ion mass spectrometer (TOF-SIMS) and ion sputtering thereby judging the structure from the mass spectrum of each constituent layer. However, for a more direct and simpler confirmation, there can be employed a method of combining dyeing with Nile blue A and observation under a fluorescence microscope, developed newly by the present inventors. As a result of intensive investigation for simple judgment of the PHA synthesis in a cellless (in vitro) system, the present inventors have found that Nile blue A, which generates fluorescence by specific bonding with PHA and is reported, in Appl. Environ. Microbiol., 44, 238-241 (1982), as usable for simple judgment of in vivo PHA production, can also be used for judging PHA synthesis in the cellless system by selecting suitable method and conditions of use, and have reached the above-mentioned method. In this method, the PHA synthesis in the cellless system can be easily judgd by mixing Nile blue A solution of a predetermined concentration, after filtration, with the reaction liquid containing PHA, irradiating excitation light of a predetermined wavelength and effecting observation under a fluorescence microscope of the fluorescence generated from the synthesized PHA alone. This method, applied to the preparation of the particulate construct of the present invention, allows to directly observe and evaluate the PHA covering the surface of the hydrophobic solution.

<Shape Forming Agent—Incorporating Hydrophilic Drug—>

The slow releasing preparation of the present invention preferably contains a shape forming agent, which is desirably little toxic upon administration in the living organism, easily dried by lyophilization or spray drying, and is dissolved promptly or when required upon administration into the living organism. Examples of such shape forming agent include sugars, cellulose derivatives, amino acids, proteins, polyacrylic acid derivatives, organic salts and inorganic salts. Such shape forming agent may be used in a mixture of two or more in a suitable proportion. Examples of sugar include D-mannitol, sodium arginate, fructose, dextran, dextrin, sucrose, D-sorbitol, lactose, glucose, maltose, starches and trehalose. Examples of cellulose derivative include carboxymethyl cellulose, hydroxypropyl cellulose, ethyl cellulose, hydroxymethyl cellulose, hydroxypropyl cellulose, cellulose acetate phthalate, hydroxypropylmethyl acetate phthalate, and hydroxymethyl cellulose acetate succinate. Examples of amino acid include glycine, alanine, tyrosine, arginine and lysine. Examples of protein include gelatin, fibrin, collagen and albumin. Examples of polyacrylic acid derivative include sodium polyacrylate, and methacrylic acid/acrylic acid copolymer (Eudragid; Rohm, Germany). Examples of organic salt include sodium citrate, sodium tartarate, sodium carbonate and potassium carbonate. Exampels of inorganic salt include sodium chloride, potassium chloride, sodium phosphate and potassium phosphate. In addition to the foregoing, the shape forming agent can also be water-soluble polymer which does not dissolve the polymer constituting the base material of the slow releasing preparation, such as polyvinylpyrrolidone or polyvinyl alcohol. The shape forming agent is preferably a sugar, particularly D-mannitol enabling easy lyophilization and showing low toxicity.

The amount of shape forming agent is determined by the solubility thereof, tension, viscosity, dispersibility and stability of the solution obtained by dissolving the shape forming agent, but is used in such a manner that, after drying the slow releasing preparation, the content of the shape forming agent therein is for example within a range of about 0.5 to 99 wt. %, preferably 1 to 90 wt. %, more preferably 2 to 60 wt. %. In case of using D-mannitol as the shape forming agent, it is particularly preferably that the content thereof in the dried slow releasing preparation is about 2 to 40 wt. %. The addition of such shape forming agent provides excellent effects such as 1) reducing frequency of contact and collision of the particles at and after the drying of the slow releasing preparation (particularly microspheres), and ensuring uniformity of the particles at the lyophilization or spray drying, 2) allowing drying of the slow releasing preparation at a temperature above the glass transition temperature, thereby enabling more complete elimination of water or organic solvent, and 3) improving the stability in time of the slow releasing preparation thereby providing the slow releasing preparation having satisfactory dispersibility and having a long period of use for example at room temperature not limited to storage in a cool place.

In the present invention, the slow releasing preparation containing the shape forming agent can be produced by mixing the particulate construct obtained by the aforementioned in-liquid drying, phase separation or spray drying and the shape forming agent. Such particulate construct may be dried under a reduced pressure after washing, or lyophilized by re-dispersing in distilled water after washing. The method of mixing is not particularly limited and is for example by the use of a mixer, but there is preferred a method of providing a uniform mixture. The slow releasing preparation containing the shape forming agent can also be produced, in the preparation of the particulate construct by spraying drying, by spraying aqueous solution of the shape forming agent from a separate nozzle at the spraying of the w/o emulsion. Also the slow releasing preparation containing the shape forming agent can also be produced, at the preparation of w/o/w emulsion to be used in in-water drying or in spray drying, by using aqueous solution of the shape forming agent as the external water phase. The slow releasing preparation containing the shape forming agent is preferably produced by washing the particulate construct obtained by in-water drying, phase separation or spray drying, dispersing the washed particulate construct in distilled water in which the shape forming agent is dissolved or dispersed, and subjecting the particulate construct to lyophilization or drying under a reduced pressure. It is also possible to disperse the washed particulate construct in distilled water, then dissolving or dispersing the shape forming agent in thus obtained dispersion, and executing lyophilization or drying under a reduced pressure. A particularly uniform mixture can be obtained by dispersing the washed particulate construct in distilled water in which the shape forming agent is dissolved or by dissolving the shape forming agent in dispersion obtained by dispersing the washed particulate construct in distilled water, and then executing lyophilization.

<Heating Process—Incorporating Hydrophilic Drug—>

The particulate construct, obtained by the aforementioned in-water drying, phase separation or spray drying, may be further heated, if desired, at a temperature equal to or exceeding the glass transition temperature (Tg) of PHA and not causing mutual sticking of the particles constituting the particulate construct, thereby eliminating water or organic solvent in the particulate construct more completely and improving the slow releasing ability. In such operation, the organic solvent is preferably eliminated to a level less than about 1000 ppm, preferably 500 ppm, more preferably 100 ppm. The heating is preferably executed after the addition of the shape forming agent if desired and after the lyophilization of drying under a reduced pressure of the particulate construct, but is not particularly restrictive and can be executed, for example, after the particulate construct is divided into small portions.

The heating at a temperature lower than the glass transition temperature of PHA may not achieve sufficient elimination of water or organic solvent, while that at an excessively high temperature increases the danger of fusion or deformation of the particulate construct, or decomposition or deterioration of the drug. Therefore, the heating temperature cannot be determined uniquely, but can be determined suitably in consideration of the physical properties (molecular weight, stability etc.) of PHA, drug, average particle size of particulate construct, heating time, level of drying of the particulate construct, heating method etc. The heating is preferably executed at a temperature at least equal to the glass transition temperature of PHA but not causing mutual sticking of the particulate construct. More preferably it is executed at a temperature within a range from the glass transition temperature of PHA to a temperature higher by about 30° C., and most preferably within a range from the glass transition temperature of PHA to a temperature higher by about 20° C. The heating time is variable depending on the heating temperature and the amount of the particulate construct to be processed, but is in general about 6 to 120 hours, preferably 12 to 96 hours after the particulate construct reaches the predetermined temperature. The upper limit of the heating time is not particularly limited as long as the remaining organic solvent or water becomes less than the permissible value, but it is desirable to promptly terminate the heating when the remaining orgnic solvent or water becomes less than the permissible limit since the particulate construct softens above the glass transition temperature and causes deformation by the physical contact of the particles or by the load under the compilation of the particles. The heating method is not particularly limited, and the heating can be executed by any method in which the particulate construct can be uniformly heated. Such heat drying can be achieved, for example, by heating in a thermostat, a flowing tank, a movable layer or a kirn, or by heating with microwave. Among these, there is preferred heat drying in a thermostat. The heating of the particulate construct under a reduced pressure after lyophilization allows to efficiently eliminate the organic solvent in the particulate construct, thereby providing particulate construct safe to the living organism. The remaining amount of the organic solvent in thus obtained particulate construct is about 100 ppm or less.

<Anticoagulant—Incorporating Oleophilic Drug—>

In the production by in-water drying, coacervation or in vitro synthesis, an anticoagulant may be added to distilled water used as the washing liquid, in order to prevent mutual coagulation of the particles in the course of washing. Such angicoagulant can be a water-soluble polysaccharide such as mannitol, lactose, glucose or starch (such as corn starch), or a protein such as glycine, fibrin or collagen, or an inorganic salt such as sodium chloride or sodium hydrophosphate.

<Spray Drying—Incorporating Oleophilic Drug—>

In case of preparation of the particulate construct such as microcapsules by spray drying, the solution or dispersion of the drug and PHA in organic solvent is sprayed from a nozzle into a drying chamber of a spray drier to evaporate the organic solvent in the pulverized liquid drops within an extremely short time, thereby preparing the particulate construct. The nozzle can be a two-fluid nozzle, a pressurized nozzle or a rotary disk type. If desired, it is also effective to spray aqueous solution of the aforementioned anticoagulant from a separate nozzle for preventing the coagulation of the particulate construct, simultaneously with the spraying of solution or dispersion of the drug and PHA in organic solvent. The obtained particulate construct is subjected, if necessary, to elimination of the water and the organic solvent by heating under a reduced pressure.

<Elimination of Organic Solvent—Incorporating Oleophilic Drug—>

The elimination of the organic solvent can be executed by a known method, such as a method of evaporating the organic solvent at normal pressure or at a gradually reduced pressure under agitation with a propeller agitator or a magnetic stirrer, or a method of evaporating the organic solvent under controlled vacuum and temperature for example in a rotary evaporator. In the in-liquid drying of o/w emulsion, the organic solvent is evaporated and the particulate construct is solidifed for example into microcapsules, thereby determining the structure of the particulate construct. Thus obtained particulate construct is collected by centrifuging or filtration, then washed several times with distilled water to eliminate free drug, drug retaining substance, emulsifier etc. sticking on the surface of the particulate construct, and lyophilized after re-dispersion in distilled water.

<Anticoagulant—Incorporating Oleophilic Drug—>

At the lyophilization, an anticoagulant may be added. Such angicoagulant can be a water-soluble polysaccharide such as mannitol, starch (such as corn starch), an inorganic salt, an amino acid or a protein among which preferred is mannitol. The mixing ratio (weight ratio) of the particulate construct and the anticoagulant is about 50:1 to 1:1, preferably 20:1 to 1:1, and more preferably 10:1 to 5:1. Also an anticoagulant may be added to distilled water used as the washing liquid, in order to prevent mutual coagulation of the particles in the course of washing. Such angicoagulant can be a water-soluble polysaccharide such as mannitol, lactose, glucose or starch (such as corn starch), or a protein such as glycine, fibrin or collagen, or an inorganic salt such as sodium chloride or sodium hydrophosphate. Preferred anticoagulant is mannitol.

<Heating Process—Incorporating Oleophilic Drug—>

After the lyophilization, there may be executed heating under a reduced pressure to further eliminate the water and organic solvent in the particulate construct, thereby improving the slow releasing property. The heating at a temperature lower than the glass transition temperature of PHA may not achieve improvement on the excessive initial release of the drug, while that at an excessively high temperature increases the danger of fusion or deformation of the particulate construct, or decomposition or deterioration of the drug. Therefore, the heating temperature cannot be determined uniquely, but can be determined suitably in consideration of the physical properties (molecular weight, stability etc.) of PHA, drug, average particle size of particulate construct, heating time, level of drying of the particulate construct, heating method etc. In such operation, the organic solvent is preferably eliminated to a level less than about 1000 ppm, preferably 500 ppm, more preferably 100 ppm.

The heating is preferably executed at a temperature at least equal to the glass transition temperature of PHA but not causing mutual sticking of the particulate construct. The slow releasing property can be improved by heating at a temperature within a range from the glass transition temperature of PHA to a temperature higher by about 30° C., more preferably within a range from the glass transition temperature of PHA to a temperature higher by about 10° C., and most preferably within a range from the glass transition temperature of PHA to a temperature higher by about 5° C. (in particular a temperature higher than the glass transition temperature by 3 to 4° C.). The heating time is variable depending on the heating temperature and the amount of the particulate construct to be processed, but is in general about 24 to 120 hours, preferably 48 to 120 hours, and more preferably 48 to 96 hours after the particulate construct reaches the predetermined temperature. The upper limit of the heating time is not particularly limited as long as the remaining organic solvent or water becomes less than the permissible value, but it is desirable to promptly terminate the heating when the remaining orgnic solvent or water becomes less than the permissible limit since the particulate construct softens above the glass transition temperature and causes deformation by the physical contact of the particles or by the load under the compilation of the particles.

The heating method is not particularly limited, and the heating can be executed by any method in which the particulate construct can be uniformly heated. Such heat drying can be achieved, for example, by heating in a thermostat, a flowing tank, a movable layer or a kirn, or by heating with microwave. Among these, there is preferred heat drying in a thermostat. The heating of the particulate construct under a reduced pressure after lyophilization allows to efficiently eliminate the organic solvent in the particulate construct, thereby providing particulate construct safe to the living organism. The remaining amount of the organic solvent in thus obtained particulate construct is about 100 ppm or less.

<Substance Contained in Oil or Water Phase—Incorporating Liquid Phase—>

The substance borne by the microcapsules is suitably selected according to the application of the microcapsules of the present invention.

In case the microcapsules of the present invention are used for an agricultural drug composition, there may be used any substance described in the Agricultural drug handbook (Japanese Botanical Antiepidemic Association), such as carbamate pesticides, organic phosphor-based pesticides, pyrethroid pesticides, urea pesticides, anylide bacteriocides, azole bacteriocides, or dicarboxyimide bacteriocides.

In case the microcapsules of the present invention are used for a fertilizer composition, the substance to be borne therein can be aqueous solution of nitroge-based fertilizer such as ammonium sulfate, ammonium nitrate, ammonium chloride, urea, acetoaldehyde-condensed urea or isobutylaldehyde-condensed urea, aqueous solution of phosphoric acid-based fertilizer such as calcium perphosphate, calcium biperphosphate or fused phosphor fertilizer, aqueous solution of potassium-based fertilizer such as potassium sulfate or potassium chloride, aqueous suspension of organic fertilizer such as fish lees, bone powder, syobean oil lees etc., aqueous solution or three-element composite fertilizer such as ammonium phosphate or potassium phosphate, or aqueous solution of trace element composite fertilizer.

In case the microcapsules of the present invention are used for a cosmetic product, the substance to be borne therein can be enzymes such as a moisturizing component, a herb extract, tyrosinase, sparoxydedimustase or lipase, vitamins such as retinol, ascorbic acid, tocopherol, pyridoxal or riboflavin, organic dyestaffs such as beta-carotin or chlorophyl, moisturing components such as glycerin, sorbitol, urea, lactic acid, propylene glycol, polyethylene glycol, copolymers thereof or glucose derivatives, emolient components such as paraffin, stearyl alcohol, cetyl alcohol, squalane, silicone oil or stearis, treatment components, antidandruff components, hair nourishing components, ultraviolet absorbers, antioxidants or fragrances.

In case the microcapsules of the present invention are used as artificial hemocytes, the substance to be borne therein can be hemoglobin or hemocyanine.

In case the microcapsules of the present invention are used for ink or paint, the substance to be borne therein can be aqueous solution of dyes or aqueous suspension of pigments, more specifically acidic dyes such as C.I. acid red 52, C.I. acid blue 1, C.I. acid black 2 or 123; basic dyes such as C.I. basic blue 7 or C.I. basic red 1; direct dyes such as C.I. direct black 19 or C.I. direct blue 86; oil-soluble dyes such as C.I. solvent black 7 or 123, C.I. solvent red 8, 49 or 100, C.I. solvent blue 2, 25, 55 or 70, C.I. solvent green 3, C.I. solvent yellow 21 or 61, C.I. solvent orange 37, C.I. solvent violet 8 or 21; reactive dyes such as C.I. reactive yellow 15 or 42, C.I. reactive red 24 or 218, C.I. reactive blue 38 or 220; black pigments such as carbon black, copper oxide, manganese dioxide, aniline black, activated carbon, nonmagnetic ferrite, and magnetite; yellow pigments such as chrome yellow, zinc yellow, yellow iron oxide, cadmium yellow, mineral fast yellow, nickel titanium yellow, navels yellow, naphtol yellow S, Hansa yellow G, Hansa Yellow 10G, benzidine yellow G, benzidine yellow GR, quinoline yellow lake, permanent yellow NCG, and tartrazine lake; orange pigments such as red chrome yellow, molybdenum orange, permanent orange GTR, pyrazolone orange, vulkan orange, benzidine orange G, indanthrene brilliant orange RK, and indanthrene brilliant orange GK; red pigments such as red iron oxide, cadmium red lead, mercury sulfide, cadmium, permanent red 4R, lithol red, pyrazolone red, watching red, calcium salt, lake red C, lake red D, brilliant carmine 6B, brilliant carmine 3B, eosin lake, rhodamine lake B, and alizarin lake; blue pigments such as iron blue, cobalt blue, alkali blue lake, victoria blue lake, copper phthalocyanine blue, metal-free phthalocyanine blue, partly chlorinated phthalocyanine blue compound, fast sky blue, and indanthrene blue BC; purple pigments such as manganese purple, fast violet B, and methyl violet lake; green pigments such as chromium oxide, chrome green, pigment green B, malachite green lake, and final yellow green G; white pigments such as zinc oxide, titanium oxide, and zinc sulfide; extender pigments such as barytes, barium carbonate, clay, white carbon, talc, and alumina white, but such examples are naturally not restrictive.

In case the microcapsules of the present invention are used for slow drug release, the drug to be borne therein can be an easily water-soluble drug or a hardly water-soluble (oil-soluble) drug. Such drug can be sterols (for example cholesterol or cytosterol), estrogens (for example estrone, estradiol, esters thereof or ethinylestradiol), colticoids and esters, peptide hormones such as calcytonine, antibiotics (for example gentamycin, vancomycin, amicacine, canamycin, streptomycin, minocyclin or tetramycin), chloramphenicol, macrolide antibiotics (for example ethythromycin or derivatives thereof, particularly palmitate or stearate thereof, or spiramycin), antiparasite germ drugs and dermal drugs (for example chlotrimazole, miconazole or dithranol), antiinframmatory antalgics (for example indomethacine, dichlophenac, flurubiprophene, ketoprophene, 4-biphenylacetic acid or ethyl ester thereof), vitamins such as cyanovalamine, enzyme drugs such as urokinase, anticancer drugs such as fluorouracyl or alacytidine.

<Shape Forming Agent—Incorporating Gaseous Phase—>

The ultrasonic contrast medium prepared utilizing the hollow particulate construct of the present invention may contain a shape forming agent, which is desirably little toxic upon administration in the living organism, easily dried by lyophilization or spray drying, and is dissolved promptly or when required upon administration into the living organism. Examples of such shape forming agent include sugars, cellulose derivatives, amino acids, proteins, polyacrylic acid derivatives, organic salts and inorganic salts. Such shape forming agent may be used in a mixture of two or more in a suitable proportion.

Examples of sugar include D-mannitol, sodium arginate, fructose, dextran, dextrin, sucrose, D-sorbitol, lactose, glucose, maltose, starches and trehalose. Examples of cellulose derivative include carboxymethyl cellulose, hydroxypropylmethyl cellulose, ethyl cellulose, hydroxymethyl cellulose, hydroxypropyl cellulose, cellulose acetate phthalate, hydroxypropylmethyl acetate phthalate, and hydroxymethyl cellulose acetate succinate.

Examples of amino acid include glycine, alanine, tyrosine, arginine and lysine. Examples of protein include gelatin, fibrin, collagen and albumin. Examples of polyacrylic acid derivative include sodium polyacrylate, and methacrylic acid/acrylic acid copolymer (Eudragid; Rohm, Germany). Examples of organic salt include sodium citrate, sodium tartarate, sodium carbonate and potassium carbonate. Exampels of inorganic salt include sodium chloride, potassium chloride, sodium phosphate and potassium phosphate. In addition to the foregoing, the shape forming agent can also be water-soluble polymer which does not dissolve PHA, such as polyvinylpyrrolidone or polyvinyl alcohol. The shape forming agent is preferably a sugar, particularly D-mannitol enabling easy lyophilization and showing low toxicity.

The amount of shape forming agent is determined by the solubility thereof, tension, viscosity, dispersibility and stability of the solution obtained by dissolving the shape forming agent, but is used in such a manner that, after drying the slow releasing preparation, the content of the shape forming agent therein is for example within a range of about 0.5 to 99 wt. %, preferably 1 to 90 wt. %, more preferably 2 to 60 wt. %. In case of using D-mannitol as the shape forming agent, it is particularly preferably that the content thereof in the dried ultrasonic contrast medium is about 2 to 40 wt. %. The addition of such shape forming agent provides excellent effects such as 1) reducing frequency of contact and collision of the particles at and after the drying of the ultrasonic contrast medium (particularly microspheres), and ensuring uniformity of the particles at the lyophilization or spray drying, 2) allowing drying of the ultrasonic contrast medium at a temperature above the glass transition temperature, thereby enabling more complete elimination of water or organic solvent, and 3) improving the stability in time of the ultrasonic contrast medium thereby providing the ultrasonic contrast medium having satisfactory dispersibility and having a long period of use for example at room temperature not limited to storage in a cool place.

In the present invention, the ultrasonic contrast medium containing the shape forming agent can be produced by mixing the particulate construct obtained by the aforementioned in-liquid drying, phase separation or spray drying and the shape forming agent. Such hollow particulate construct may be dried under a reduced pressure after washing, or lyophilized by re-dispersing in distilled water after washing. The method of mixing is not particularly limited and is for example by the use of a mixer, but there is preferred a method of providing a uniform mixture. The ultrasonic contrast medium containing the shape forming agent can also be produced, in the preparation of the hollow particulate construct by spraying drying, by spraying aqueous solution of the shape forming agent from a separate nozzle at the spraying of the w/o emulsion. Also the ulrasonic contrast medium containing the shape forming agent can also be produced, at the preparation of w/o/w emulsion to be used in in-water drying or in spray drying, by using aqueous solution of the shape forming agent as the external water phase. The ultrasonic contrast medium containing the shape forming agent is preferably produced by washing the hollow particulate construct obtained by in-water drying, phase separation or spray drying, dispersing the washed hollow particulate construct in distilled water in which the shape forming agent is dissolved or dispersed, and subjecting the hollow particulate construct to lyophilization or drying under a reduced pressure. It is also possible to disperse the washed hollow particulate construct in distilled water, then dissolving or dispersing the shape forming agent in thus obtained dispersion, and executing lyophilization or drying under a reduced pressure. A particularly uniform mixture can be obtained by dispersing the washed hollow particulate construct in distilled water in which the shape forming agent is dissolved or by dissolving the shape forming agent in dispersion obtained by dispersing the washed hollow particulate construct in distilled water, and then executing lyophilization.

<Heating Process—Incorporating Gaseous Phase—>

The hollow particulate construct, obtained by the aforementioned in-water drying, phase separation or spray drying, may be further heated, if desired, at a temperature equal to or exceeding the glass transition temperature (Tg) of PHA and not causing mutual sticking of the particles constituting the particulate construct, thereby eliminating water or organic solvent in the hollow particulate construct more completely and improving the gas retaining ability. In such operation, the organic solvent is preferably eliminated to a level less than about 1000 ppm, preferably 500 ppm, more preferably 100 ppm. The heating is preferably executed after the addition of the shape forming agent if desired and after the lyophilization or drying under a reduced pressure of the hollow particulate construct, but is not particularly restrictive and can be executed, for example, after the particulate construct is divided into small portions.

The heating at a temperature lower than the glass transition temperature of PHA may not achieve sufficient elimination of water or organic solvent, while that at an excessively high temperature increases the danger of fusion or deformation of the particles of the hollow particulate construct. Therefore, the heating temperature cannot be determined uniquely, but can be determined suitably in consideration of the physical properties (molecular weight, stability etc.) of PHA, average particle size of hollow particulate construct, heating time, level of drying of the hollow particulate construct, heating method etc. The heating is preferably executed at a temperature at least equal to the glass transition temperature of PHA but not causing mutual sticking of the particulate construct. More preferably it is executed at a temperature within a range from the glass transition temperature of PHA to a temperature higher by about 30° C., and most preferably within a range from the glass transition temperature of PHA to a temperature higher by about 20° C.

The heating time is variable depending on the heating temperature and the amount of the hollow particulate construct to be processed, but is in general about 6 to 120 hours, preferably 12 to 96 hours after the hollow particulate construct reaches the predetermined temperature. The upper limit of the heating time is not particularly limited as long as the remaining organic solvent or water becomes less than the permissible value, but it is desirable to promptly terminate the heating when the remaining orgnic solvent or water becomes less than the permissible limit since the hollow particulate construct softens above the glass transition temperature and causes deformation by the physical contact of the particles or by the load under the compilation of the particles.

The heating method is not particularly limited, and the heating can be executed by any method in which the hollow particulate construct can be uniformly heated. Such heat drying can be achieved, for example, by heating in a thermostat, a flowing tank, a movable layer or a kirn, or by heating with microwave. Among these, there is preferred heat drying in a thermostat. The heating of the hollow particulate construct under a reduced pressure after lyophilization allows to efficiently eliminate the organic solvent in the particulate construct, thereby providing hollow particulate construct safe to the living organism. The remaining amount of the organic solvent in thus obtained hollow particulate construct is about 100 ppm or less.

<Application—Incorporating Hydrophilic Drug—>

The drug to be employed in the present invention is not particularly limited and can be one or more selected from a group consisting of physiologically active polypeptides, antibiotics, antieumycetes agents, antihyperkemia agents, circulatory drugs, anti-blood platelet agents (blood platelet coagulation suppressors, anti-blood-clot agents, styptics, antitumor agents, antipyretics, antalgics, antiinflammatory agents, antitussive expceterants, sedatives, amyotonic agents, antiepilepsy agents, antiulcer agents, antidepression agents, antiallergic agents, cardiotonicums, antiarhythmia agents, vasodilators, diuretics, antidiabetic agents, hormons, antituberculosis agents, antinarcotics, bone absorption suppressors, osteogenesis accelerators, vasogenesis inhibitors etc. but particularly preferred are water-soluble drugs.

<Preparation—Incorporating Hydrophilic Drug—>

The slow releasing preparation of the present invention can be comprised of the particulate construct of the present invention such as microcapsules or can be formed therefrom into various forms of preparation, such as an injection preparation, an embedded preparation, an oral preparation (such as powder, granules, capsule, tablet, syrup, emulsion or suspension), a nasal preparation or a suppository (rectum suppository or vagina suppository). Such preparations can be produced by known methods ordinarily employed in the field of pharmaceutrical prepations. For example, the injection preparation can be produced by dispersing the aforementioned particulate construct in aqueous or oily dispersion medium. The aqueous dispersion medium can be solution in distilled water of a tension equalizing agent (such as sodium chloride, glucose, D-mannitol, sorbitol or glycerin), a dispersant (such as Tween 80, HCO-50, HCO-60, carboxymethyl cellulose or sodium arginate), a storing agent (such as benzyl alcohol, benzalconium chloride or phenol) or a pain reducing agent (such as glucose, calcium gluconate or procain hydrochlorinate). Also the oily dispersion medium can be olive oil, sesame oil, peanut oil, soybean oil, corn oil or medium chain fatty acid glyceride. Such injection preparation may be filled in the chamber of a prefilled syringe, or the dispersion medium and the particulate construct may be separately filled in the different chambers of so-called double chamber prefilled syringe (DPS). Also in the preparation of the injection preparation, there can be obtained more stable slow releasing preparation by adding a shape forming agent (such as mannitol, sorbitol, lactose or glucose) to the particulate construct of the above-mentioned composition, and, after re-dispersion, solidifying the mixture by lyophilization or spray drying and adding distilled water for injection or a suitable dispersion medium at the use. The particle size in the use as a suspension injection preparation is only required to meet the required level of dispersion and to pass the injection needle, and the average particle size is for example within a range of about 0.1 to 500 μm, preferably 1 to 300 μm and more preferably 2 to 200 μm. Also the particulate construct can be made into a spherical shape suitable for passing the injection needle, by adding a permeation pressure adjusting gent to the water phase as explained in the foregoing. An aseptic preparation can be obtained from the particulate construct for example by rendering all the producing process aseptic, sterilyzing with gamma ray or adding an aseptic, but such method is not restrictive.

The oral preparation can be prepared by adding, to the aforementioned particulate construct, a shape forming agent (such as lactose, white sugar or starch), a breaking agent (such as starch or calcium carbonate), a binder (such as starch, gum Arabic, carboxymethyl cellulose, polyvinyl pyrrolidone or hydroxypropyl cellulose), a lubricant (such as talc, magnesium stearate or polyethylene glycol 6000) etc., then executing compressing molding and, if necessary, coating by a known method for the purpose of taste masking, intestinal dissolvability or efficacy duration. For the coating, there can be employed, for example, hydroxypropylmetyl cellulose, ethyl cellulose, hydroxymethyl cellulose, hydroxypropyl cellulose, polyoxyethylene glycol, Tween 80, Pluronic F68, cellulose acetatephthalate, hydroxypropylmethyl cellulose phthalate, hydroxymethyl cellulose acetate succinte Eudrogid methacrylic acid-acrylic acid copolymer (Rohm, Germany), or a pigment (such as titanium oxide or Indian red).

The nasal preparation can be solid, semi-solid or liquid. The solid nasal preparation can be comprised of the particulate construct itself, such as the microcapsules mentioned above, but can generally be produced by adding and mixing, to such particulate construct, a shape forming agent (such as glucose, mannitol, starch or microcrystalline cellulose) a viscosifier (such as matural gums, cellulose derivatives or acrylic acid polymer). Also the liquid nasal preparation can be produced in a similar manner as the aforementioned injection preparation. Also such nasal preparation may contain a pH adjusting agent (such as carbonic acid, phosphoric acid, citric acid, hydrochloric acid, or sodium hydroxide), an antiseptic (such as paraoxybenzoic acid esters, chlorobutanol or benzalconium chloride). The suppository can be oily or aqueous, and can be solid, semi-solid or liquid. The suppository is usually produced with an oily base material, an aqueous base material or an aqueous gel base material. The oily base material can be, for example, a higher fatty acid glyceride [such as cacao fat or Witepsols (Dynamite Nobel, Germany)], a medium fatty acid (such as Migriols (Dynamite Nobel, Germany) or vegetable oil (such as sesame oil, soybean oil, or cotton seed oil). The aqueous base material can be polyethylene glycols or propylene glycols. The aqueous gel base material can be natural gums, cellulose derivatives, vinylic polymers or acrylic acid polymers.

The slow releasing preparation of the present invention is of low toxicity and can be used safely in the mammals (such as man, cow, pig, dog, cat, mouse, rat or hare). The amount of administration of the slow releasing preparation is variable depending on the type and content of the drug, type of preparation, duration of drug release, object desease [for example prostate cancer, prostate hypertrophy, endometritis, myoma of uterus, premature puberty, bladder cancer, breast cancer, cervical canal cancer, chronic lymphatic leukemia, chronic myeloid leukemia, colon cancer, gastritis, Hodgkins's desease, but malignant melanoma, transition, multiple myeloid tumor, non-Hodgkin lymphatic tumor, non-cellule lung cancer, ovarian cancer, digestive ulcer, total eumycetes infection, cellule lung cancer, valvular desease, mastopathia, polycystic ovarian, sterility, ovalation induction in female chronic non-ovalation, acne, amenorrhea (for example successive amenorrhea), polycystic deseases in ovarian and breast (including polycystic ovarian), gynecologic cancers, ovarian hyperandrogenemia and hypertrichosis, AIDS by T cell generation through infantile thymus, remedy for hormone dependent deseases such as male birth control for the remedy of male sexual criminal and birth control, suppression of premensual symptoms (PMS), fecundation (IVF) etc.] and object animal, but should be within the effective amount of such drug. The amount of administration per time of the drug, for example in case of a slow releasing preparation for a month, can be suitably selected within a range of about 0.01 to 100 mg/kg per body weight of adult, more preferably 0.05 to 50 mg/kg, most preferably 0.1 to 10 mg/kg. The amount of administration per time of the slow releasing preparation can be suitably selected within a range of about 0.1 to 500 mg/kg per body weight of adult, more preferably 0.2 to 300 mg/kg. The frequency of administration can be suitably selected such as once every several weeks, once every month or once every several months, depending on the type and content of the drug, type of preparation, duration of drug release, object desease and object animal.

<Application—Incorporating Oleophilic Drug—>

The drug to be employed in the present invention is not particularly limited and can be one or more selected from a group consisting of physiologically active polypeptides, antibiotics, antieumycetes agents, antihyperkemia agents, circulatory drugs, anti-blood platelet agents (blood platelet coagulation suppressors, antitumor agents, antipyretics, antalgics, antiinflammatory agents, antitussive expcetorants, sedatives, amyotonic agents, antiepilepsy agents, antiulcer agents, antidepression agents, antiallergic agents, cardiotonicums, antiarhythmia agents, vasodilators, diuretics, antidiabetic agents, hormons, and bone absorption suppressors, but particularly preferred are hardly water-soluble drugs. For example, there can be advantageously employed steroid drugs, protein drugs, peptide drugs, 5-fluorouracil, Me-CCUN, omeprazole or anticancer drugs such as platina preparations (specifically cysplatin, carboplatin, isoplatin or modified substances thereof).

<Preparation—Incorporating Oleophilic Drug—>

The slow releasing preparation of the present invention can be comprised of the particulate construct of the present invention such as microcapsules or can be formed therefrom into various forms of preparation, such as an injection preparation, an embedded preparation, an oral preparation (such as powder, granules, capsule, tablet, syrup, emulsion or suspension), a nasal preparation or a suppository (rectum suppository or vagina suppository). Such preparations can be produced by known methods ordinarily employed in the field of pharmaceutrical prepations. For example, the injection preparation can be produced by dispersing the aforementioned particulate construct in aqueous or oily dispersion medium. The aqueous dispersion medium can be solution in distilled water of a tension equalizing agent (such as sodium chloride, glucose, D-mannitol, sorbitol or glycerin), a dispersant (such as Tween 80, HCO-50, HCO-60, carboxymethyl cellulose or sodium arginate), a storing agent (such as benzyl alcohol, benzalconium chloride or phenol) or a pain reducing agent (such as glucose, calcium gluconate or procain hydrochlorinate). Also the oily dispersion medium can be olive oil, sesame oil, peanut oil, soybean oil, corn oil or medium chain fatty acid glyceride. Such injection preparation may be filled in the chamber of a prefilled syringe, or the dispersion medium and the particulate construct may be separately filled in the different chambers of so-called double chamber prefilled syringe (DPS). Also in the preparation of the injection preparation, there can be obtained more stable slow releasing preparation by adding a shape forming agent (such as mannitol, sorbitol, lactose or glucose) to the particulate construct of the above-mentioned composition, and, after re-dispersion, solidifying the mixture by lyophilization or spray drying and adding distilled water for injection or a suitable dispersion medium at the use. The particle size in the use as a suspension injection preparation is only required to meet the required level of dispersion and to pass the injection needle, and the average particle size is for example within a range of about 0.1 to 500 μm, preferably 1 to 300 μm and more preferably 2 to 200 μm. Also the particulate construct can be made into a spherical shape suitable for passing the injection needle, by adding a permeation pressure adjusting gent to the water phase as explained in the foregoing. An aseptic preparation can be obtained from the particulate construct for example by rendering all the producing process aseptic, sterilyzing with gamma ray or adding an aseptic, but such method is not restrictive.

The oral preparation can be prepared by adding, to the aforementioned particulate construct, a shape forming agent (such as lactose, white sugar or starch), a breaking agent (such as starch or calcium carbonate), a binder (such as starch, gum Arabic, carboxymethyl cellulose, polyvinyl pyrrolidone or hydroxypropyl cellulose), a lubricant (such as talc, magnesium stearate or polyethylene glycol 6000) etc., then executing compressing molding and, if necessary, coating by a known method for the purpose of taste masking, intestinal dissolvability or efficacy duration. For the coating, there can be employed, for example, hydroxypropylmetyl cellulose, ethyl cellulose, hydroxymethyl cellulose, hydroxypropyl cellulose, polyoxyethylene glycol, Tween 80, Pluronic F68, cellulose acetatephthalate, hydroxypropylmethyl cellulose phthalate, hydroxymethyl cellulose acetate succinte Eudrogid methacrylic acid-acrylic acid copolymer (Rohm, Germany), or a pigment (such as titanium oxide or Indian red).

The nasal preparation can be solid, semi-solid or liquid. The solid nasal preparation can be comprised of the particulate construct itself, such as the microcapsules mentioned above, but can generally be produced by adding and mixing, to such particulate construct, a shape forming agent (such as glucose, mannitol, starch or microcrystalline cellulose) a viscosifier (such as matural gums, cellulose derivatives or acrylic acid polymer). Also the liquid nasal preparation can be produced in a similar manner as the aforementioned injection preparation. Also such nasal preparation may contain a pH adjusting agent (such as carbonic acid, phosphoric acid, citric acid, hydrochloric acid, or sodium hydroxide), an antiseptic (such as paraoxybenzoic acid esters, chlorobutanol or benzalconium chloride). The suppository can be oily or aqueous, and can be solid, semi-solid or liquid. The suppository is usually produced with an oily base material, an aqueous base material or an aqueous gel base material. The oily base material can be, for example, a higher fatty acid glyceride [such as cacao fat or Witepsols (Dynamite Nobel, Germany)], a medium fatty acid (such as Migriols (Dynamite Nobel, Germany) or vegetable oil (such as sesame oil, soybean oil, or cotton seed oil). The aqueous base material can be polyethylene glycols or propylene glycols. The aqueous gel base material can be natural gums, cellulose derivatives, vinylic polymers or acrylic acid polymers.

The slow releasing preparation of the present invention is of low toxicity and can be used safely in the mammals (such as man, cow, pig, dog, cat, mouse, rat or hare). The amount of administration of the slow releasing preparation is variable depending on the type and content of the drug, type of preparation, duration of drug release, object desease [for example prostate cancer, prostate hypertrophy, endometritis, myoma of uterus, premature puberty, bladder cancer, breast cancer, cervical canal cancer, chronic lymphatic leukemia, chronic myeloid leukemia, colon cancer, gastritis, Hodgkins's desease, but malignant melanoma, transition, multiple myeloid tumor, non-Hodgkin lymphatic tumor, non-cellule lung cancer, ovarian cancer, digestive ulcer, total eumycetes infection, cellule lung cancer, valvular desease, mastopathia, polycystic ovarian, sterility, ovalation induction in female chronic non-ovalation, acne, amenorrhea (for example successive amenorrhea), polycystic deseases in ovarian and breast (including polycystic ovarian), gynecologic cancers, ovarian hyperandrogenemia and hypertrichosis, AIDS by T cell generation through infantile thymus, remedy for hormone dependent deseases such as male birth control for the remedy of male sexual criminal and birth control, suppression of premensual symptoms (PMS), fecundation (IVF) etc.] and object animal, but should be within the effective amount of such drug. The amount of administration per time of the drug, for example in case of a slow releasing preparation for a month, can be suitably selected within a range of about 0.01 to 100 mg/kg per body weight of adult, more preferably 0.05 to 50 mg/kg, most preferably 0.1 to 10 mg/kg. The amount of administration per time of the slow releasing preparation can be suitably selected within a range of about 0.1 to 500 mg/kg per body weight of adult, more preferably 0.2 to 300 mg/kg. The frequency of administration can be suitably selected such as once every several weeks, once every month or once every several months, depending on the type and content of the drug, type of preparation, duration of drug release, object desease and object animal.

<Application—Incorporating Liquid Phase—>

In case of utilizing the microcapsules of the present invention as a fertilizer composition, it is possible to use the slurry, obtained in the course of microencapsulation, directly as the agricultural drug composition, but it is also possible to form an easily usable preparation such as aqueous suspension, aqueous preparation, powder or granules, and aqueous suspension is particularly preferred. Such aqueous suspension can be prepared by adding stabilizers such as a viscosifier, antifreezing agent, a specific gravity adjusting agent, an antiseptic etc. to the microcapsule slurry obtained as described above. The viscosifier to be used can be, for example, polysaccharides such as carboxymethyl cellulose, xanthana gum, lamzan gum, locust bean gum, caraginane or wellan gum, synthetic polymers such as sodium polyacrylate, mineral powder such as aluminum magnesium silicate, smectite, bentonite, hectolite or dry process silica, or alumina sol. The antifreezing agent can be alcohols such as propylene glycol. The specific gravity adjusting agent can be water-soluble salts such as sodium sulfate or urea.

In case of utilizing the microcapsules of the present invention for example as an agricultural drug composition, it is possible to use the slurry, obtained in the course of microencapsulation, directly as the agricultural drug composition, but it is also possible to form an easily usable preparation such as aqueous suspension, aqueous preparation, powder or granules, and aqueous suspension is particularly preferred. Such aqueous suspension can be prepared by adding stabilizers such as a viscosifier, antifreezing agent, a specific gravity adjusting agent, an antiseptic etc. to the microcapsule slurry obtained as described above. The viscosifier to be used can be, for example, polysaccharides such as carboxymethyl cellulose, xanthana gum, lamzan gum, locust bean gum, caraginane or wellan gum, synthetic polymers such as sodium polyacrylate, mineral powder such as aluminum magnesium silicate, smectite, bentonite, hectolite or dry process silica, or alumina sol. The antifreezing agent can be alcohols such as propylene glycol. The specific gravity adjusting agent can be water-soluble salts such as sodium sulfate or urea.

In case of utilizing the microcapsules of the present invention for example as a cosmetic composition, it can be produced by dispersion in a known cosmetic base material for example hydrocarbons such as solid or liquid paraffin, crystal oil, cerecin, ozokelite or montan wax; vegetable or animal oil, fat or wax such as olive oil, ground wax, carnauba wax, lanorin or whale wax; fatty acids and esters thereof such as stearic acid, palmitic acid, oleic acid, glycerin monostearate ester, glycerin distearate ester, glycerin monooleate ester, isopropylmyristic acid ester, isopropylstearic acid ester or butylstearic acid ester; silicones such as methylpolysiloxane, methylpolycyclosiloxane, methylphenylolysiloxane, or silicone polyether copolymer; alcohols such as ethanol, isopropyl alcohol, cetyl alcohol, stearyl alcohol, palmityl alcohol or hexyldodecyl alcohol; polyhydric alcohols having moisturizing effect such as glycol, glycerin or sorbitol.

In case the microcapsules of the present invention are used as an artificial hemocyte composition, the slurry obtained in the microencapsulation process is suspended in physiological saline, and large particles are eliminated by a known method such as gel filtration or centrifugation.

In case the microcapsules of the present invention are used as an ink composition, they are dispersed in an aqueous medium. In order to facilitate dispersion into the aqueous medium, there may be added a surfactant, a protective colloid, water-soluble organic solvent etc. within a range not significantly deteriorating the water resistance of the coating. There may also be added an antiseptic, a viscosity adjusting agent, a pH adjusting agent, a chelating agent etc. Examples of the protective colloid which can be added to the aqueous pigment ink of the present invention include natural proteing such as glue, gelatin, casein, alubmin, gum Arabic, or fish glue, and synthetic polymers such as arginic acid, methyl cellulose, carboxymethyl cellulose, polyethylene oxide, hydroxyethyl cellulose, polyvinyl alcohol, polyacrylamide, aromatic amides, polyacrylic acid, polyvinylether, polyvinylpyrrolidone, acrylic resin or polyester. The protective colloid is used if necessary in order to improve fixability, viscosity and rapid drying property, and the proportion of the protective colloid in the ink preferably does not exceed 30 mass %, more preferably 20 mass %.

The surfactant that can be added to the aqueous pigment ink of the present invention may be anionic, cationic, amphoteric or nonionic. Examples of the anionic surfactant include fatty acid salts such as sodium stearate, potassium oleate or semi-hardened bovine fatty acid sodium salt; alkylsulfonic acid ester salts such as sodium dodecylsulfate, tri(2-hydroxyethyl)ammonium dodecylsulfate, or sodium octadecylsulfate; benzenesulfonic acid salts such as sodium nonylbenzenesulfonate, sodium dodecylbenzenesulfonate, sodium octadecylbenzenesulfonate, or sodium dodecyldiphenyletherdisulfonate; naphthalenesulfonic acid salts such as sodium dodecylnaphthalenesulfonate or naphthalenesulfonic acid-formalin condensate; sulfosuccinic acid ester salts such as sodium didodecyl sulfosuccinate or sodium dioctadecyl sulfosuccinate; polyoxyethylenesulfuric acid ester salts such as sodium polyoxyethylene dodecylether sulfate, tri(2-hydroxyethyl)ammonium polyoxyethylene dedecylether sulfate, sodium polyoxyethylene octadecylether sulfate, or sodium polyoxyethylene dodecylphenylether sulfate; and phosphoric acid ester salts such as potassium dodecylphosphate or sodium octadecylphosphate. Examples of the cationic surfactant include alkylamine salts such as octadecylammonium acetate or palm oil amine acetic acid salt; and quaternary ammonium salts such as chlorododecyltrimethyl ammonium, chlorooctadecyltrimethyl ammonium, chlorodioctadecyldimethyl ammonium, or chlorododecylbenzyldimethyl ammonium. Examples of the amphoteric surfactant include alkylbetains such as dodecylbetain, or octadecylbetain; and amine oxides such as dodecyldimethylamine oxide. Examples of the nonionic surfactant include polyoxyethylene dodecylethers such as polyoxyethylene dodecylether, polyoxyethylene hexadecylether, polyoxyethylene octadecylether or polyoxyethylene (9-octadecenyl) ether; polyoxyethylene phenylethers such as polyoxyethylene oxctylphenylether, or polyoxyethylene nonylphenylether; oxilane polymers such as polyoxidized ethylene, copoly-oxiethyleneoxipropylene; sorbitan fatty acid esters such as sorbitandodecanoic acid ester, sorbitanoctadecanoic acid ester, sorbitan(9-octadecenoic acid) ester, sorbitan(9-octadecenoic acid) triester, polyoxyethylene-sorbitandodecanoic acid ester, polyoxyethylene-sorbitanoctadecanoic acid ester, polyoxyethylene-sorbitanoctadecanoic acid triester, polyoxyethylene-sorbitan (9-octadecenoic acid) ester or polyoxyethylene-sorbitan (9-octadecenoic acid) triester; sorbitol fatty acid esters such as polyoxyethylene-sorbitan (9-octadecenoic acid) tetraester; and glycerin fatty acid esters such as glycerin octadecanoic acid ester or glycerin (9-octadecenoic acid) ester. Among such nonionic surfactants, particularly preferred are those having HLB at least equal to 14. The amount of addition of the aforementioned surfactant in the present invention is variable depending upon whether a single surfactant is used or two or more surfactants are used in combination, but is within a range of 0 to 10 mass %, preferably 0 to 5 mass % with respect to the entire amount of the ink composition. The aqueous pigment ink composition of the present invention preferably contains water in 20 to 95 mass % and pigment in 1 to 60 volume %.

<Perfluorocarbon—Incorporating Gaseous Phase—>

Perfluorocarbon gas can be filled in the hollow portion of the hollow particulate construct of the present invention to be utilized as an ultrasonic contrast medium, by dispersing the hollow particulate construct in water, then drying it under a reduced pressure in a drying apparatus, then introducing perfluorocarbon gas into the drier being in a reduced pressure state and returning pressure preferably to the normal pressure.

The water in which the hollow particulate construct is dispersed may contain the aforementioned dispersant. Reduced pressure drying can be achieved by drying under a reduced pressure with heating if necessary or by lyophilization, but the latter is preferred. Perfluorocarbon has a boiling temperature not exceeding body temperature, preferably not exceeding 10° C., in order to maintain the gaseous state even after administration of the contrast medium into the body. Such perfluorocarbon can be, for example, octafluorocyclobutane, octafluoropropane, hexafluoroethane etc. The perfluorocarbon gas to be used is preferably hardly soluble in water, whereby it would not dissolve in the body fluid such as blood and the duration of the contrast enhancing effect can be prolonged.

<Aqueous Carrier—Incorporating Gaseous Phase—>

The hollow particulate construct obtained by the method of the present invention, being in a dry, fine particulate state, is dispersed in a suitable aqueous carrier (phisiological saline or an aqueous mannitol solution) and is administered into the body orally or non-orally, at the use as the ultrasonic contrast medium. Such aqueous carrier may also contain a known dispersant if necessary. In the use as the ultrasonic contrast medium, the hollow particulate construct is added to a concentration of 0.01 to 80%, preferably 0.01 to 50% with respect to the entire amount of the contrast medium including the aqueous carrier.

EXAMPLES

Now the present invention will be described in more detail with reference to Examples. Although each of the examples described below is the best mode of the present invention, the technical scope of the present invention is not limited to these examples. "%" or "part" herein is based on the weight unless otherwise specified. "Microcapsules" herein include the aforementioned two configurations, namely one layer (monolithic) type and two layer (core/shell) type, which will be collectively called microcapsules.

Reference Example 1

Construction of Transformant Having PHB Synthetase Production Capacity

Construction of transformant having PHB synthetase production capacity, derived from TB 64 strain was separately applied for patent by the present inventors, but a specific example thereof will be explained in the following. Strain TB64 was cultured in 100 ml of LB medium (1% polypeptone, 0.5% yeast extract, 0.5% sodium chloride, pH 7.4) overnight at 30° C., then the chromosomal DNA was isolated by the method of Marmar et al. The obtained DNA was partially digested by a restriction enzyme Sau3AI. A vector pUC18 was also cut by a restriction enzyme BamHI. After terminal dephosphorylation (Molecular Cloning, 1, 572, (1989); Cold Spring Harbor Laboratory Press), Sau3AI partial digestion fragments of the chromosomal DNA were ligated to the cleavage site of the vector using a DNA ligation kit Ver. II (TAKARA SHUZO CO., LTD.). With these ligated chromosomal DNA fragments, *Escherichia coli* HB 101 was transformed to construct a DNA library of strain TB64.

Next, to obtain DNA fragments covering the PHB synthetase gene of strain TB64, a representative screening was carried out. LB culture medium containing 2% glucose was used for screening, and Sudan black solution was sprayed when the colony on the flat agar culture medium grew to a suitable size, and a colony showing fluorescence under UV light irradiation was collected. The DNA fragments covering the PHB synthetase gene could be obtained by recovering plasmid from the acquired colony with the alkali method.

The acquired gene fragment was transformed into a vector pBBR122 having a wide-host-replication range (Mo Bi Tec) not belonging to any of IncP, IncQ, or IncW incompatibility group. When Ralstogna eutropha TB64 ml strain (lacking PHA synthesis negative strain) was transformed with this recombinant plasmid by electroporation, the PHA synthesizing capacity of the TB64 ml strain was recovered to show complementarity.

Then an oligonucleotide having the base sequence in the vicinity of starting codon of the PHB synthetase gene was designed and synthesized (Amarsham Farmacia Biotech), and PCR was carried out by using the nucleotid as a primer to amplify the fragment including the PHB synthetase gene (LA-PCR kit; TAKARA SHUZO).

The obtained PCR fragment was completely digested by a restriction enzyme BamHI. A vector pTrc99A was also cut by BamHI. After terminal dephosphorylation (Molecular Cloning, 1, 572, (1989); Cold Spring Harbor Laboratory Press), complete BamHI digestion fragments were ligated using a DNA ligation kit Ver. II (TAKARA SHUZO CO., LTD.). With the obtained transformant plasmid vectors, *Escherichia coli* HB 101 was transformed by calcium chloride method (TAKARA SHUZO) to recover a transformant plasmid pTB 64-PHB from the obtained transformant. Then, with pTB 64-PHB, *Escherichia coli* HB 101 was transformed by calcium chloride method to obtain a pTB 64-PHB transformant strain.

Reference Example 2

Construction of Transformant Having GST Fused PHB Synthetase Production Capacity The pTB 64-PHB transformant strain was inoculated in 200 ml of an LB medium, and incubated at 37° C., with shaking at 125 strokes/min. The cells were harvested by centrifugation and plasmid DNA was recovered by the normal method.

Then, an upstream primer (SEQ ID NO: 1) and a downstream primer (SEQ ID NO: 2) to pTB 64-PHB were synthesized respectively (Amarsham Pharmacia Biotech). Using these oligonucleotids as primers, PCR was carried out by using pTB 64-PHB as a template to amplify a full length of PHB synthetase gene having a BamHI restriction site at the upstream side and an XhoI restrction site at the downstream side (LA-PCR kit; TAKARA SHUZO CO., LTD.).

Respective purified PCR amplification products were digested by BamHI and XhoI, then inserted into the corresponding restriction sites of plasmid pGEX-6P-1 (Amersham Pharmacia Biotech). An *E. coli* strain JM109 was transformed with these vectors, and consequently a strain expressing PHA synthetase was obtained. For confirmation, the plasmid DNA was prepared by Miniprep (Wizard Minipreps DNA Purification Systems, PROMEGA) in a large amount and digested by BamHI and XhoI, and the resulting DNA fragment was identified.

Reference Example 3

Production of PHB Synthetase

The obtained expression strain was pre-cultured overnight at 30° C. in 100 mL of 2xYT culture medium (polypeptone 16 g/L, yeast extract 10 g/L, NaCl 5 g/L, pH 7.0) added with ampicillin (100 μg/L).

Then it was added to 10 liters of 2xYT culture medium (polypeptone 16 g/L, yeast extract 10 g/L, NaCl 5 g/L, pH 7.0) added with ampicillin (100 μg/L) and culture was executed for 3 hours at 30° C. Then isopropyl-β-D-thiogalactopyranocide (IPTG) was added to obtain a final concentration of 1 mM, and the culture was executed for 3 hours at 30° C.

The recovered culture liquid was centrifuged for 10 minutes at 4° C., 78000 m/s2 (=8000 G), and, after the elimination of supernatant, the bacteria pellet was re-suspended in 500 mL of PBS solution at 4° C. The bacteria liquid was poured, 40 mL each time, in a vessel cooled to 4° C. in advance, and, under pressurization of 216 MPA (=2200 kg/cm2) by a French press, the bacteria liquid was released little by little from the nozzle, thereby executing bacteria crushing process. The crushed bacteria liquid was centrifuged for 10 minutes at 4° C., 78000 m/s2 (=8000 G), and the supernatant was recovered. The liquid was filtered with a filter of 0.45 μm to eliminate the solids. The presence of the desired PHB synthesizing enzyme fused with glutathion transferase (GST) in the supernatant was confirmed by SDS-PAGE.

Then the GST-fused PHB synthesizing enzyme was purified with glutathion sepharose 4B (Amarsham Farmacia Biotech Inc.). 6.65 mL of 75% slurry of glutathion sepharose 4B was centrifuged for 5 minutes at 4° C., 4900 m/s2 (=500 G), and, after the elimination of supernatant, it was re-suspended in 200 mL of PBS solution at 4° C. Centrifuging was executed again for 5 minutes at 4° C., 4900 m/s2 (=500 G), and the supernatant was eliminated. Then it was re-suspended in 5 mL of PBS solution at 4° C. to obtain 50% slurry of glutathion sepharose 4B.

The entire amount of the supernatant was added to 10 mL of thus obtained 50% slurry of glutathion sepharose 4B, and the mixture was mildly shaken to cause the desired fused protein in the supernatant to be affinity absorbed by glutathion sepharose 4B.

The liquid was centrifuged for 5 minutes at 4° C., 4900 m/s2 (=500 G), and, after the elimination of supernatant, it was re-suspended in 5 mL of PBS solution at 4° C., and subjected to similar centrifuging again and the supernatant was eliminated. The glutathion sepharose 4B on which GST-fused PHB synthesizing enzyme was fixed was rinsed by repeating re-suspension in PBS solution and centrifuging twice, and was finally suspended in 5 mL of Cleavage buffer (Tris-HCl 50 mM, NaCl 150 mM, EDTA 1 mM, dithiothreitol 1 mM, pH 7). Then 0.5 mL of 4% solution of prescission protease (Amarsham Farmacia Biotech) in cleavage buffer, and the mixture was mildly shaken for 4 hours at 5° C. The mixture was centrifuged for 5 minutes at 4° C., 4900 m/s2 (=500 G), and the supernatant was recovered. Then 1 mL of 50% slurry of glutathion sepharose 4B prepared as explained in the foregoing was centrifuged for 5 minutes at 4° C., 4900 m/s2 (=500 G), and the above recovered supernatant was added to glutathion sepharose 4B after the elimination of supernatant, and the mixture was mildly agitated to cause glutation sepharose 4B to absorb prescission protease remaining in the supernatant. Then centrifuging was executed for 5 minutes at 4° C., 4900 m/s2 (=500 G), and, the supernatant was recovered. The supernatant showed a single band in SDS-PAGE, indicating the purification.

The activity of the contained PHB synthesizing enzyme was measured in the following manner. At first bovine serum albumin (Sigma Co.) was dissolved in 0.1 M tris hydrochloric acid buffer (pH 8.0) in 3.0 mg/mL, and 100 μL of thus obtained solution was added to 100 μL of enzyme solution and the mixture was pre-incubated for 1 minute at 30° C. Then 100 μL of solution of 3-hydroxybutyryl CoA dissolved in 0.1 M tris hydrochloric acid buffer (pH 8.0) in 3.0 mM was added, then the mixture was incubated for 1 to 30 minutes at 30° C., and then the reaction is terminated by adding solution of trichloroacetic acid dissolved in 0.1 M tris hydrochloric acid buffer (pH 8.0) at 10 mg/mL. The solution after termination of reaction was centrifuged (147,000 m/s2 (15,000 G), 10 minutes), and 500 μL of 2 mM solution of 5,5'-dithiobis-(2-nitrobenzoic acid) dissolved in 0.1 M tris hydrochloric acid buffer (pH 8.0) was added, and, Second reaction (color developing reaction of free CoA): centrifuged (147,000 m/s2 (15,000 G), 10 minutes), and 500 μL of the supernatant is added with 500 μL of the reagent 4 and, after incubation for 10 minutes at 30° C., the optical absorbance at 412 nm was measured. The enzyme activity was calculated by taking an enzyme amount causing release of CoA of 1 μmol in 1 minute as 1 unit (U). As a result there was obtained a relative activity of 7.5 U/mL. The obtained liquid was concentrated by ultrafiltration under the addition of Reiho gel to 10 U/mL, thereby obtaining purified enzyme liquid (1).

Reference Example 4

Preparation of Crude Enzyme Liquid Containing PHB Synthesizing Enzyme

The KK01 and TL2 strains were cultured for 24 hours at 30° C. in 100 liters of M9 culture medium (following composition) containing 0.5% of yeast extract and 0.3% of mineral solution (see following), and the recovered culture liquid was centrifuged for 10 minutes at 4° C., 78000 m/s2 (=8000 G), and, after the elimination of supernatant, the bacteria pellet was re-suspended in 500 mL of PBS solution at 4° C. The bacteria liquid was poured, 40 mL each time, in a vessel cooled to 4° C. in advance, and, under pressurization of 2200 kg/cm2 by a French press, the bacteria liquid was released little by little from the nozzle, thereby executing bacteria crushing process. The crushed bacteria liquid was centrifuged for 10 minutes at 4° C., 78000 m/s2 (=8000 G), and the supernatant was recovered. The liquid was filtered with a filter of 0.45 μm to eliminate the solids, and the activity of the contained PHB synthesizing enzyme was measured by the aforementioned method. As a result there were obtained relative activities of 1.6 U/mL for the KK01 strain and 1.2 U/mL for the TL2 strain. The liquid was concentrated by ultrafiltration under the addition of an organism solution specimen condenser (trade name: Mizubutorikun; Ato Co.) to 10 U/mL, thereby obtaining purified enzyme liquid (1) derived from the KK01 strain and (2) derived from the TL2 strain.

[M9 Culture Medium]

| | |
|---|---|
| Na$_2$HPO$_4$: | 6.2 g |
| KH$_2$PO$_4$: | 3.0 g |
| NaCl: | 0.5 g |
| NH$_4$Cl: | 1.0 g |
| (per liter, pH 7.0) | |
| [Mineral solution] | |
| Nitrilotriacetic acid: | 1.5 g |
| MgSO$_4$: | 3.0 g |
| MnSO$_4$: | 0.5 g |
| NaCl: | 1.0 g |
| FeSO$_4$: | 0.1 g |
| CaCl$_2$: | 0.1 g |
| CoCl$_2$: | 0.1 g |
| ZnSO$_4$: | 0.1 g |
| CuSO$_4$: | 0.1 g |
| AlK(SO$_4$)$_2$: | 0.1 g |
| H$_3$BO$_3$: | 0.1 g |
| Na$_2$MoO$_4$: | 0.1 g |
| NiCl$_2$: | 0.1 g |
| (per liter) | |

Reference Example 5

Construction of Transformant Having PHA Synthetase Production Capacity

Strain YN2 was cultured in 100 ml of LB medium (1% polypeptone (NIPPON SEIYAKU CO., LTD.), 0.5% yeast extract (Difco), 0.5% sodium chloride, pH 7.4) overnight at 30° C., then the chromosomal DNA was isolated by the method of Marmar et al. The obtained DNA was completely digested by a restriction enzyme HindIII. A vector pUC18 was also cut by HindIII. After terminal dephosphorylation (Molecular Cloning, 1, 572, (1989); Cold Spring Harbor Laboratory Press), complete HindIII digestion fragments of the chromosomal DNA were ligated to the HindIII cleavage site of the vector (a cloning site) using a DNA ligation kit Ver. II (TAKARA SHUZO CO., LTD.). With these plasmid vectors containing chromosomal DNA fragments, *Escherichia coli* HB 101 was transformed to construct a DNA library of strain YN2. Next, to select DNA fragments covering the PHA synthetase gene of strain YN2, a probe for colony hybridization was prepared by synthesizing an oligonucleotide comprised of the base sequences of SEQ ID NO: 3 and SEQ ID NO: 4 (Amersham Pharmacia Biotech). Then PCR was carried out by using the chromosomal DNA as a template. The PCR-amplified DNA fragments were used as a probe. Labeling of the probe was conducted by employing a commercially available labeling enzyme Alk Phos Direct (Amersham Pharmacia Biotech). Using the obtained labeled probe for colony hybridization, a clone carrying the recombinant plasmid containing the PHA synthetase gene was selected from the chromosomal DNA library of YN2. The plasmid was recovered from the selected clone by the alkali process to give DNA fragment including the PHA synthetase gene. This gene fragment was inserted into a vector pBBR122 having a wide-host-replication range (Mo Bi Tec) not belonging to any of IncP, IncQ, or IncW incompatibility group. When *Pseudomonas cichorii* YN2ml (a PHA synthesis negative strain) was transformed with this recombinant plasmid by electroporation, the PHA synthesizing capacity of the YN2ml strain was recovered to show complementarity. Consequently, it was confirmed that the selected gene fragment contains PHA synthetase gene region which can be translated into PHA synthetase within Pseudomonas cichorii YN2ml.

The base sequence of this DNA fragment was determined by the Sanger method. As a result, it was shown that there are base sequences represented by SEQ ID NO: 5 and SEQ ID NO: 6 each encoding a polypeptide in the determined base sequence. With respect to these PHA synthetase genes, PCR was carried out by using the chromosomal DNA as a template to produce the complete PHA synthetase gene. More specifically, an upstream primer (SEQ ID NO: 7) and a downstream primer (SEQ ID NO: 8) corresponding to the PHA synthetase gene of SEQ ID NO:6, and an upstream primer (SEQ ID NO: 9) and a downstream primer (SEQ ID NO: 10) corresponding to the PHA synthetase gene of SEQ ID NO: 6 were synthesized respectively (Amersham Pharmacia Biotech).

Using these primers, PCR was carried out for each of the 6 base sequences shown by SEQ ID NO: 5 and SEQ ID NO: 6, then a full length of PHA synthetase gene was amplified (an LA-PCR kit; TAKARA SHUZO CO., LTD.). Next, the obtained PCR amplified fragment and an expression vector pTrc99A were digested by the restriction enzyme HindIII and dephosphorylated (Molecular Cloning, vol. 1, p. 572, (1989); Cold Spring Harbor Laboratory Press), then the DNA fragment including a full length PHA synthetase gene excluding unnecessary base sequences at both terminuses was linked to a restriction site of the expression vector pTrc99A by using a DNA ligation kit Ver. II (TAKARA SHUZO CO., LTD.).

An E. coli strain (Escherichia coli HB101: TAKARA SHUZO) was transformed with each of the obtained recombinant plasmids by the calcium chloride method. The obtained recombinants were cultured and the recombinant plasmids were amplified, then the recombinant plasmids were respectively recovered. The recombinant plasmid having a DNA of SEQ ID NO: 5 was designated as pYN2-C1, and the recombinant plasmid having a DNA of SEQ ID NO: 6 was designated as pYN2-C2. An E. coli strain (Escherichia coli HB101fB fadB deletion strain) was transformed with pYN2-C1 and pYN2-C2 respectively by the calcium chloride method to obtain recombinant E. coli strains having respective recombinant plasmids, i.e., a pYN2-C1 recombinant strain and a pYN2-C2 recombinant strain.

Reference Example 6

Production of PHA Synthetase (1)

For the pYN2-C1, an upstream primer (SEQ ID NO: 11) and a downstream primer (SEQ ID NO: 12) were designed and synthesized respectively (Amersham Pharmacia Biotech). PCR was carried out with LA-PCR kit (TAKARA SHUZO CO., LTD.) using these primers and template pYN2-C1 to synthesize a full length PHA synthetase gene having a BamHI restriction site upstream and a XhoI restriction site downstream.

Similarly, for pYN2-C2, an upstream primer (SEQ ID NO: 13) and a downstream primer (SEQ ID NO: 14) were designed and synthesized respectively (Amersham Pharmacia Biotech). PCR was carried out with an LA-PCR kit (TAKARA SHUZO CO., LTD.) using these primers and the template pYN2-C2 to amplify the full length PHA synthetase gene having a BamHI restriction site upstream and a XhoI restriction site downstream.

Respective purified PCR amplification products were digested by BamHI and XhoI, then inserted into the corresponding restriction sites of plasmid pGEX-6P-1 (Amersham Pharmacia Biotech). An E. coli strain JM109 was transformed with these vectors, and consequently a strain expressing PHA synthetase was obtained. For confirmation, the plasmid DNA was prepared by Miniprep (Wizard Minipreps DNA Purification Systems, PROMEGA) in a large amount and digested by BamHI and XhoI, and the resulting DNA fragment was identified. The PHS synthetase was expressed and purified as follows: The obtained strain was pre-cultured in 10 ml of LB-Amp medium overnight, and then an 0.1 ml culture was transferred to 10 ml of LB-Amp medium and cultured at 37° C., 170 rpm for 3 hours with shaking. Then, IPTG was added to the culture to a concentration of 1 mM, then the culture was continued for 4 to 12 hours at 37° C.

The E. coli cells induced with IPTG were collected (8,000× g, 2 min., 4° C.) and resuspended in a 1/10 volume of phosphate buffer physiological saline (PBS; 8 g NaCl, 1.44 g $Na_2HPO_4$, 0.24 g $KH_2PO_4$, 0.2 g, KCl, 1,000 ml purified water) at 4° C. The cells were disrupted by freeze and thawing and sonication, and subjected to centrifugation (8,000×g, 10 min., 4° C.) to remove solid impurities. Confirming that the aimed recombinant protein was present in the supernatant by SDS-PAGE, the induced and expressed GST fusion protein was purified by using Glutathione Sepharose 4B (Amersham Pharmacia Biotech). The Glutathione Sepharose was previously treated to avoid nonspecific adsorption, that is, the Glutathione Sepharose was washed with an equivalent amount of PBS for three times (8,000×g, 1 min., 4° C.), and then an equivalent amount of 4% bovine serum albumin PBS was added thereto at 4° C. for one hour. After that, the Sepharose was washed with an equivalent amount of PBS twice, and re-suspended in a 1/2 amount of PBS. The pretreated 40 µl of Glutathione Sepharose was added to 1 ml of the above cell free extract, and gently stirred at 4° C. to adsorb fusion protein GST-YN2-C1 and GST-YN2-C2 onto Glutathione Sepharose respectively. After centrifugation (8,000× g, 1 min., 4° C.) to collect the Glutathione Sepharose, it was washed with 400 µl of PBS for three times. After the washing, 10 mM of glutathione was added thereto and stirred for one hour at 4° C. to elute the adsorbed fusion protein. After centrifugation (8,000×g, 2 min., 4° C.), the supernatant was recovered and dialyzed against PBS to purify the GST fusion protein. Single band was recognized by SDS-PAGE.

Then 500 µg of each GST fusion protein was digested by PreScission protease (Amersham Pharmacia Biotech, 5U), the protease and the GST were removed therefrom by passing through Glutathione Sepharose. The flow-through fraction was further loaded to Sephadex G200 column equilibrated with PBS, then expression proteins YN2-C1 and YN2-C2 were obtained as final purified products. By SDS-PAGE, single bands (60.8 kDa and 61.5 kDa, respectively) were confirmed.

The above-described enzymes were concentrated with a bioliquid concentrating agent (Mizubutorikun AB-1100, Atto Corp.) to obtain 10 U/ml of purified enzyme solutions.

The enzyme activity was measured by the above-described method. The protein concentration of the sample was determined by using a micro BCA protein assay reagent kit (Pierce Chemical Co.). The results are shown in Table 1.

TABLE 1

|  | Activity | Specific activity |
| --- | --- | --- |
| pYN2-C1 | 2.1 U/ml | 4.1 U/mg protein |
| pYN2-C2 | 1.5 U/ml | 3.6 U/mg protein |

Reference Example 7

Production of PHA Synthetase (2)

Each of E Coli strains P91, H45, YN2, and P161 was inoculated in 200 ml of an M9 medium containing 0.5% of yeast extract (Difco) and 0.1% of octanoic acid, and incubated at 30° C., with shaking at 125 strokes/min. After 24 hours, the cells were harvested by centrifugation (10,000×g, 4° C., for 10 min.), then the cells were re-suspended in 200 ml of 0.1M Tris-HCl buffer (pH 8.0) and further subjected to centrifugation for washing. The cells were re-suspended in 2.0 ml of 0.1M Tris-HCl buffer (pH 8.0) and disrupted by an ultrasonic homogenizer and then centrifuged (12,000×g, 4° C., for 10 min.) to collect the supernatant to obtain the crude enzyme.

Each crude enzyme activity was measured by the above-described method, and the result is shown in Table 2.

TABLE 2

|  | Origin | Activity |
|---|---|---|
| P91 | Strain P91 | 0.1 U/ml |
| H45 | Strain H45 | 0.2 U/ml |
| YN2 | Strain YN2 | 0.4 U/ml |
| P161 | Strain P161 | 0.2 U/ml |

Such enzyme was concentrated with an organism solution specimen condenser (trade name: Mizubutorikun; Ato Co.) to obtain the crude enzyme solution of 10 U/mL.

Reference Example 8

Synthesis of 3-hydroxyacyl CoA (R)-3-hydroxyoctanoyl-CoA was synthesized according to Rehm B H A, Kruger N, Steinbuchel A (1998) Journal of Biological Chemistry 273 pp 24044-24051 with certain changes. Acyl-CoA synthetase (Sigma Co.) was dissolved in trishydrochloric acid buffer (50 mM, pH 7.5) containing 2 mM ATP, 5 mM $MgCl_2$, 2 mM coenzyme A and 2 mM (R)-3-hydroxyoctanoate to a concentration of 0.1 mU/μL. It was retained in a bath of 37° C. and was sampled suitably and the proceeding of reaction was analyzed by HPLC. After the enzyme reaction was terminated by adding sulfuric acid to 0.02 N to the sampled reaction liquid, the unreacted substrate (R)-3-hydroxyoctganoate was removed by extraction with n-heptane. The HPLC analysis employed RP18 column (nucleosil C18, 7 μm, Knauser), and elusion was made under a linear concentration slope of acetonitrile, utilizing 25 mM phosphoric acid buffer (pH 5.3) as the moving phase, and the thioester compound generated by the enzymatic reaction was detected by monitoring the absorption spectrum of 200 to 500 nm with a diode array detector. (R)-3-hydroxy-5-phenylvaryl CoA and (R)-3-hydroxy-5-(4-fluorophenyl)valeryl CoA were also synthesized in a similar manner.

Example 1

Pseudomonas cichorii YN2 (FERM BP7375) was inoculated in 20 L of M9 culture medium containing D-glucose 0.5% and 5-(4-fluorophenyl)valeric acid (FPVA) 0.1% and was cultured under agitation at 30° C., 80 revolutions/min. with an aeration of 2.5 L/min. After 48 hours, the cells were collected by centrifuging, then re-suspended in 20 L of M9 medium containing D-glucose 0.5% and FPVA 0.1% but not containing nitrogen source ($NH_4Cl$) and cultured under agitation at 30° C., 80 revolutions/min. with an aeration of 2.5 L/min. After 48 hours, the cells were collected by centrifuging, and 1 g was separated for evaluation from the wet cells, then washed once with cold methanol and lyophilized to obtain a lyophilized pellet.

The remaining wet cells were suspended in 500 mL of about 1.7% aqueous solution of sodium hypochlorite and PHA was extracted by shaking for 2 hours at about 4° C. PHA recovery by centrifugation and drying provided 0.87 g of PHA per 1 L of culture. This PHA is called Example Compound 1.

The lyophilized pellet was suspended in 20 mL of chloroform, agitated for 20 hours at 60° C. to extract PHA. The extract was filtered with a membrane filter of a pore size of 0.45 μm, concentrated in a rotary evaporator, then the concentrate was reprecipitated in cold methanol and the precipitate alone was recovered and dried under vacuum to obtain PHA.

The composition of obtained PHA was analyzed in the following manner. About 10 mg of PHA, charged in a 25 mL eggplant flask, was dissolved in 2 mL of chloroform, then added with 2 ml of methanol solution containing 3% sulfuric acid and was reacted for 3.5 hours under reflux at 100° C. After the reaction, 10 ml of deionized water was added, and, after vigorous shaking for 10 minutes, the lower chloroform layer was taken out, then dehydrated with magnesium sulfate and was measured by a gas chromatograph—mass-spectrometer (GC-MS, Shimadzu QP-5050, column: DB-WAX (J & W, 0.32 mm×30 m), EI method) to identify the methyl-esterified substance of the PHA monomer unit. As a result, 96% of the PHA monomer units were 3HFPV and 4% were 3-hydroxyvaleric acid. Thus there could be obtained PHA with a high ratio of the desired 3HFPV monomer unit derived from FPVA.

Further, the molecular weight of PHB was evaluated by gel permeation chromatography (GPC: Toso HLC-8020, column: Polymer Laboratory PLgel MIXED-C (5 μm), solvent: chloroform, converted as polystyrene) to obtain a result $Mn=71,5000$ and $Mw=158,000$.

Example 2

The process of Example 1 was reproduced under the identical conditions except that FPVA was replaced by 3-hydroxy-4-phenoxy butyric acid (PxBA) to obtain PHA containing 3-hydroxy-4-phenoxy butyric acid monomer unit (3HPxB) in an amount of 0.15 g per 1 L of the culture liquid. This PHA is called Example Compound 2.

In an evaluation on the obtained PHA similar to that in Example 1, the PHA monomer units were comprised of PxBA by 95% and 3-hydroxybutyric acid unit by 5%. In this manner there was obtained, with a high yield, PHA having a high ratio of the desired 3HPxB monomer unit derived from PxBA. The molecular weight was $Mn=71,500$ and $Mw=158,000$.

Example 3

The process of Example 1 was reproduced under the identical conditions except that FPVA was replaced by 4-cyclohexyl butyric acid (CHBA) to obtain PHA containing 3-hydroxy-4-cyclohexyl butyric acid monomer unit (3HCHB) in an amount of 0.79 g per 1 L of the culture liquid. This PHA is called Example Compound 3.

In an evaluation on the obtained PHA similar to that in Example 1, the PHA monomer units were comprised of 3HCHB by 98% and 3-hydroxybutyric acid unit by 2%. In this manner there was obtained, with a high yield, PHA having a high ratio of the desired 3HCHB monomer unit derived from CHBA. The molecular weight was Mn=92,000 and Mw=218,000.

Example 4

The process of Example 1 was reproduced under the identical conditions except that FPVA was replaced by 5-benzoyl valeric acid (BzVA) to obtain PHA containing 3-hydroxy-5-benzoyl valeric acid monomer unit (3HBzV) in an amount of 0.55 g per 1 L of the culture liquid. This PHA is called Example Compound 4.

In an evaluation on the obtained PHA similar to that in Example 1, 88% of the PHA monomer units were 3HBzV, and 12% were at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid. In this manner there was obtained, with a high yield, PHA having a high ratio of the desired 3HBzV monomer unit derived from BzVA. The molecular weight was Mn=325,000 and Mw=1,240,000.

Example 5

The process of Example 1 was reproduced under the identical conditions except that FPVA was replaced by 5-(4-fluorobenzoyl) valeric acid (FBzVA) to obtain PHA containing 3-hydroxy-5-(4-fluorobenzoyl) valeric acid monomer unit (3HFBzV) in an amount of 0.35 g per 1 L of the culture liquid. This PHA is called Example Compound 5.

In an evaluation on the obtained PHA similar to that in Example 1, the PHA monomer units were comprised of 3HFBzV by 79%, and at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid by 21%. In this manner there was obtained, with a high yield, PHA having a high ratio of the desired 3HFBzV monomer unit derived from FBzVA. The molecular weight was Mn=285,000 and Mw=833,000.

Example 6

The process of Example 1 was reproduced under the identical conditions except that FPVA was replaced by 5-thienyl valeric acid (TVA) to obtain PHA containing 3-hydroxy-5-thienyl valeric acid monomer unit (3HTV) in an amount of 0.85 g per 1 L of the culture liquid. This PHA is called Example Compound 6.

In an evaluation on the obtained PHA similar to that in Example 1, the PHA monomer units were comprised of 3HTV by 97%, and 3-hydroxybutyric acid unit by 3%. In this manner there was obtained, with a high yield, PHA having a high ratio of the desired 3HTV monomer unit derived from TVA. The molecular weight was Mn=75,000 and Mw=185,000.

Example 7

The process of Example 1 was reproduced under the identical conditions except that FPVA was replaced by 5-thienoyl valeric acid (ToVA) to obtain PHA containing 3-hydroxy-5-thienoyl valeric acid monomer unit (3HToV) in an amount of 0.15 g per 1 L of the culture liquid. This PHA is called Example Compound 7.

In an evaluation on the obtained PHA similar to that in Example 1, the PHA monomer units were comprised of 3HToV by 62%, and at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid by 38%. In this manner there was obtained, with a high yield, PHA having a high ratio of the desired 3HToV monomer unit derived from ToVA. The molecular weight was Mn=105,000 and Mw=252,000.

Example 8

The process of Example 1 was reproduced under the identical conditions except that FPVA was replaced by 5-(4-fluorothiophenoxy) valeric acid (FTPxVA) to obtain PHA containing 3-hydroxy-5-(4-fluorothiophenoxy) valeric acid monomer unit (3HFTPxV) in an amount of 0.92 g per 1 L of the culture liquid. This PHA is called Example Compound 8.

In an evaluation on the obtained PHA similar to that in Example 1, the PHA monomer units were comprised of 3HFTPxV by 82%, and at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid by 18%. In this manner there was obtained, with a high yield, PHA having a high ratio of the desired 3HFTPxV monomer unit derived from FTPxVA. The molecular weight was Mn=95,000 and Mw=282,000.

Example 9

The process of Example 1 was reproduced under the identical conditions except that FPVA was replaced by 5-[(4-fluorophenylmethyl)sulfanyl] valeric acid to obtain PHA containing 3-hydroxy-5-[(4-sluorophenylmethyl)sulfanyl] valeric acid monomer unit in an amount of 0.35 g per 1 L of the culture liquid. This PHA is called Example Compound 9.

In an evaluation on the obtained PHA similar to that in Example 1, the PHA monomer units were comprised of 3-hydroxy[(4-fluorophenylmethyl)sulfanyl] valeric acid by 89%, and at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid by 11%. In this manner there was obtained, with a high yield, PHA having a high ratio of the desired 3-hydroxy-5-[(4-fluorophenylmethyl)sulfanyl] valeric acid monomer unit derived from 5-[(4-fluorophenylmethyl)sulfanyl] valeric acid. The molecular weight was Mn=35,000 and Mw=92,000.

Example 10

The process of Example 1 was reproduced under the identical conditions except that FPVA was replaced by 5-thiothienoxy valeric acid (TTxVA) to obtain PHA containing 3-hydroxy-5-thiothienoxy valeric acid monomer unit (3HTTxV) in an amount of 1.1 g per 1 L of the culture liquid. This PHA is called Example Compound 10.

In an evaluation on the obtained PHA similar to that in Example 1, the PHA monomer units were comprised of 3HTTxV by 90%, and at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid by 10%. In this manner there was obtained, with a high yield, PHA having a high ratio of the desired 3HTTxV monomer unit derived from TTxVA. The molecular weight was Mn=205,000 and Mw=550,000.

Example 11

The process of Example 1 was reproduced under the identical conditions except that FPVA was replaced by octanoic acid (OA) to obtain PHA containing 3-hydroxy-octanoic acid monomer unit (3HO) in an amount of 0.75 g per 1 L of the culture liquid. This PHA is called Example Compound 4.

In an evaluation on the obtained PHA similar to that in Example 1, the PHA monomer units were comprised of 3HO by 65%, and at least one of 3-hydroxybutyric acid unit, 3-hydroxyhexanoic acid, 3-hydroxyoctanoic acid, 3-hydroxydecanoic acid, 3-hydroxydodecanoic acid and 3-hydroxydedecenoic acid by 35%. In this manner there was obtained, with a high yield, PHA having a high ratio of the desired 3HO monomer unit derived from OA. The molecular weight was Mn=132,000 and Mw=312,000.

Example 12

A colony of stain YN2 grown on an M9 agar medium containing yeast extract 0.1% was suspended in a sterilized physiological salt solution to OD (600 nm) 1.0. The obtained suspension was spread on 100 plates of 1/10N M9 agar medium not containing any carbon source prepared in advance, and incubated at 30° C. in an atmosphere of 1-octene.

The cells were collected after 4 days, washed with methanol, recovered by centrifugation and dried under a reduced pressure. The dried cells were added to 50 mL of chloroform, and were agitated for 48 hours at 30° C. to extract PHA. The chloroform layer was filtered, then concentrated in an evaporator and poured into cold methanol. Precipitate was recovered and dried under a reduced pressure to obtain 0.26 g of PHA.

The obtained PHA was evaluated as in the Example 1 and was subjected to $^1$H-NMR analysis (equipment: FT-NMR (Bruker DPX400); measured nuclide: 1H; solvent: CDCl$_3$ including TMS). The protons involved in methyne at the end of the side chain, a double bond at the end of the side chain and an epoxy group were attributed according to Macromolecules, 31, 1480-1486(1998). As a result, the PHA monomer units were comprised of epoxy units by 17%, saturated units by 30% and unsaturated units by 53%. The saturated and unsaturated units were at least one of 3-hydroxyhexanoic acid, 3-hydroxyheptanic acid, 3-hydroxyoctanoic acid, 3-hydroxydecanoic acid, 3-hydroxydodecanoic acid, 3-hydroxyhexenoic acid, 3-hydroxyheptenoic acid, 3-hydroxyoctenoic acid and 3-hydroxydedecenoic acid. In this manner there was obtained, with a high yield, PHA having a high ratio of the desired epoxy monomer unit derived from 1-octene. The molecular weight was Mn=251,000 and Mw=550,000.

Example 13

500 mg of acetic acid salt (manufactured by TAP) of N—(S)-2-tetrahydrofuroyl-Gly-D2Nal-D4ClPhe-D3Pal-Ser-NmeTyr-Dlys(Nic)-Leu-Lys(Nisp)-Pro-DalaNH2 (hereinafter called peptide A) was dissolved in 0.6 ml of distilled water. The obtained solution was added to a solution formed by dissolving 4.5 g of Example Compound 1 in 5.8 ml of dichloromethane, and was mixed by a small homogenizer (Kinematica) for 60 seconds to obtain a w/o emulsion. The w/o emulsion was cooled to 16° C. and added to 1000 ml of 0.1% aqueous solution of polyvinyl alcohol (EG-40, Nippon Synthetic Chemicals Co.) cooled to 16° C. in advance, and was formed into w/o/w emulsion by a turbine-type homomixer (Tokushu Kika Co.) at 7000 rpm. The w/o/w emulsion was agitated for 3 hours at room temperature to evaporate dichloromethane thereby solidifying the w/o emulsion, and centrifuged at 2000 rpm by an centrifuge (05PR, Hitachi Mfg. Co.). The obtained precipitate was re-dispersed in distilled water and the dispersion was further centrifuged to remove free drug. The obtained microcapsules were re-dispersed in a small amount of distilled water, added with 0.3 g D-mannitol and lyophilized to obtain microcapsules 1 in powder form. The content of the peptide A in the microcapsules 1 is shown in Tab. 3.

Examples 14 to 24

The process of the Example 13 was reproduced under the identical conditions except that Example Compound 1 was replaced by Example Compounds 2~12 to obtain microcapsules 2~12. The contents of the peptide A in such microcapsules are shown in Tab. 3.

Example 25

50 parts of the above-mentioned microcapsules 12 were suspended in 50 parts of purified water, and 0.5 parts of hexamethylene diamine were dissolved as a crosslinking agent in the suspension. After dissolution was confirmed, water was eliminated by lyophilization, and the mixture was reacted for 12 hours at 70° C. to obtain microcapsules 13. The content of peptide A in the microcapsules is shown in Tab. 3.

Further, the infrared absorption was measured with the microcapsules 13 (FT-IR; Perkin Elmer, 1720X). As a result, peaks of amine (at about 3340 cm$^{-1}$) and epoxy (at about 822 cm$^{-1}$), observed prior to heating, disappeared in the microcapsules 13. This indicates that the microcapsules 13 covered with the crosslinked polymer were obtained by the reaction between PHA having an epoxy unit in the side chain and hexamethylene diamine.

Example 26

50 parts of the aforementioned microcapsule 12 were added to 10 parts of end-amino-group modified polysiloxane (modified silicone oil TSF4700, GE-Toshiba Silicone Co.) and reacted for 2 hours at 70° C. The reaction product was then washed and dried by repeated suspension in methanol and centrifugation (10,000×g, 4° C., 20 min.) to obtain microcapsules 14 having a polysiloxane graft chain. The content of peptide A in the microcapsules 14 is shown in Tab. 3.

The infrared absorption measured on the microcapsules 14 (FT-IR; Perkin Elmer, 1720X) indicated that peaks of amine (about 3340 cm$^{-1}$) and epoxy (about 822 cm$^{-1}$) observed before heating, disappeared in the microcapsules 14. This result indicates that the microcapsules 14 having a polysiloxane graft chain were obtained by the reaction between PHA having an epoxy unit in the side chain and end-amino group modified polysiloxane.

Comparative Example 1

The process of the Example 13 was reproduced under the identical conditions except that Example Compound was replaced by a lactic acid-glycolic acid copolymer (PLGA) (Wako Pure Chemicals Co., lot. No. 940810, lactic acid/glycolic acid (molar ratio): 74/26, GPC weight-averaged molecular weight: 10,000, GPC number-averaged molecular weight: 3,900, number-averaged molecular weight by terminal group quantitative analysis: 3,700) to obtain microcapsules 15. The drug content therein is shown in Tab. 3.

TABLE 3

| Example | Capsule No. | Ex. Compound | Drug content (%) |
|---|---|---|---|
| 13 | 1 | 1 | 16.5 |
| 14 | 2 | 2 | 17.1 |
| 15 | 3 | 3 | 17.8 |
| 16 | 4 | 4 | 18.0 |
| 17 | 5 | 5 | 18.7 |
| 18 | 6 | 6 | 16.4 |
| 19 | 7 | 7 | 17.6 |
| 20 | 8 | 8 | 18.1 |
| 21 | 9 | 9 | 17.3 |
| 22 | 10 | 10 | 18.7 |
| 23 | 11 | 11 | 17.0 |
| 24 | 12 | 12 | 17.6 |
| 25 | 13 | 12 + crosslink | 17.1 |
| 26 | 14 | 12 + grafting | 16.7 |
| Comp. Ex. 1 | 15 | PLGA | 14.0 |

Example 27

500 mg of acetic acid salt of peptide A (TAP) was dissolved in 0.6 ml of 0.1 M phosphate buffer (pH 7.0), and 60 μl of purified enzyme liquid (1), 60 mg of (R)-3-hydroxybutyryl CoA (Sigma Aldrich Japan Co.) and 5 mg of bovine serum albumin were added and dissolved therein. The obtained solution was added to 5.8 ml of dichloromethane, and was mixed by a small homogenizer (Kinematica) for 60 seconds to obtain a w/o emulsion. The w/o emulsion was cooled to 16° C. and added to 1000 ml of 0.1% aqueous solution of polyvinyl alcohol (EG-40, Nippon Synthetic Chemicals Co.) cooled to 16° C. in advance, and was formed into w/o/w emulsion by a turbine-type homomixer (Tokushu Kika Co.) at 7000 rpm. The w/o/w emulsion was agitated for 3 hours at room temperature to carry out PHA synthesis while dichloromethane was evaporated, and the solidified w/o emulsion was centrifuged at 2000 rpm by an centrifuge (05PR, Hitachi Mfg. Co.). The obtained precipitate was re-dispersed in distilled water and the dispersion was further centrifuged to remove the free drug. The obtained microcapsules were re-dispersed in a small amount of distilled water, added with 0.3 g D-mannitol and lyophilized to obtain microcapsules 16 in powder form. The content of the peptide A in the microcapsules 1 is shown in Tab. 4.

The capsules 16 were suspended in 20 mL of chloroform and agitated for 20 hours at 60° C. to extract PHB constituting the outer covering (shell). The extract was filtered with a membrane filter of a pore size of 0.45 μm, then concentrated under a reduced pressure by a rotary evaporator, then subjected to methanolysis by a conventional method and analyzed by gas chromatography-mass spectrometry (GC-MS, Shimadzu QP-5050, EI method) to identify the methylester compound of the PHB monomer units. The main component of the outer covering of the obtained capsules 16 was confirmed as PHB, since the peak of the main component in the obtained chromatogram had the same retension time as that of the methylated compound of standard hydroxybutyric acid.

Also the molecular weight of PHB was measured by gel permeation chromatography (GPC: TosoHLC-8020, column: Polymer Laboratory Plgel MIXED-C (5 μm), solvent: chloroform, column temperature: 40° C., converted into polystyrene) and was identified as Mn=73,000.

Example 28

The process of Example 27 was reproduced under the identical conditions except that the purified enzyme liquid (1) was replaced by crude enzyme liquid (1) to obtain capsules 17. The drug content in the microcapsules is shown in Tab. 4.

Evaluation as in Example 27 confirmed that the principal component of the outer covering of the obtained microcapsules 17 was PHB. Also based on the analysis by gel permeation chromatography, the number-averaged molecular weight of PHA contained in the obtained microcapsules 17 was 71,000.

Example 29

The process of Example 27 was reproduced under the identical conditions except that the purified enzyme liquid (1) was replaced by crude enzyme liquid (2) to obtain capsules 18. The drug content in the microcapsules is shown in Tab. 4.

Evaluation as in Example 27 confirmed that the principal component of the outer covering of the obtained microcapsules 18 was PHB. Also based on the analysis by gel permeation chromatography, the number-averaged molecular weight of PHA contained in the obtained microcapsules 18 was 73,000.

Example 30

The process of Example 27 was reproduced under the identical conditions except that the purified enzyme liquid (1) was replaced by purified enzyme liquid (2) and that (R)-3-hydroxybutyryl CoA was replaced by (R)-3-hydroxyoctanoyl CoA prepared according to a method described in Eur. J. Biochem., 250, 432-439(1997)) to obtain capsules 19. The drug content in the microcapsules is shown in Tab. 4.

Evaluation as in Example 27 confirmed that the principal component of the outer covering of the obtained microcapsules 19 was PHA comprised of 3-hydroxyoctanoic acid unit. Also based on the analysis by gel permeation chromatography, the number-averaged molecular weight of PHA contained in the obtained microcapsules 19 was 24,000.

Example 31

The process of Example 27 was reproduced under the identical conditions except that the purified enzyme liquid (1) was replaced by purified enzyme liquid (3) and that (R)-3-hydroxybutyryl CoA was replaced by (R,S)-3-hydroxy-5-phenylvaleryl CoA prepared according to a method described in Eur. J. Biochem., 250, 432-439(1997)) with hydrolyzed 3-hydroxy-5-phenylvalerate ester obtained by Reformatsky reaction, and then to obtain capsules 20. The drug content in the microcapsules is shown in Tab. 4.

Evaluation as in Example 27 confirmed that the principal component of the outer covering of the obtained microcapsules 20 was PHA comprised of 3-hydroxy-5-phenylvaleryl acid unit. Also based on the analysis by gel permeation chromatography, the number-averaged molecular weight of PHA contained in the obtained microcapsules 20 was 21,000.

Example 32

To obtain capsules 21, the process of Example 27 was reproduced under the identical conditions except that the purified enzyme liquid (1) was replaced by crude enzyme liquid (3) and that (R)-3-hydroxybutyryl CoA was replaced by (R,S)-3-hydroxy-5-phenoxyvaleryl CoA. prepared according to a method described in Eur. J. Biochem., 250, 432-439(1997) using 3-hydroxy-5-phenylvaleric acid. 3-hydroxy-5-phenylvaleric acid was prepared by hydrolyzing 3-hydroxy-5-phenylvalerate ester synthesized from ethyl bromoacetate and 3-phenoxypropanal (synthesized according to J. Org. Chem., 55, 1490-1492(1990)) by the zinc-based Reformatsky reaction. The drug content in the microcapsules is shown in Tab. 4.

Evaluation as in Example 27 confirmed that the principal component of the outer covering of the obtained microcapsules 21 was PHA comprised of 3-hydroxy-5-phenoxyvaleric acid unit. Also based on the analysis by gel permeation chromatography, the number-averaged molecular weight of PHA contained in the obtained microcapsules 21 was 24,000.

Example 33

The process of Example 27 was reproduced under the identical conditions except that the purified enzyme liquid (1) was replaced by crude enzyme liquid (4) and that (R)-3-hydroxybutyryl CoA was replaced by (R,S)-3-hydroxy-5-phenylvaleryl CoA to start PHA synthesizing reaction. The reaction was conducted for 1 hour at room temperature, and, after addition of 60 mg of (R,S)-3-hydroxy-5-phenoxyvaleryl CoA, was further conducted for 2 hours at room temperature. The process thereafter was conducted in the identical manner as in Example 27 to obtain capsules 22. The drug content in the microcapsules is shown in Tab. 4.

The mass of the polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-5-phenoxyvaleryl acid unit. Also in the measurement of similar TOF-SIMS mass spectrum gradually scraping the surface of the capsule construct by ion sputtering confirmed that the principal component of PHA constituting the capsule construct changed to 3-hydroxy-5-phenylvaleric acid unit at a certain time. These results confirmed that the capsule construct of the present example had a desired structure in which the drug 1 was covered by poly(3-hydroxy-5-phenylvaleric acid) and was further covered thereon by poly(3-hydroxy-5-phenoxyvaleric acid). Also based on the analysis by gel permeation chromatography, the number-averaged molecular weight of PHA contained in the obtained microcapsules 20 was 21,000.

Example 34

The process of Example 27 was reproduced under the identical conditions except that the purified enzyme liquid (1) was replaced by crude enzyme liquid (5) and that 60 mg of (R)-3-hydroxybutyryl CoA was replaced by 48 mg of (R,S)-3-hydroxy-5-phenylvaleryl CoA and 12 mg of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)) to obtain capsules 23. The drug content in the microcapsules is shown in Tab. 4.

The result of $^1$H-NMR analysis (equipment: FT-NMR (Bruker DPX400); measured nuclide: 1H; solvent: $CDCl_3$ including TMS) indicated that the outer covering of the obtained capsules 23 was PHA comprised of 3-hydroxy-5-phenylvaleric acid unit by 77%, and 3-hydroxy-7,8-epoxyoctanoic acid unit by 23%. Also based on the analysis by gel permeation chromatography, the number-averaged molecular weight of PHA contained in the obtained microcapsules 23 was 22,000.

Example 35

50 parts of the above-mentioned microcapsules 23 were suspended in 50 parts of purified water, and 0.5 parts of hexamethylene diamine were dissolved as a crosslinking agent in the suspension. After dissolution was confirmed, water was eliminated by lyophilization, and the mixture was reacted for 12 hours at 70° C. to obtain microcapsules 24. The content of peptide A in the microcapsules is shown in Tab. 4.

Further, the infrared absorption was measured with the microcapsules 24 (FT-IR; Perkin Elmer, 1720X). As a result, peaks of amine (at about 3340 $cm^{-1}$) and epoxy (at about 822 $cm^{-1}$) observed before heating, disappeared in the microcapsules 24. This indicates that the microcapsules 24 covered with the crosslinked polymer were obtained by the reaction of PHA having an epoxy unit in the side chain with hexamethylene diamine.

Example 36

50 parts of the aforementioned microcapsule 24 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain microcapsules 25 having a polysiloxane graft chain. The content of peptide A in the microcapsules 25 is shown in Tab. 4.

The infrared absorption measured on the microcapsules 25 (FT-IR; Perkin Elmer, 1720X) indicated that peaks of amine (about 3340 $cm^{-1}$) and epoxy (about 822 $cm^{-1}$), observed before heating, disappeared in the microcapsules 25. This result indicates that the microcapsules 25 having a polysiloxane graft chain were obtained by the reaction of PHA having an epoxy unit in the side chain with end-amino group modified polysiloxane.

TABLE 4

| Example | Capsule No. | Drug content (%) |
|---------|-------------|------------------|
| 27 | 16 | 16.2 |
| 28 | 17 | 16.5 |
| 29 | 18 | 17.0 |
| 30 | 19 | 17.5 |
| 31 | 20 | 18.1 |
| 32 | 21 | 17.8 |
| 33 | 22 | 18.0 |
| 34 | 23 | 18.1 |
| 35 | 24 | 17.5 |
| 36 | 25 | 17.0 |

Example 37

500 mg of acetic acid salt of peptide A (TAP) was dissolved in 0.6 ml of distilled water. The obtained solution was added to 5.8 ml of dichloromethane, and was mixed by a small homogenizer (Kinematica) for 60 seconds to obtain a w/o emulsion. The w/o emulsion was cooled to 16° C. and added to 100 mL of 0.1 M phosphate buffer (pH 7.0) containing 0.1% polyvinyl alcohol (EG-40, Nippon Synthetic Chemicals Co.) cooled to 16° C. in advance, and a w/o/w emulsion was made by using a turbine-type homomixer (Tokushu Kika Co.) at 7000 rpm. In the w/o/w emulsion, 5 ml of purified enzyme liquid (1), 1 g of (R)-3-hydroxybutyryl CoA (Sigma Aldrich Japan Co.) and 100 mg of bovine serum albumin (Sigma Co.) were added and dissolved therein.

The w/o/w emulsion was agitated for 3 hours at room temperature to carry out PHA synthesis while dichloromethane was evaporated, and the solidified w/o emulsion was centrifuged at 2000 rpm by an centrifuge (05PR-22, Hitachi Mfg. Co.). The obtained precipitate was re-dispersed in distilled water and the dispersion was further centrifuged to remove the free drug. The obtained microcapsules were re-dispersed in a small amount of distilled water, added with 0.3 g of D-mannitol and lyophilized to obtain microcapsules 26 in powder form. The content of the peptide A in the microcapsules 1 is shown in Tab. 5.

The capsules 26 were suspended in 20 mL of chloroform and agitated for 20 hours at 60° C. to extract PHB constituting the outer covering. The extract was filtered with a membrane filter of a pore size of 0.45 µm, then concentrated under a reduced pressure by a rotary evaporator, then subjected to methanolysis by a conventional normal method and analyzed by gas chromatography-mass spectrometry (GC-MS, Shimadzu QP-5050, EI method) to identify the methylester compound of the PHB monomer units. The main component of the outer covering of the obtained capsules 26 was confirmed as PHB, since the peak of the main component in the obtained chromatogram had the same retension time as that of a methylated compound of standard hydroxybutyric acid.

Also the molecular weight of PHB was measured by gel permeation chromatography (GPC: TosoHLC-8020, column: Polymer Laboratory Plgel MIXED-C (5 µm), solvent: chloroform, column temperature: 40° C., converted into polystyrene) and was identified as Mn=78,000.

Example 38

The process of Example 37 was reproduced under the identical conditions except that the purified enzyme liquid (1) was replaced by crude enzyme liquid (1) to obtain capsules 27. The drug content in the microcapsules is shown in Tab. 5.

Evaluation as in Example 37 confirmed that the principal component of the outer covering of the obtained microcapsules 27 was PHB. Also based on the analysis by gel permeation chromatography, the number-averaged molecular weight of PHA contained in the obtained microcapsules 27 was 75,000.

Example 39

The process of Example 37 was reproduced under the identical conditions except that the purified enzyme liquid (1) was replaced by crude enzyme liquid (2) to obtain capsules 28. The drug content in the microcapsules is shown in Tab. 5.

Evaluation as in Example 37 confirmed that the principal component of the outer covering of the obtained microcapsules 28 was PHB. Also based on the analysis by gel permeation chromatography, the number-averaged molecular weight of PHA contained in the obtained microcapsules 28 was 77,000.

Example 40

The process of Example 37 was reproduced under the identical conditions except that the purified enzyme liquid (1) was replaced by purified enzyme liquid (2) and that (R)-3-hydroxybutyryl CoA was replaced by (R)-3-hydroxyoctanoyl CoA (prepared according to a method described in Eur. J. Biochem., 250, 432-439(1997)) to obtain capsules 29. The drug content in the microcapsules is shown in Tab. 5.

Evaluation as in Example 27 confirmed that the principal component of the outer covering of the obtained microcapsules 29 was PHA comprised of 3-hydroxyoctanoic acid unit. Also based on the analysis by gel permeation chromatography, the number-averaged molecular weight of PHA contained in the obtained microcapsules 29 was 27,000.

Example 41

The process of Example 37 was reproduced under the identical conditions except that the purified enzyme liquid (1) was replaced by purified enzyme liquid (3) and that (R)-3-hydroxybutyryl CoA was replaced by (R,S)-3-hydroxy-5-phenylvaleryl CoA (prepared by hydrolyzing 3-hydroxy-5-phenylvalerate ester obtained by a Reformatsky reaction, and then according to a method described in Eur. J. Biochem., 250, 432-439(1997)) to obtain capsules 30. The drug content in the microcapsules is shown in Tab. 5.

Evaluation as in Example 37 confirmed that the principal component of the outer covering of the obtained microcapsules 30 was PHA comprised of 3-hydroxy-5-phenylvaleryl acid unit. Also based on the analysis by gel permeation chromatography, the number-averaged molecular weight of PHA contained in the obtained microcapsules 30 was 22,000.

Example 42

To obtain capsules 31, the process of Example 37 was reproduced under the identical conditions except that the purified enzyme liquid (1) was replaced by crude enzyme liquid (3) and that (R)-3-hydroxybutyryl CoA was replaced by (R,S)-3-hydroxy-5-phenoxyvaleryl CoA (prepared by starting from 3-phenoxypropanal synthesized according to J. Org. Chem., 55, 1490-1492(1990) and ethyl bromoacetate, hydrolyzing 3-hydroxy-5-phenylvalerate ester obtained by a zinc-based Reformatsky reaction, and then according to a method described in Eur. J. Biochem., 250, 432-439(1997)). The drug content in the microcapsules is shown in Tab. 5.

Evaluation as in Example 37 confirmed that the principal component of the outer covering of the obtained microcapsules 31 was PHA comprised of 3-hydroxy-5-phenoxyvaleric acid unit. Also based on the analysis by gel permeation chromatography, the number-averaged molecular weight of PHA contained in the obtained microcapsules 31 was 23,000.

Example 43

The process of Example 37 was reproduced under the identical conditions except that the purified enzyme liquid (1) was replaced by crude enzyme liquid (4) and that (R)-3-hydroxybutyryl CoA was replaced by (R,S)-3-hydroxy-5-phenylvaleryl CoA to start PHA synthesizing reaction. The reaction was conducted for 1 hour at room temperature, and, after addition of 1 g of (R,S)-3-hydroxy-5-phenoxyvaleryl CoA, was further conducted for 2 hours at room temperature. The process thereafter was conducted in the identical manner as in Example 37 to obtain capsules 32. The drug content in the microcapsules is shown in Tab. 5.

The mass of the polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-5-phenoxyvaleryl acid unit. Also the measurement of similar TOF-SIMS mass spectrum gradually scraping the surface of the capsule construct by ion sputtering confirmed that the principal component of PHA constituting the capsule construct changed from 3-hydroxy-5-phenoxylvaleric acid to 3-hydroxy-5-phenylvaleric acid unit at a certain point. These results confirmed that the capsule construct of the present example had a desired structure in which the drug 1 was covered by poly(3-hydroxy-5-phenylvaleric acid) and was further covered thereon by poly(3-hydroxy-5-phenoxyvaleric acid). Also based on the analysis by gel permeation chromatography, the number-averaged molecular weight of PHA contained in the obtained microcapsules 20 was 24,000.

Example 44

The process of Example 37 was reproduced under the identical conditions except that the purified enzyme liquid (1) was replaced by crude enzyme liquid (5) and that 1 g of (R)-3-hydroxybutyryl CoA was replaced by 800 mg of (R,S)-3-hydroxy-5-phenylvaleryl CoA and 200 mg of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)) to obtain capsules 33. The drug content in the microcapsules is shown in Tab. 5.

The result of $^1$H-NMR analysis (equipment: FT-NMR (Bruker DPX400); measured nuclide: 1H; solvent: $CDCl_3$ including TMS) indicated that the outer covering of the obtained capsules 33 was PHA comprised of 3-hydroxy-5-phenylvaleric acid unit by 76%, and 3-hydroxy-7,8-epoxyoctanoic acid unit by 24%. Also based on the analysis by gel permeation chromatography, the number-averaged molecular weight of PHA contained in the obtained microcapsules 33 was 25,000.

Example 45

50 parts of the above-mentioned microcapsules 23 were suspended in 50 parts of purified water, and 0.5 parts of hexamethylene diamine were dissolved as a crosslinking agent in the suspension. After dissolution was confirmed, water was eliminated by lyophilization, and the mixture was reacted for 12 hours at 70° C. to obtain microcapsules 34. The content of peptide A in the microcapsules is shown in Tab. 5.

Further, the infrared absorption was measured with the microcapsules 34 (FT-IR; Perkin Elmer, 1720X). As a result, peaks of amine (at about 3340 $cm^{-1}$) and epoxy (at about 822 $cm^{-1}$) observed before heating, disappeared in the microcapsules 34. This indicates that microcapsules covered with the crosslinked polymer were obtained by reaction of PHA having an epoxy unit in the side chain with hexamethylene diamine.

Example 46

50 parts of the aforementioned microcapsule 24 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain microcapsules 35 having a polysiloxane graft chain. The content of peptide A in the microcapsules 25 is shown in Tab. 5.

The infrared absorption measured on the microcapsules 35 (FT-IR; Perkin Elmer, 1720X) indicated that peaks of amine (about 3340 $cm^{-1}$) and epoxy (about 822 $cm^{-1}$) observed before heating, disappeared in the microcapsules 35. This result indicates that microcapsules having a polysiloxane graft chain were obtained by the reaction of PHA having an epoxy unit in the side chain with end-amino group modified polysiloxane.

TABLE 5

| Example | Capsule No. | Drug content (%) |
|---|---|---|
| 37 | 26 | 17.1 |
| 38 | 27 | 16.9 |
| 39 | 28 | 17.2 |
| 40 | 29 | 17.9 |
| 41 | 30 | 18.5 |
| 42 | 31 | 18.1 |
| 43 | 32 | 18.5 |
| 44 | 33 | 18.9 |
| 45 | 34 | 18.0 |
| 46 | 35 | 17.3 |

Experimental Example 1

About 20 mg of the microcapsules 12 was dispersed in 0.5 ml of a dispersion medium (a solution of 2.5 mg carboxymethyl cellulose, 0.5 mg polysorbate 80 and 25 mg mannitol in distilled water) and was injected subcutaneously with an injection needle 22G to the back of male SD rats of 10 weeks old.

Some rats were killed at predetermined time intervals after administration, and the microcapsules remaining in the administered position were taken out to determine the amount of peptide A therein. The result is shown in Tab. 6.

Experimental Examples 2 to 9 and Comparative Experimental Example 1

Experimental Example 1 was reproduced under the identical conditions except that the microcapsules 13, 14, 15, 23, 24, 25, 33, 34 and 35 were respectively employed to obtain preparations and to analyze peptide A content with time course. The residual rate is shown in Tab. 6.

TABLE 6

| Experiment. | | Residual rate with time (weeks) after administration | | | |
|---|---|---|---|---|---|
| example | Microcapsule | 1 | 2 | 3 | 4 |
| 1 | 12 | 85.0 | 66.1 | 45.4 | 30.1 |
| 2 | 13 | 90.5 | 72.3 | 53.1 | 37.9 |
| 3 | 14 | 86.1 | 67.3 | 48.3 | 34.0 |
| 4 | 23 | 83.4 | 63.9 | 42.7 | 32.0 |
| 5 | 24 | 92.1 | 73.4 | 49.9 | 39.2 |
| 6 | 25 | 87.3 | 64.2 | 45.3 | 33.3 |
| 7 | 33 | 83.9 | 64.1 | 44.1 | 32.5 |
| 8 | 34 | 91.0 | 72.1 | 51.2 | 40.0 |
| 9 | 35 | 86.1 | 65.0 | 45.9 | 34.8 |
| Comp. Ex. Example 1 | 15 | 83.2 | 55.1 | 36.2 | 20.0 |

Example 47

500 mg of Example Compound 1 was dissolved in 70 mL of chloroform. Then 10 mL of water-soluble dye Direct special black AXN (Nippon Kayaku Co.) solution was added, and emulsification was executed with a probe ultrasonic oscillator (Ohtake) to obtain a w/o emulsion. The ultrasonic irradiation was executed with a power of 50 W for 30 seconds and repeated 10 times. The emulsion thus prepared was processed in a rotary evaporator to distill off the organic solvent under a reduced pressure at 60° C. thereby microcapsules holding the dye. The vacuum in the evaporator was maintained high at the beginning, and gradually lowered with the progress of the evaporation of organic solvent, in order to avoid abrupt boiling. Thereafter, the organic solvent still remaining in the microcapsules in a small amount was eliminated by flashing nitrogen gas. To thus obtained dye-holding microcapsules, 10 mM phosphate buffer (pH 7.0) was added to 30 mL, then filtered through a 1.2μ filter (Acrodisc, Gelman) and dialyzed for 24 hours to 10 mM phosophate buffer using a dyalysis membrane (Spectrapor, Spectrum Medical) to eliminate free dye. Thus-obtained dye-holding microcapsules 36 was used for Ink 1. The average particle size measured by dynamic optical scattering and the results of observation under an optical microscope and an electron microscope are shown in Tab. 7.

Examples 48 to 58

Example 47 was reproduced under the identical conditions, except that Example Compounds 2 to 12 were employed as the polymer, to obtain microcapsules 37 to 47 as inks 2 to 12.

The average particle size measured by dynamic optical scattering and the results of observation under an optical microscope and an electron microscope are shown in Tab. 7.

Example 59

50 parts of the above-mentioned microcapsules 23 were suspended in 50 parts of purified water, to which 0.5 parts of hexamethylene diamine was dissolved as a crosslinking agent. After confirmation of dissolution, water was eliminated by lyophilization, and the mixture was reacted for 12 hours at 70° C. to obtain microcapsules 48. The average particle size measured by dynamic optical scattering and the results of observation under an optical microscope and an electron microscope are shown in Tab. 7.

Further, the infrared absorption was measured with the microcapsules 48 (FT-IR; Perkin Elmer, 1720X). As a result, peaks of amine (at about 3340 $cm^{-1}$) and epoxy (at about 822 $cm^{-1}$), observed before heating, disappeared in the microcapsules 48. This indicates that the microcapsules 48 covered with the crosslinked polymer were obtained by reaction of PHA having an epoxy unit in the side chain with hexamethylene diamine.

Example 60

50 parts of the aforementioned microcapsule 47 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain microcapsules 49 having a polysiloxane graft chain, and constituting ink 14. The average particle size measured by dynamic optical scattering and the results of observation under an optical microscope and an electron microscope are shown in Tab. 7.

The infrared absorption measured on the microcapsules 49 (FT-IR; Perkin Elmer, 1720X) indicated that peaks of amine (about 3340 $cm^{-1}$) and epoxy (about 822 $cm^{-1}$), observed before heating, disappeared in the microcapsules 49. This result indicates that microcapsules having a polysiloxane graft chain were obtained by the reaction of PHA having an epoxy unit in the side chain with end-amino group modified polysiloxane.

Comparative Example 2

Example 47 was reproduced under the identical conditions, except that poly DL lactic acid (average molecular weight 7000) was employed as the polymer, to obtain microcapsules 50 as ink 15.

The average particle size measured by dynamic optical scattering and the results of observation under an optical microscope and an electron microscope are shown in Tab. 7.

TABLE 7

| Example | Capsule No. | Ex. compound | Average part. size | Pore |
|---|---|---|---|---|
| 47 | 36 | 1 | 750 | none |
| 48 | 37 | 2 | 720 | none |
| 49 | 38 | 3 | 840 | none |
| 50 | 39 | 4 | 770 | none |
| 51 | 40 | 5 | 850 | none |
| 52 | 41 | 6 | 830 | none |
| 53 | 42 | 7 | 850 | none |
| 54 | 43 | 8 | 840 | none |
| 55 | 44 | 9 | 820 | none |
| 56 | 45 | 10 | 790 | none |
| 57 | 46 | 11 | 830 | none |
| 58 | 47 | 12 | 820 | none |
| 59 | 48 | 12 + crosslinking | 840 | none |
| 60 | 49 | 12 + grafting | 870 | none |
| Comp. Ex. 2 | 50 | PLGA | 980 | present |

Example 61

To 70 mL of chloroform, added was a 10 mL solution of water-soluble dye, Direct special black AXN (Nippon Kayaku Co.) containing 10 U/mL of PHA synthetase YN2-C1 prepared in Reference Example 6 from *Pseudomonas cichorii* YN2 strain and 1 mM (R)-3-hydroxyoctanoyl CoA prepared in Reference Example 8, and the mixture was emulsified with a probe ultrasonic oscillator (Ohtake) to obtain a w/o emulsion. Ultrasonic irradiation was executed with a power of 50 W for 30 seconds and repeated 10 times. The emulsion thus prepared was incubated at 37° C. for 3 hours for PHA synthesis.

The reaction liquid was size separated by gel filtration (Sephadex G-50 column) to obtain microcapsules. Based on the dynamic light scattering method, the microcapsules had an average particle size of 820 nm and was in a mono-dispersed state.

A part of the prepared microcapsules was dried in vacuum, then suspended in 20 ml of chloroform and agitated for 20 hours at 60° C. to extract PHA constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was made from 3-hydroxyoctanoic acid monomer unit. Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=13,000 and Mw=32,000.

Example 62

Microcapsules holding an antibiotic, vancomycin, were prepared in the following manner. To 70 mL of chloroform, added was 10 mL of 5% glucose solution in which added were vancomycin in an amount of 0.2 g, the PHA synthetase YN2-C1 prepared in Reference Example 6 from *Pseudomonas cichorii* YN2 strain with a concentration of 10 U/mL and (R)-3-hydroxyoctanoyl CoA prepared in Reference Example 8 so as to have an end concentration of 1 mM, and the mixture was emulsified with a probe ultrasonic oscillator (Ohtake) to obtain a w/o emulsion. Ultrasonic irradiation was executed with a power of 50 W for 30 seconds and repeated 10 times. The emulsion thus prepared was incubated for PHA synthesis at 37° C. for 3 hours.

The reaction liquid was size separated by gel filtration (Sephadex G-50 column) to obtain microcapsules. Based on the dynamic light scattering method, the microcapsules had an average particle size of 840 nm and was in a mono-dispersed state.

A part of the prepared microcapsules was dried in vacuum, then suspended in 20 ml of chloroform and agitated for 20 hours at 60° C. to extract PHA constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was comprised of 3-hydroxy-5-valeric acid monomer unit. Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=15,000 and Mw=37,000.

Example 63

Microcapsules holding dimethyl(3-methyl-4-nitrophenyl) phosphorothioate as an agriculturally effective compound were prepared in the following manner.

To 70 mL of chloroform, added was 10 mL of a 5% solution of dimethyl(3-methyl-4-nitrophenyl)phosphorothioate containing 10 U/mL of PHA synthetase prepared in Reference Example 7 from strain P161 and 1 mM (R)-3-hydroxy-5-(4-fluorophenyl) valeryl CoA prepared in Reference Example 8, and the mixture was emulsified with a probe ultrasonic oscillator (Ohtake) to obtain a w/o emulsion. Ultrasonic irradiation was executed with a power of 50 W for 30 seconds and repeated 10 times. The emulsion thus prepared was incubated for PHA synthesis for 3 hours at 37° C.

The reaction liquid was size separated by gel filtration (Sephadex G-50 column) to obtain microcapsules. Based on the dynamic light scattering method, the microcapsules had an average particle size of 770 nm and was in a mono-dispersed state.

A part of the prepared microcapsules was dried in vacuum, then suspended in 20 ml of chloroform and agitated for 20 hours at 60° C. to extract PHA constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was comprised of (R)-3-hydroxy-5-(4-fluorophenyl) valeric acid monomer unit. Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=13,000 and Mw=30,000.

Example 64

Microcapsules for consmetic use holding 2,4-dihydroxy-benzophenone being an ultraviolet absorver were prepared in the following manner.

To 70 mL of chloroform, added was 10 mL of a 5% solution of 2,4-dihyroxybenzophenone containing 10 U/mL of PHA synthetase prepared in Reference Example 7 from strain H45 and 1 mM (R)-3-hydroxyoctanoyl CoA prepared in Reference Example 8, and the mixture was emulsified with a probe ultrasonic oscillator (Ohtake) to obtain a w/o emulsion. Ultrasonic irradiation was executed with a power of 50 W for 30 seconds and repeated 10 times. The emulsion thus prepared was incubated for PHA synthesis for 3 hours at 37° C.

The reaction liquid was size separated by gel filtration (Sephadex G-50 column) to obtain microcapsules. Based on the dynamic light scattering method, the microcapsules had an average particle size of 750 nm and was in a mono-dispersed state.

A part of the prepared microcapsules was dried in vacuum, then suspended in 20 ml of chloroform and agitated for 20 hours at 60° C. to extract PHA constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was comprised of 3-hydroxy-octanoic acid monomer unit. Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=16,000 and Mw=34,000.

Example 65

To 70 mL of chloroform, added was 10 mL of aqueous solution of water soluble fluorescent dye calsein in which added were the PHA synthetase prepared in Reference Example 8 from P91 strain with a concentration of 10 U/mL and (R)-3-hydroxyoctanoyl CoA prepared in Reference Example 8 so as to have an end concentration of 1 mM, and the mixture was emulsified with a probe ultrasonic oscillator (Ohtake) to obtain a w/o emulsion. Ultrasonic irradiation was executed with a power of 50 W for 30 seconds and repeated 10 times. The emulsion thus prepared was incubated for PHA synthesis operation by incubation for 3 hours at 37° C.

The reaction liquid was size separated by gel filtration (Sephadex G-50 column) to obtain microcapsules. Based on the dynamic light scattering method, the microcapsules had an average particle size of 840 nm and was in a mono-dispersed state.

A part of the prepared microcapsules was dried in vacuum, then suspended in 20 ml of chloroform and agitated for 20 hours at 60° C. to extract PHA constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHA monomer unit. As a result, it was confirmed that the PHA was comprised of 3-hydroxy-octanoic acid monomer unit. Further, the molecular weight of PHA was evaluated by gel permeation chromatography (GPC: Toso HLC-8020, column: Polymer Laboratory PLgel MIXED-C (5 µm), solvent: chloroform, converted as polystyrene) to obtain a result Mn=18,000 and Mw=40,000.

Example 66

PHA-coated microcapsules holding calsein were prepared in the identical manner as in Example 65. To 2 parts of the microcapsules, there were added 100 parts of 0.1 M phosphate buffer (pH 7.0) containing 100 U/mL of the PHA synthetase YN2-C1 prepared in Reference Example 6 from *Pseudomonas cichorii* YN2, 30 mM of (R)-3-hydroxy-pymeryl CoA (prepared according to J. Bacteriol., 182, 2753-2760(2000)) and 0.1% of bovine serum albumin (Sigma Co.).

After shaking for 3 hours, the reaction product was washed with 0.1 M phosphate buffer (pH 7.0) to eliminate unreacted materials, and was air dried to obtain microcapsules.

After the microcapsules were lyophilized, the mass of the polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-pymeric acid unit. Also in the measurement of similar TOF-SIMS mass spectrum gradually scraping the PHA surface of the liposome by ion sputtering confirmed that the principal component of PHA constituting the capsule construct changed to 3-hydroxy-octanoic acid unit at a certain point. These results confirmed that the microcapsules of the present example had a two-layered structure in which the surface was covered with polyhydroxypymerate having hydrophilic functional groups and a layer thereunder was comprised of polyhydroxyoctanoic acid.

Further, the molecular weight of PHA was evaluated by gel permeation chromatography (GPC: Toso HLC-8020, column: Polymer Laboratory PLgel MIXED-C (5 µm), solvent: chloroform, converted as polystyrene) to obtain a result Mn=19,000 and Mw=42,000.

Example 67

PHA-coated microcapsules holding calsein were prepared in the identical manner as in Example 65. To 1 part of the microcapsules, there were added 49 parts of 0.1 M phosphate buffer (pH 7.0) containing 100 U/mL of the PHA synthetase YN2-C1 prepared in Reference Example 6 from *Pseudomonas cichorii* YN2 strain, 24 mM of (R,S)-3-hydroxy-5-phenoxyvaleryl CoA (prepared by hydrolyszing 3-hydroxy-5-phenoxyvaleryl ester, obtained from 3-phenoxypropanal and ethyl bromoacetate by a Reformatsky reaction to obtain 3-hydroxy-5-phenoxyvaleric acid, and then according to a method described in Eur. J. Biochem., 250, 432-439(1997)) and 6 mM of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)), and 0.1% of bovine serum albumin (Sigma Co.).

After shaking for 3 hours, the reaction product was washed with 0.1 M phosphate buffer (pH 7.0) to eliminate unreacted materials, and was air dried to obtain microcapsules 51.

As a comparative reference, microcapsules 52 were prepared by the same method except that (R,S)-3-hydroxy-7,8-epoxyoctanoyl CoA was replaced by 3-hydroxyoctanoyl CoA.

A 10 µl aliquot of the above reaction solution was put on a slide glass, to which 10 µl of a 1% solution of Nile blue A in water was added. These solutions were mixed on the slide glass, covered with a cover glass, and observed under a fluorescence microscope (330 to 380 nm excitation filter, 420 nm long pass absorption filter, Nikon Corp.). As a result, fluorescence from the surface of the microcapsules was observed to confirm that the microcapsules were coated with PHA on the surface.

Also a part of the sample was collected by centrifugation (10,000×g, 4° C., 10 min.), dried in vacuum, suspended in chloroform and agitated for 20 hours at 60° C. to extract PHA constituting the external shell. The extract was subjected to $^1$H-NMR analysis (equipment: FT-NMR (Bruker DPX400); measured nuclide: 1H; solvent: CDCl$_3$ including TMS). The calculated percentages of the monomer units are shown in Tab. 8.

TABLE 8

| Composition of external shell PHA in the capsule construct (1H-NMR, unit %) | | |
|---|---|---|
| Monomer unit | capsule 51 | capsule 52 |
| 3-hydroxy-5-phenoxy valeric acid | 82% | 71% |
| 3-hydroxy-7,8-epoxyoctanoic acid | 18% | — |
| 3-hydroxyoctanoic acid | — | 29% |

Also 50 parts of the above-mentioned microcapsules 51 were subjected three times to a process of collecting the microcapsules by centrifugation (10,000×g, 4° C., 10 min.) and suspending in 50 parts of purified water. Then 0.5 parts of hexamethylene diamine were dissolved as a crosslinking agent in the suspension. After dissolution was confirmed, water was eliminated by lyophilization (to obtain microcapsules 53). Also the microcapsules 53 were reacted for 12 hours at 70° C. to obtain microcapsules 54.

The above described microcapsules 53 and 54 were suspended in chloroform respectively and stirred for 20 hours at 60° C. to extract PHA coating, then chloroform was removed by vacuum drying. The extracts were analyzed by using a differential scanning calorimeter (DSC; Perkin Elmer, Pyris 1, temperature rise: 10° C./min.). As a result, the microcapsules 53 showed a prominent exothermal peak at about 90° C. indicating that epoxy groups in the polymer were reacting with the hexamethylenediamine and the crosslinking between polymers were proceeding during heating. On the other hand, the microcapsules 54 did not show marked heat flow indicating that the crosslinking reaction had been completed.

Further, the infrared absorption was measured with these samples (FT-IR; Perkin Elmer, 1720X). As a result, peaks indicating amine (at about 3340 cm$^{-1}$) and epoxy (at about 822 cm$^{-1}$) were observed with the microcapsules 53, but not with the microcapsules 54.

These results indicate that a crosslinked polymer can be obtained by the reaction of PHA having an epoxy group in the side chain with hexamethylenediamine.

On the other hand, similar evaluations were executed on the microcapsules 52 as the comparative reference, but there could not be obtained the results clearing indicating the mutual crosslinking of the polymers.

Example 68

A solution of 200 mg of 8-[1-oxo-3-[1-(phenylmethyl)pyperidin-4-yl]propyl]-2,3,4,5-tetrahydro-1H-1-benzazepine (hereinafter called drug 1) and 2.0 g of Example Compound 1 in 2 ml of dichloromethane was cooled to 16 to 18° C. and was poured into 500 ml of a 0.1% aqueous solution of polyvinyl alcohol (EG-40, Nippon Synthetic Chemicals Co.) cooled to 16 to 18° C. in advance, and was formed into an o/w emulsion by a turbine-type homomixer (Tokushu Kika Co.) at 7000 rpm. The o/w emulsion was agitated for 3 hours at room temperature to evaporate dichloromethane thereby solidifying the oil phase, and centrifuged at 1500 rpm. The obtained precipitate was re-dispersed in distilled water and the dispersion was further centrifuged to remove the free drug. The obtained microcapsules were re-dispersed in a small amount of distilled water, and lyophilized to obtain microcapsules 55. The drug content in the microcapsules is shown in Tab. 9. The drug content was determined by HPLC method on 25 mg of microcapsules dissolved in 10 ml of phosphate buffer (pH 7.0) containing 60% acetonitrile.

Examples 69 to 79

Microcapsules 56 to 66 were prepared in the same manner as in Example 68 except for the use of Example Compounds 2 to 12. The drug contents in the microcapsules are shown in Tab. 9.

Example 80

50 parts of the above-mentioned microcapsules 66 were suspended in 50 parts of purified water. Then 0.5 parts of hexamethylene diamine were dissolved as a crosslinking agent in the suspension. After dissolution was confirmed, water was eliminated by lyophilization, and the mixture was reacted for 12 hours at 70° C. to obtain microcapsules 67.

Further, the infrared absorption was measured with the microcapsules 67(FT-IR; Perkin Elmer, 1720X). As a result, peaks of amine (at about 3340 cm$^{-1}$) and epoxy (at about 822 cm$^{-1}$), observed before heating, disappeared in the microcapsules 67. This indicates that the microcapsules 67 covered with the crosslinked polymer were obtained by the reaction of PHA having an epoxy unit in the side chain with hexamethylene diamine.

Example 81

50 parts of the aforementioned microcapsule 66 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain microcapsules 68 having a polysiloxane graft chain.

The infrared absorption measured on the microcapsules 68 (FT-IR; Perkin Elmer, 1720X) indicated that peaks of amine (about 3340 cm$^{-1}$) and epoxy (about 822 cm$^{-1}$), observed before heating, disappeared in the microcapsules 68. This result indicates that microcapsules 68 having a polysiloxane graft chain were obtained by the reaction of PHA having an epoxy unit in the side chain with end-amino group modified polysiloxane.

Comparative Example 3

The process of Example 68 was reproduced under the identical conditions except that Example Compound 1 was replaced by a lactic acid-glycolic acid copolymer (PLGA) (Wako Pure Chemicals Co., lot. No. K1030, lactic acid/glycolic acid (molar ratio): 75/25, GPC weight-averaged molecular weight: 13,000) to obtain microcapsules 69. The drug content therein is shown in Tab. 9.

TABLE 9

| Example | Capsule No. | Example compound | Drug content (%) |
|---|---|---|---|
| 68 | 55 | 1 | 12.3 |
| 69 | 56 | 2 | 11.2 |
| 70 | 57 | 3 | 11.9 |
| 71 | 58 | 4 | 12 |
| 72 | 59 | 5 | 12.5 |
| 73 | 60 | 6 | 10.7 |
| 74 | 61 | 7 | 11.2 |
| 75 | 62 | 8 | 11.8 |
| 76 | 63 | 9 | 11.3 |
| 77 | 64 | 10 | 12.0 |
| 78 | 65 | 11 | 10.8 |
| 79 | 66 | 12 | 11.2 |
| 80 | 67 | 12 + crosslink | 10.9 |
| 81 | 68 | 12 + grafting | 10.7 |
| Ref. Ex. 3 | 69 | PLGA | 9.5 |

Example 82

A solution of 1.5 g of drug 1 and 4.5 g of Example Compound 1 in 9 ml of dichloromethane was cooled to 16 to 18° C. and was poured into 500 ml of a 0.1% aqueous solution of polyvinyl alcohol (EG-40, Nippon Synthetic Chemicals Co.) cooled to 16 to 18° C. in advance, and was formed into an o/w emulsion by a turbine-type homomixer (Tokushu Kika Co.) at 8000 rpm. The o/w emulsion was agitated for 3 hours at room temperature to evaporate dichloromethane thereby solidifying the oil phase, and centrifuged at 1500 rpm. The obtained precipitate was re-dispersed in distilled water and the dispersion was further centrifuged to remove the free drug. The obtained microcapsules were re-dispersed in a small amount of distilled water, and lyophilized to obtain microcapsules 70 in powder form. The drug content in the microcapsules is shown in Tab. 10.

Examples 83 to 93

Microcapsules 71 to 81 were prepared in the same manner as in Example 82 except for the use of Example Compounds 2 to 12. The drug contents in the microcapsules are shown in Tab. 10.

Examples 94

Microcapsules 82 were prepared in the same manner as in Example 80 except for the use of microcapsules 81. The drug content in the microcapsules is shown in Tab. 10.

Examples 95

Microcapsules 83 were prepared in the same manner as in Example 81 except for the use of the microcapsules 81. The drug content in the microcapsules is shown in Tab. 10.

Comparative Example 4

The process of Example 82 was reproduced under the identical conditions except that Example Compound was replaced by a lactic acid-glycolic acid copolymer (PLGA) (Wako Pure Chemicals Co., lot. No. K1030, lactic acid/glycolic acid (molar ratio): 75/25, GPC weight-averaged molecular weight: 13,000) to obtain microcapsules 84. The drug content therein is shown in Tab. 10.

TABLE 10

| Example | Capsul No. | Example compound | Drug content (%) |
|---|---|---|---|
| 82 | 70 | 1 | 21.5 |
| 83 | 71 | 2 | 22.5 |
| 84 | 72 | 3 | 24.2 |
| 85 | 73 | 4 | 24.2 |
| 86 | 74 | 5 | 25.1 |
| 87 | 75 | 6 | 21.8 |
| 88 | 76 | 7 | 23.0 |
| 89 | 77 | 8 | 24.0 |
| 90 | 78 | 9 | 22.8 |
| 91 | 79 | 10 | 23.9 |
| 92 | 80 | 11 | 22.0 |
| 93 | 81 | 12 | 21.5 |
| 94 | 82 | 12 + crosslinking | 21.4 |
| 95 | 83 | 12 + grafting | 21.2 |
| Comp. ex. 4 | 84 | PLGA | 19.5 |

Example 96

A solution of 200 mg of the drug 1 in 2 ml of dichloromethane was cooled to 16 to 18° C. and was poured into 100 ml of 0.1 M phosphate buffer (pH 7.0) containing 0.1% polyvinyl alcohol (EG-40, Nippon Synthetic Chemicals Co.) cooled to 16 to 18° C. in advance, and was formed into an o/w emulsion by a turbine-type homomixer (Tokushu Kika Co.) at 7000 rpm. The o/w emulsion was added with 5 ml of the purified enzyme liquid (1), 1 g of (R)-3-hydroxybutyryl CoA (Sigma Aldrich Japan Co.) and 0.1 g of bovine serum albumin (Sigma Co.) and mildly agitated for 3 hours at room temperature to execute PHA synthesis and evaporation of dichloromethane thereby solidifying the oil phase, and centrifuged at 1500 rpm. The obtained precipitate was re-dispersed in distilled water and the dispersion was further centrifuged to remove the free drug. The obtained microcapsules were re-dispersed in a small amount of distilled water, and lyophilized to obtain microcapsules 85 in powder form. The drug content in the microcapsules is shown in Tab. 11. The drug content was determined by HPLC method on 25 mg of microcapsules dissolved in 10 ml of phosphate buffer (pH 7.0) containing acetonitrile by 60%.

The prepared microcapsules 85 were suspended in 20 ml of chloroform and agitated for 20 hours at 60° C. to extract PHB constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHB monomer unit. As a result, it was confirmed that the external covering of the capsules 85 was PHB because the principal peak in the obtained chromatogram had the same retension time as that of the standard methylated compound of hydroxybutyric acid.

Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=78,000.

Example 97

The process of Example 96 was reproduced under the identical conditions except that the purified enzyme liquid (1) was replaced by crude enzyme liquid (1) to obtain capsules 86. The drug content in the microcapsules is shown in Tab. 11.

Evaluation as in Example 96 confirmed that the principal component of the outer covering of the obtained microcapsules 86 was PHB. Also based on the analysis by gel permeation chromatography, the number-averaged molecular weight of PHA contained in the obtained microcapsules 86 was 75,000.

Example 98

The process of Example 96 was reproduced under the identical conditions except that the purified enzyme liquid (1) was replaced by crude enzyme liquid (2) to obtain capsules 87. The drug content in the microcapsules is shown in Tab. 11.

Evaluation as in Example 96 confirmed that the principal component of the outer covering of the obtained microcapsules 87 was PHB. Also based on the analysis by gel permeation chromatography, the number-averaged molecular weight of PHA contained in the obtained microcapsules 87 was 74,000.

Example 99

The process of Example 96 was reproduced under the identical conditions except that the purified enzyme liquid (1) was replaced by purified enzyme liquid (2) and that (R)-3-hydroxybutyryl CoA was replaced by (R)-3-hydroxyoctanoyl CoA (prepared according to a method described in Eur. J. Biochem., 250, 432-439(1997)) to obtain capsules 88. The drug content in the microcapsules is shown in Tab. 11.

Evaluation as in Example 96 confirmed that the principal component of the outer covering of the obtained microcapsules 88 was PHA comprised of 3-hydroxyoctanoic acid unit. Also based on the analysis by gel permeation chromatography, the number-averaged molecular weight of PHA contained in the obtained microcapsules 88 was 25,000.

Example 100

The process of Example 96 was reproduced under the identical conditions except that the purified enzyme liquid (1) was replaced by purified enzyme liquid (3) and that (R)-3-hydroxybutyryl CoA was replaced by (R,S)-3-hydroxy-5-phenylvaleryl CoA (prepared by hydrolyzing 3-hydroxy-5-phenylvalerate ester obtained by a Reformatsky reaction, and then according to a method described in Eur. J. Biochem., 250, 432-439(1997)) to obtain capsules 89. The drug content in the microcapsules is shown in Tab. 11.

Evaluation as in Example 96 confirmed that the principal component of the outer covering of the obtained microcapsules 89 was PHA comprised of 3-hydroxy-5-phenylvaleryl acid unit. Also based on the analysis by gel permeation chromatography, the number-averaged molecular weight of PHA contained in the obtained microcapsules 89 was 22,000.

Example 101

The process of Example 96 was reproduced under the identical conditions except that the purified enzyme liquid (1)

was replaced by crude enzyme liquid (3) and that (R)-3-hydroxybutyryl CoA was replaced by (R,S)-3-hydroxy-5-phenoxyvaleryl CoA (prepared by starting from 3-phenoxypropanal synthesized according to J. Org. Chem., 55, 1490-1492(1990) and ethyl bromoacetate, hydrolyzing 3-hydroxy-5-phenylvalerate ester obtained by a zinc-based Reformatsky reaction, and then according to a method described in Eur. J. Biochem., 250, 432-439(1997)) to obtain capsules 90. The drug content in the microcapsules is shown in Tab. 11.

Evaluation as in Example 96 confirmed that the principal component of the outer covering of the obtained microcapsules 90 was PHA comprised of 3-hydroxy-5-phenoxyvaleric acid unit. Also based on the analysis by gel permeation chromatography, the number-averaged molecular weight of PHA contained in the obtained microcapsules 90 was 24,000.

Example 102

The process of Example 96 was reproduced under the identical conditions except that the purified enzyme liquid (1) was replaced by crude enzyme liquid (4) and that (R)-3-hydroxybutyryl CoA was replaced by (R,S)-3-hydroxy-5-phenylvaleryl CoA to start PHA synthesizing reaction. The reaction was conducted for 1 hour at room temperature, and, after addition of 1 g of (R,S)-3-hydroxy-5-phenoxyvaleryl CoA, was further conducted for 2 hours at room temperature. The process thereafter was conducted in the identical manner as in Example 96 to obtain capsules 91. The drug content in the microcapsules is shown in Tab. 11.

The mass of the polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-5-phenoxyvaleryl acid unit. Also in the measurement of similar TOF-SIMS mass spectrum gradually scraping the surface of the capsule construct by ion sputtering confirmed that the principal component of PHA constituting the capsule construct changed to 3-hydroxy-5-phenylvaleric acid unit at a certain point. These results confirmed that the capsule construct of the present example had a desired structure in which the drug 1 was covered by poly(3-hydroxy-5-phenylvaleric acid) and was further covered thereon by poly(3-hydroxy-5-phenoxyvaleric acid). Also based on the analysis by gel permeation chromatography, the number-averaged molecular weight of PHA contained in the obtained microcapsules 91 was 23,000.

Example 103

The process of Example 96 was reproduced under the identical conditions except that the purified enzyme liquid (1) was replaced by crude enzyme liquid (5) and that 1 g of (R)-3-hydroxybutyryl CoA was replaced by 0.8 g of (R,S)-3-hydroxy-5-phenylvaleryl CoA and 0.2 g of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)) to obtain capsules 92. The drug content in the microcapsules is shown in Tab. 11.

The result of 1H-NMR analysis (equipment: FT-NMR (Bruker DPX400); measured nuclide: 1H; solvent: CDCl$_3$ including TMS) indicated that the outer covering of the obtained capsules 92 was PHA comprised of 3-hydroxy-5-phenylvaleric acid unit by 75%, and 3-hydroxy-7,8-epoxyoctanoic acid unit by 25%. Also based on the analysis by gel permeation chromatography, the number-averaged molecular weight of PHA contained in the obtained microcapsules 92 was 20,000.

Example 104

50 parts of the above-mentioned microcapsules 92 were suspended in 50 parts of purified water. Then 0.5 parts of hexamethylene diamine were dissolved as a crosslinking agent in the suspension. After dissolution was confirmed, water was eliminated by lyophilization, and the mixture was reacted for 12 hours at 70° C. to obtain microcapsules 93. The content of peptide A in the microcapsules is shown in Tab. 11.

Further, the infrared absorption was measured with the microcapsules 93 (FT-IR; Perkin Elmer, 1720X). As a result, peaks of amine (at about 3340 cm$^{-1}$) and epoxy (at about 822 cm$^{-1}$), observed before heating, disappeared in the microcapsules 93. This indicates that the microcapsules 93 covered with the crosslinked polymer were obtained by the reaction of PHA having an epoxy unit in the side chain with hexamethylene diamine.

Example 105

50 parts of the aforementioned microcapsule 92 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain microcapsules 94 having a polysiloxane graft chain. The drug content in the microcapsules is shown in Tab. 11.

The infrared absorption measured on the microcapsules 94 (FT-IR; Perkin Elmer, 1720X) indicated that peaks of amine (about 3340 cm$^{-1}$) and epoxy (about 822 cm$^{-1}$), observed before heating, disappeared in the microcapsules 94. This result indicates that the microcapsules 94 having a polysiloxane graft chain were obtained by the reaction of PHA having an epoxy unit in the side chain with end-amino group modified polysiloxane.

TABLE 11

| Example | Capsule No. | Drug content (%) |
|---|---|---|
| 96 | 85 | 12.2 |
| 97 | 86 | 12.8 |
| 98 | 87 | 11.9 |
| 99 | 88 | 13.3 |
| 100 | 89 | 13.1 |
| 101 | 90 | 13.8 |
| 102 | 91 | 14.0 |
| 103 | 92 | 13.2 |
| 104 | 93 | 12.8 |
| 105 | 94 | 12.5 |

Experimental Example 10

62.8 mg of the microcapsules 81 obtained in Example 93 (corresponding to 30 mg drug/kg body weight) was dispersed in 0.5 ml of dispersion medium (distilled water dissolving 2.5 mg of carboxymethyl cellulose, 1.0 mg of polysorbate 80 and 25.0 mg of mannitol) and was injected subcutaneously with an injection needle 22G to the back of male SD rats of 10 weeks old. The rat was killed at every predetermined time after the administration, and the microcapsules remaining in the administered position were taken out. The amount of the drug in thus taken out microcapsules is shown in Tab. 12.

Experimental Examples 11~15 and Comparative Experimental Example 2

Experimental Example 10 was reproduced under the identical conditions except that the microcapsules 82, 83, 84, 92, 93 and 94 were respectively employed in an amount corresponding to 30 mg drug/kg body weight to analyse residual drug with time course. The residual rate is shown in Tab. 12.

TABLE 12

| Example | Microcapsules | Remaining ratio (%) at a time (week) after administration | | | |
|---|---|---|---|---|---|
| | | 1 | 2 | 3 | 4 |
| 1 | 81 | 87.3 | 59.2 | 10.7 | 2.4 |
| 2 | 82 | 91.1 | 68.3 | 23.2 | 8.7 |
| 3 | 82 | 88.4 | 62.1 | 13.2 | 4.1 |
| 4 | 92 | 88.8 | 62.2 | 12.3 | 3.4 |
| 5 | 93 | 90.1 | 66.0 | 25.1 | 9.9 |
| 6 | 94 | 86.7 | 61.4 | 15.2 | 4.9 |
| Comp. Ex. 2 | 84 | 85.2 | 58.2 | 6.2 | 0.5 |

Example 106

2.0 g of Example Compound 1 was dissolved in 20 ml of methylene chloride, to which 12 ml of purified water was added, and shaken and agitated to obtain a w/o emulsion. The diameter of the internal water phase was reduced by ultrasonic irradiation. Then under agitation with a small homogenizer (Kinematica), 32 ml of the w/o emulsion was poured into 200 ml of a 1 w/v % aqueous solution of polyvinyl alcohol to obtain a w/o/w emulsion. The w/o/w emulsion was agitated for 6 hours to evaporate methylene chloride thereby solidifying Example Compound 1 in the w/o emulsion. The fine particles were collected by centrifugation and washed with cold purified water, then re-dispersed in a 0.1% aqueous solution of Tween 80 and lyophilized to obtain hollow microcapsules 1 in powder form. Also ultrasonic contrast medium 1 was prepared with the hollow microcapsules 1.

The results of observation of the hollow microcapsule particles under an optical microscope and an electron microscope are shown in Tab. 13.

Examples 107 to 117

The process of Example 106 was reproduced except that Example Compounds 2 to 12 were employed as the polymer to be dissolved in the oil phase in the preparation of the w/o emulsion, thereby providing hollow microcapsules 2 to 12 in fine particle powder form. Also ultrasonic contrast media 2 to 12 were prepared respectively from these microcapsules.

The results of observation of the hollow microcapsule particles under an optical microscope and an electron microscope are shown in Tab. 13.

Example 118

50 parts of the above-mentioned hollow microcapsules 12 were suspended in 50 parts of purified water, and 0.5 parts of hexamethylene diamine were dissolved as a crosslinking agent in the suspension. After dissolution was confirmed, water was eliminated by lyophilization, and the mixture was reacted for 12 hours at 70° C. to obtain hollow microcapsules 13. Also an ultrasonic contrast medium 13 was prepared utilizing crosslinked hollow microcapsules 13. The results of observation under an optical microscope and an electron microscope are shown in Tab. 13.

Further, the infrared absorption was measured with the hollow microcapsules 13 (FT-IR; Perkin Elmer, 1720X). As a result, peaks of amine (at about 3340 $cm^{-1}$) and epoxy (at about 822 $cm^{-1}$), observed before heating, disappeared in the hollow microcapsules 13. This indicates that the hollow microcapsules 13 covered with the polymer, crosslinked by ring-opening addition of diamine and epoxy group, were obtained by the reaction of PHA having an epoxy unit in the side chain with hexamethylene diamine.

Example 119

50 parts of the aforementioned hollow microcapsule 12 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain microcapsules 14 having a polysiloxane graft chain, and an ultrasonic contrast medium 14 was prepared utilizing the hollow microcapsules 14 having a modification by a polysiloxane graft chain on the surface. The results of observation under an optical microscope and an electron microscope are shown in Tab. 13.

The infrared absorption measured on the hollow microcapsules 14 (FT-IR; Perkin Elmer, 1720X) indicated that peaks of amine (about 3340 $cm^{-1}$) and epoxy (about 822 $cm^{-1}$), observed before heating, disappeared in the hollow microcapsules 14. This result indicates that the hollow microcapsules 14 modified with a polysiloxane graft chain were obtained by ring-opening addition of epoxy group and end amino group by reacting PHA having an epoxy unit in the side chain with end-amino group modified polysiloxane.

Comparative Example 5

Example 106 was reproduced under the identical conditions, except that poly DL lactic acid (average molecular weight 7000) was employed as the polymer to be dissolved in the oil phase at the preparation of the w/o emulsion, to obtain hollow microcapsules 15, and ultrasonic contrast medium 15 was prepared utilizing the hollow microcapsules 15 comprised of poly DL lactic acid.

The results of observation under an optical microscope and an electron microscope are shown in Tab. 13.

TABLE 13

| Example | Hollow capsule No. | Example compound | Ave. part. size (μm) | Pore |
|---|---|---|---|---|
| 106 | 1 | 1 | 6/7 | none |
| 107 | 2 | 2 | 7.1 | none |
| 108 | 3 | 3 | 7.3 | none |
| 109 | 4 | 4 | 6.8 | none |
| 110 | 5 | 5 | 7.2 | none |
| 111 | 6 | 6 | 7.2 | none |
| 112 | 7 | 7 | 6.9 | none |
| 113 | 8 | 8 | 7.5 | none |
| 114 | 9 | 9 | 7.4 | none |
| 115 | 10 | 10 | 7.3 | none |
| 116 | 11 | 11 | 7.1 | none |
| 117 | 12 | 12 | 7.4 | none |
| 118 | 13 | 12 + crosslink | 7.5 | none |
| 119 | 14 | 12 + grafting | 7.7 | none |

TABLE 13-continued

| Example | Hollow capsule No. | Example compound | Ave. part. size (µm) | Pore |
|---|---|---|---|---|
| Comp. Ex. 5 | 15 | PLGA | 6.2 | present |

Pore: This shows indicates whether pores are formed in the outer covering by evaporation of water or organic solvent in the internal phase at the drying operation.

Example 120

An aqueous solution dissolving 0.6 ml of purified enzyme liquid (1), 300 mg of (R)-3-hydroxybutyryl CoA (Sigma Aldrich Japan Co.) and 12 mg of bovine serum albumin (Sigma) in 12 ml of 0.1 M phosphate buffer (pH 7.0) was added to 20 ml of methylene chloride. The obtained solution was shaken and agitated to obtain a w/o emulsion. The diameter of the internal water phase was reduced by ultrasonic irradiation. Then under agitation with a small homogenizer (Kinematica), 32 ml of the w/o emulsion was poured into 200 ml of an 1 w/v % aqueous solution of polyvinyl alcohol to obtain a w/o/w emulsion. The w/o/w emulsion was agitated for 6 hours to synthesize PHA and evaporate methylene chloride thereby solidifying Example Compound 1 in the w/o emulsion. The fine particles were collected by centrifugation and washed with cold purified water, then re-dispersed in a 0.1% aqueous solution of Tween 80 and lyophilized to obtain hollow microcapsules 16 in powder form. Also ultrasonic contrast medium 16 was prepared with the hollow microcapsules 16.

The results of observation of the hollow microcapsule particles under an optical microscope and an electron microscope are shown in Tab. 14.

The hollow capsules 16 were suspended in 20 mL of chloroform and agitated for 20 hours at 60° C. to extract PHB constituting the outer covering. The extract was filtered with a membrane filter of a pore size of 0.45 µm, then concentrated under a reduced pressure by a rotary evaporator, then subjected to methanolysis by a conventional method and analyzed in a gas chromatography mass spectrometer (GC-MS, Shimadzu QP-5050, EI method) to identify the methylester compound of the PHB monomer units. The main component of the outer covering of the obtained hollow capsules 16 was confirmed as PHB, since the peak of the main component in the obtained chromatogram had the same retension time as that of a methylated compound of standard hydroxybutyric acid.

Also the molecular weight of PHB was measured by gel permeation chromatography (GPC: TosoHLC-8020, column: Polymer Laboratory Plgel MIXED-C (5 µm), solvent: chloroform, column temperature: 40° C., converted into polystyrene) and was identified as Mn=72,000.

Example 121

The process of Example 120 was reproduced under the identical conditions except that the purified enzyme liquid (1) was replaced by crude enzyme liquid (1) derived from strain KK01 to obtain hollow capsules 17. Also an ultrasonic contrast medium 17 was prepared utilizing the hollow microcapsules 17. The results of observation of the microcapsule particles under an optical microscope and an electron microscope are shown in Tab. 14.

Evaluation as in Example 120 confirmed that the principal component of the outer covering of the obtained hollow microcapsules 17 was PHB. Also based on the analysis by gel permeation chromatography, the number-averaged molecular weight of PHA contained in the obtained hollow microcapsules 17 was 73,000.

Example 122

The process of Example 120 was reproduced under the identical conditions except that the purified enzyme liquid (1) was replaced by crude enzyme liquid (2) derived from the TL2 strain to obtain hollow capsules 18. Also an ultrasonic contrast medium 18 was prepared utilizing the hollow microcapsules 18.

The results of observation of the microcapsule particles under an optical microscope and an electron microscope are shown in Tab. 14.

Evaluation as in Example 120 confirmed that the principal component of the outer covering of the obtained hollow microcapsules 18 was PHB. Also based on the analysis by gel permeation chromatography, the number-averaged molecular weight of PHA contained in the obtained hollow microcapsules 18 was 72,000.

Example 123

The process of Example 120 was reproduced under the identical conditions except that the purified enzyme liquid (1) was replaced by purified enzyme liquid (2) of recombinant PHA synthetase and that (R)-3-hydroxybutyryl CoA was replaced by (R)-3-hydroxyoctanoyl CoA (prepared according to a method described in Eur. J. Biochem., 250, 432-439 (1997)) to obtain hollow capsules 19. Also an ultrasonic contrast medium 19 was prepared utilizing the hollow microcapsules 19.

The results of observation of the microcapsule particles under an optical microscope and an electron microscope are shown in Tab. 14.

Evaluation as in Example 120 confirmed that the principal component of the outer covering of the obtained hollow microcapsules 19 was PHA comprised of 3-hydroxyoctanoic acid unit. Also based on the analysis by gel permeation chromatography, the number-averaged molecular weight of PHA contained in the obtained hollow microcapsules 19 was 25,000.

Example 124

The process of Example 120 was reproduced under the identical conditions except that the purified enzyme liquid (1) was replaced by purified enzyme liquid (3) of recombinant PHA synthetase and that (R)-3-hydroxybutyryl CoA was replaced by (R,S)-3-hydroxy-5-phenylvaleryl CoA (prepared by hydrolyzing 3-hydroxy-5-phenylvalerate ester obtained by a Reformatsky reaction, and then according to a method described in Eur. J. Biochem., 250, 432-439(1997)) to obtain hollow capsules 20. Also an ultrasonic contrast medium 20 was prepared utilizing the hollow microcapsules 20.

The results of observation of the microcapsule particles under an optical microscope and an electron microscope are shown in Tab. 14.

Evaluation as in Example 120 confirmed that the principal component of the outer covering of the obtained hollow microcapsules 20 was PHA comprised of 3-hydroxy-5-phenylvaleryl acid unit. Also based on the analysis by gel permeation chromatography, the number-averaged molecular weight of PHA contained in the obtained hollow microcapsules 20 was 21,000.

Example 125

The process of Example 120 was reproduced under the identical conditions except that the purified enzyme liquid (1) was replaced by crude enzyme liquid (3) of recombinant PHA synthetase and that (R)-3-hydroxybutyryl CoA was replaced by (R,S)-3-hydroxy-5-phenoxyvaleryl CoA (prepared by starting from 3-phenoxypropanal synthesized according to J. Org. Chem., 55, 1490-1492(1990) and ethyl bromoacetate, hydrolyzing 3-hydroxy-5-phenylvalerate ester obtained by a zinc-based Reformatsky reaction, and then according to a method described in Eur. J. Biochem., 250, 432-439(1997)) to obtain hollow microcapsules 21. Also an ultrasonic contrast medium 21 was prepared utilizing the hollow microcapsules 21.

The results of observation of the microcapsule particles under an optical microscope and an electron microscope are shown in Tab. 14.

Evaluation as in Example 120 confirmed that the principal component of the outer covering of the obtained hollow microcapsules 21 was PHA comprised of 3-hydroxy-5-phenoxyvaleric acid unit. Also based on the analysis by gel permeation chromatography, the number-averaged molecular weight of PHA contained in the obtained hollow microcapsules 21 was 22,000.

Example 126

The process of Example 120 was reproduced under the identical conditions except that the purified enzyme liquid (1) was replaced by crude enzyme liquid (4) derived from the P91 strain and that (R)-3-hydroxybutyryl CoA was replaced by (R,S)-3-hydroxy-5-phenylvaleryl CoA to start PHA synthesizing reaction. The reaction was conducted for 1 hour at room temperature, and, after addition of 1 g of (R,S)-3-hydroxy-5-phenoxyvaleryl CoA, was further conducted for 2 hours at room temperature. The process thereafter was conducted in the identical manner as in Example 120 to obtain hollow capsules 22. Also an ultrasonic contrast medium 22 was prepared utilizing the hollow microcapsules 22.

The results of observation of the microcapsule particles under an optical microscope and an electron microscope are shown in Tab. 14.

The mass of the monomer unit fragments contained in the PHA polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-5-phenoxyvaleryl acid unit. Also in the measurement of the mass of the monomer unit fragments contained in the PHA polymer by a similar TOF-SIMS mass spectrum gradually scraping the surface of the capsule construct by ion sputtering confirmed that the principal component of of the monomer unit of PHA constituting the capsule construct changed to 3-hydroxy-5-phenylvaleric acid unit when sputtering proceeded to a certain depth. These results confirmed that the capsule construct of the present example had a desired two-layered structure in which poly(3-hydroxy-5-phenylvaleric acid) generated by the initial enzyme reaction was covered by poly(3-hydroxy-5-phenoxyvaleric acid) generated by an enzyme reaction at a later stage. Also based on the analysis by gel permeation chromatography, the number-averaged molecular weight of PHA contained in the obtained microcapsules 22 was 23,000.

Example 127

The process of Example 120 was reproduced under the identical conditions except that the purified enzyme liquid (1) was replaced by crude enzyme liquid (5) derived from the YN2 strain and that 300 mg of (R)-3-hydroxybutyryl CoA was replaced by 240 mg of (R,S)-3-hydroxy-5-phenylvaleryl CoA and 60 mg of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)) to obtain hollow microcapsules 23. Also an ultrasonic contrast medium 23 was prepared utilizing the hollow microcapsules 23.

The results of observation of the microcapsule particles under an optical microscope and an electron microscope are shown in Tab. 14.

The result of $^1$H-NMR analysis (equipment: FT-NMR (Bruker DPX400); measured nuclide: 1H; solvent: $CDCl_3$ including TMS) indicated that the outer covering of the obtained hollow microcapsules 23 was PHA comprised of 3-hydroxy-5-phenylvaleric acid unit by 77%, and 3-hydroxy-7,8-epoxyoctanoic acid unit by 23%. Also based on the analysis by gel permeation chromatography, the number-averaged molecular weight of PHA contained in the obtained microcapsules 23 was 25,000.

Example 128

50 parts of the above-mentioned hollow microcapsules 23 were suspended in 50 parts of purified water. Then 0.5 parts of hexamethylene diamine were dissolved as a crosslinking agent in the suspension. After dissolution was confirmed, water was eliminated by lyophilization, and the mixture was reacted for 12 hours at 70° C. to obtain hollow microcapsules 24 having surface crosslinking. Also an ultrasonic contrast medium 24 was prepared utilizing the hollow crosslinked microcapsules 24.

The results of observation of the microcapsule particles under an optical microscope and an electron microscope are shown in Tab. 14.

Further, the infrared absorption was measured with the hollow microcapsules 24 (FT-IR; Perkin Elmer, 1720X). As a result, peaks of amine (at about 3340 $cm^{-1}$) and epoxy (at about 822 $cm^{-1}$) observed before heating disappeared in the hollow microcapsules 24. This indicates that the hollow microcapsules 24 covered with the polymer crosslinked by ring-opening addition of diamine and epoxy group were obtained by the reaction of PHA having an epoxy unit in the side chain with hexamethylene diamine.

Example 129

50 parts of the aforementioned microcapsule 23 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain hollow microcapsules 25 having a polysiloxane graft chain. Also an ultrasonic contrast medium 25 was prepared utilizing the hollow microcapsules 25. The results of observation of the microcapsule particles under an optical microscope and an electron microscope are shown in Tab. 14.

The infrared absorption measured on the hollow microcapsules 25 (FT-IR; Perkin Elmer, 1720X) indicated that peaks of amine (about 3340 $cm^{-1}$) and epoxy (about 822 $cm^{-1}$), observed before heating, disappeared in the hollow microcapsules 25. This result indicates that the hollow microcapsules 25 having chemical modification by a polysiloxane graft chain, through ring-opening addition of epoxy group and end amino group, were obtained by the reaction of PHA having an epoxy unit in the side chain with end-amino group modified polysiloxane.

TABLE 14

| Example | Hollow capsule No. | Average particle size | Pore |
|---|---|---|---|
| 120 | 16 | 6.7 | none |
| 121 | 17 | 6.9 | none |
| 122 | 18 | 7.1 | none |
| 123 | 19 | 7.8 | none |
| 124 | 20 | 7.4 | none |
| 125 | 21 | 6.9 | none |
| 126 | 22 | 7.5 | none |
| 127 | 23 | 7.2 | none |
| 128 | 24 | 7.4 | none |
| 129 | 25 | 7.3 | none |

Example 130

20 ml of methylene chloride was added with 12 ml of purified water, and was shaken and agitated to obtain a w/o emulsion. The diameter of the internal water phase was reduced by ultrasonic irradiation. Then under agitation with a small homogenizer (Kinematica), 32 ml of the w/o emulsion was poured into 100 ml of 0.1 M phosphate buffer (pH 7.0) containing therein 1 w/v % of polyvinyl alcohol, 5 ml of the purified enzyme liquid (1), 1 g of (R)-3-hydroxybutyryl CoA (Sigma Aldrich Japan) and 100 mg of bovine albumin (Sigma Co.) to obtain a w/o/w emulsion. The w/o/w emulsion was agitated for 6 hours to synthesize PHA and evaporate methylene chloride thereby solidifying the generated PHA and preparing fine microcapsule particles. The fine particles were collected by centrifugation under simultaneous washing with cooled purified water, then re-dispersed in 0.1% aqueous solution of Tween 80 and lyophilized to obtain hollow microcapsules 26 in powder form. Also ultrasonic contrast medium 26 was prepared with the hollow microcapsules 26.

The results of observation of the hollow microcapsule particles under an optical microscope and an electron microscope are shown in Tab. 15.

The hollow microcapsules 26 were suspended in 20 ml of chloroform and agitated for 20 hours at 60° C. to extract PHB constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHB monomer unit. As a result, it was confirmed that the external covering of the hollow capsules 26 was PHB because the principal peak in the obtained chromatogram had the same retension time as that of the standard methyl esterified compound of hydroxybutyric acid.

Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=71,000.

Example 131

The process of Example 130 was reproduced under the identical conditions except that the purified enzyme liquid (1) was replaced by crude enzyme liquid (1) derived from the KK01 strain to obtain hollow capsules 27. Also an ultrasonic contrast medium 27 was prepared utilizing the hollow microcapsules 27. The results of observation of the microcapsule particles under an optical microscope and an electron microscope are shown in Tab. 15.

Evaluation as in Example 130 confirmed that the principal component of the outer covering of the obtained hollow microcapsules 27 was PHB. Also based on the analysis by gel permeation chromatography, the number-averaged molecular weight of PHA contained in the obtained hollow microcapsules 27 was 76,000.

Example 132

The process of Example 130 was reproduced under the identical conditions except that the purified enzyme liquid (1) was replaced by crude enzyme liquid (2) derived from the TL2 strain to obtain hollow capsules 28. Also an ultrasonic contrast medium 28 was prepared utilizing the hollow microcapsules 28.

The results of observation of the microcapsule particles under an optical microscope and an electron microscope are shown in Tab. 15.

Evaluation as in Example 130 confirmed that the principal component of the outer covering of the obtained hollow microcapsules 28 was PHB. Also based on the analysis by gel permeation chromatography, the number-averaged molecular weight of PHA contained in the obtained hollow microcapsules 28 was 75,000.

Example 133

The process of Example 130 was reproduced under the identical conditions except that the purified enzyme liquid (1) was replaced by purified enzyme liquid (2) derived from TL2 strain and that (R)-3-hydroxybutyryl CoA was replaced by (R)-3-hydroxyoctanoyl CoA (prepared according to a method described in Eur. J. Biochem., 250, 432-439(1997)) to obtain hollow capsules 29. Also an ultrasonic contrast medium 29 was prepared utilizing the hollow microcapsules 29.

The results of observation of the microcapsule particles under an optical microscope and an electron microscope are shown in Tab. 15.

Evaluation as in Example 130 confirmed that the principal component of the outer covering of the obtained hollow microcapsules 29 was PHA comprised of 3-hydroxyoctanoic acid unit. Also based on the analysis by gel permeation chromatography, the number-averaged molecular weight of PHA contained in the obtained hollow microcapsules 29 was 25,000.

Example 134

The process of Example 130 was reproduced under the identical conditions except that the purified enzyme liquid (1) was replaced by purified enzyme liquid (3) of derived from P91 strain and that (R)-3-hydroxybutyryl CoA was replaced by (R,S)-3-hydroxy-5-phenylvaleryl CoA (prepared by hydrolyzing 3-hydroxy-5-phenylvalerate ester obtained by a Reformatsky reaction, and then according to a method described in Eur. J. Biochem., 250, 432-439(1997)) to obtain hollow capsules 30. Also an ultrasonic contrast medium 30 was prepared utilizing the hollow microcapsules 30.

The results of observation of the microcapsule particles under an optical microscope and an electron microscope are shown in Tab. 15.

Evaluation as in Example 130 confirmed that the principal component of the outer covering of the obtained hollow microcapsules 30 was PHA comprised of 3-hydroxy-5-phenylvaleryl acid unit. Also based on the analysis by gel permeation chromatography, the number-averaged molecular weight of PHA contained in the obtained hollow microcapsules 30 was 21,000.

Example 135

The process of Example 130 was reproduced under the identical conditions except that the purified enzyme liquid (1) was replaced by crude enzyme liquid (3) derived from P91 strain and that (R)-3-hydroxybutyryl CoA was replaced by (R,S)-3-hydroxy-5-phenoxyvaleryl CoA (prepared by starting from 3-phenoxypropanal synthesized according to J. Org. Chem., 55, 1490-1492(1990) and ethyl bromoacetate, hydrolyzing 3-hydroxy-5-phenylvalerate ester obtained by a zinc-based Reformatsky reaction, and then according to a method described in Eur. J. Biochem., 250, 432-439(1997)) to obtain hollow microcapsules 31. Also an ultrasonic contrast medium 31 was prepared utilizing the hollow microcapsules 31.

The results of observation of the microcapsule particles under an optical microscope and an electron microscope are shown in Tab. 15.

Evaluation as in Example 130 confirmed that the principal component of the outer covering of the obtained hollow microcapsules 21 was PHA comprised of 3-hydroxy-5-phenoxyvaleric acid unit. Also based on the analysis by gel permeation chromatography, the number-averaged molecular weight of PHA contained in the obtained hollow microcapsules 31 was 23,000.

Example 136

The process of Example 130 was reproduced under the identical conditions except that the purified enzyme liquid (1) was replaced by crude enzyme liquid (4) and that (R)-3-hydroxybutyryl CoA was replaced by (R,S)-3-hydroxy-5-phenylvaleryl CoA to start PHA synthesizing reaction. The reaction was conducted for 1 hour at room temperature, and, after addition of 1 g of (R,S)-3-hydroxy-5-phenoxyvaleryl CoA, was further conducted for 2 hours at room temperature. The process thereafter was conducted in the identical manner as in Example 130 to obtain hollow capsules 32. Also an ultrasonic contrast medium 32 was prepared utilizing the hollow microcapsules 32.

The results of observation of the microcapsule particles under an optical microscope and an electron microscope are shown in Tab. 15.

The mass of the polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-5-phenoxyvaleryl acid unit. Also in the measurement of the similar TOF-SIMS mass spectrum gradually scraping the surface of the capsule construct by ion sputtering confirmed that the principal component of the monomer unit of PHA constituting the capsule construct changed to 3-hydroxy-5-phenylvaleric acid unit at a certain point. These results confirmed that the capsule construct of the present example had a desired two-layered structure in which poly (3-hydroxy-5-phenylvaleric acid) initially generated was covered by poly(3-hydroxy-5-phenoxyvaleric acid) generated in a later stage. Also based on the analysis by gel permeation chromatography, the number-averaged molecular weight of PHA contained in the obtained microcapsules 32 was 22,000.

Example 137

The process of Example 130 was reproduced under the identical conditions except that the purified enzyme liquid (1) was replaced by crude enzyme liquid (5) and that 1 g of (R)-3-hydroxybutyryl CoA was replaced by 800 mg of (R,S)-3-hydroxy-5-phenylvaleryl CoA and 200 mg of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)) to obtain hollow microcapsules 33. Also an ultrasonic contrast medium 33 was prepared utilizing the hollow microcapsules 33.

The results of observation of the microcapsule particles under an optical microscope and an electron microscope are shown in Tab. 15.

The result of $^1$H-NMR analysis (equipment: FT-NMR (Bruker DPX400); measured nuclide: 1H; solvent: $CDCl_3$ including TMS) indicated that the outer covering of the obtained hollow microcapsules 33 was PHA comprised of 3-hydroxy-5-phenylvaleric acid unit by 76%, and 3-hydroxy-7,8-epoxyoctanoic acid unit by 24%. Also based on the analysis by gel permeation chromatography, the number-averaged molecular weight of PHA contained in the obtained microcapsules 33 was 23,000.

Example 138

50 parts of the above-mentioned hollow microcapsules 33 were suspended in 50 parts of purified water. Then 0.5 parts of hexamethylene diamine were dissolved as a crosslinking agent in the suspension. After dissolution was confirmed, water was eliminated by lyophilization, and the mixture was reacted for 12 hours at 70° C. to obtain hollow microcapsules 34 having surface crosslinking. Also an ultrasonic contrast medium 34 was prepared utilizing the hollow crosslinked microcapsules 34.

The results of observation of the microcapsule particles under an optical microscope and an electron microscope are shown in Tab. 15.

Further, the infrared absorption was measured with the hollow microcapsules 34 (FT-IR; Perkin Elmer, 1720X). As a result, peaks of amine (at about 3340 $cm^{-1}$) and epoxy (at about 822 $cm^{-1}$) observed before heating disappeared in the hollow microcapsules 34. This indicates that the hollow microcapsules 34 covered with the crosslinked polymer were obtained by the reaction of PHA having an epoxy unit in the side chain with hexamethylene diamine.

Example 139

50 parts of the aforementioned hollow microcapsule 33 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain hollow microcapsules 35 having a polysiloxane graft chain. Also an ultrasonic contrast medium 35 was prepared utilizing the hollow microcapsules 35.

The results of observation of the microcapsule particles under an optical microscope and an electron microscope are shown in Tab. 15.

The infrared absorption measured on the hollow microcapsules 35 (FT-IR; Perkin Elmer, 1720X) indicated that peaks of amine (about 3340 $cm^{-1}$) and epoxy (about 822 $cm^{-1}$), observed before heating, disappeared in the hollow microcapsules 35. This result indicates that the hollow microcapsules 35 having chemical modification by a polysiloxane graft chain were obtained by the reaction of PHA having an epoxy unit in the side chain with end-amino group modified polysiloxane.

TABLE 15

| Example | Hollow capsule No. | Average particle size (μm) | Pore |
|---|---|---|---|
| 130 | 26 | 6.8 | none |
| 131 | 27 | 6.9 | none |
| 132 | 28 | 7.3 | none |
| 133 | 29 | 8.1 | none |
| 134 | 30 | 7.7 | none |
| 135 | 31 | 7.5 | none |
| 136 | 32 | 7.7 | none |
| 137 | 33 | 7.5 | none |
| 138 | 34 | 7.7 | none |
| 139 | 35 | 7.7 | none |

Example 140

2 ml of dichloromethane was cooled to 16 to 18° C. and was poured into 100 ml of 0.1 M phosphate buffer (pH 7.0) containing 0.1% polyvinyl alcohol (EG-40, Nippon Synthetic Chemicals Co.) cooled to 16 to 18° C. in advance, and was formed into an o/w emulsion by a turbine-type homomixer (Tokushu Kika (Co.) at 7000 rpm. The o/w emulsion was added with 5 ml of the purified enzyme liquid (1), 1 g of (R)-3-hydroxybutyryl CoA (Sigma Aldrich Japan Co.) and 0.1 g of bovine serum albumin (Sigma Co.) and mildly agitated for 3 hours at room temperature to execute PHA synthesis and evaporation of dichloromethane thereby solidifying the oil phase, and centrifuged at 1500 rpm. The obtained precipitate was re-dispersed in distilled water and the dispersion was further centrifuged to remove the free drug. The obtained microcapsules were re-dispersed in a small amount of distilled water, and lyophilized to obtain hollow microcapsules 36 in powder form. Also an ultrasonic contrast medium 36 was prepared utilizing the hollow microcapsules 36.

The results of observation of the microcapsule particles under an optical microscope and an electron microscope are shown in Tab. 16.

The hollow microcapsules 36 were suspended in 20 ml of chloroform and agitated for 20 hours at 60° C. to extract PHB constituting the external covering. The extract was filtered through a membrane filter of 0.45 μm pore size and concentrated under a reduced pressure by using a rotary evaporator. Then the extract was subjected to methanolysis by a conventional method and analyzed by gas chromatography-mass spectroscopy (GC-MS, Shimadzu QP-5050, an EI method) to identify the methyl-esterified PHB monomer unit. As a result, it was confirmed that the external covering of the hollow capsules 36 was PHB because the principal peak in the obtained chromatogram had the same retension time as that of the standard methylated compound of hydroxybutyric acid.

Further, the molecular weight of PHA was evaluated by gel permeation chromatography (GPC: Toso HLC-8020, column: Polymer Laboratory PLgel MIXED-C (5 μm), solvent: chloroform, converted as polystyrene) to obtain a result Mn=75,000.

Example 141

The process of Example 140 was reproduced under the identical conditions except that the purified enzyme liquid (1) was replaced by crude enzyme liquid (1) to obtain hollow capsules 37. Also an ultrasonic contrast medium 37 was prepared utilizing the hollow microcapsules 37. The results of observation of the microcapsule particles under an optical microscope and an electron microscope are shown in Tab. 16.

Evaluation as in Example 140 confirmed that the principal component of the outer covering of the obtained hollow microcapsules 37 was PHB. Also based on the analysis by gel permeation chromatography, the number-averaged molecular weight of PHA contained in the obtained hollow microcapsules 37 was 73,000.

Example 142

The process of Example 140 was reproduced under the identical conditions except that the purified enzyme liquid (1) was replaced by crude enzyme liquid (2) to obtain hollow capsules 38. Also an ultrasonic contrast medium 38 was prepared utilizing the hollow microcapsules 38.

The results of observation of the microcapsule particles under an optical microscope and an electron microscope are shown in Tab. 16.

Evaluation as in Example 140 confirmed that the principal component of the outer covering of the obtained hollow microcapsules 38 was PHB. Also based on the analysis by gel permeation chromatography, the number-averaged molecular weight of PHA contained in the obtained hollow microcapsules 38 was 71,000.

Example 143

The process of Example 140 was reproduced under the identical conditions except that the purified enzyme liquid (1) was replaced by purified enzyme liquid (2) and that (R)-3-hydroxybutyryl CoA was replaced by (R)-3-hydroxyoctanoyl CoA (prepared according to a method described in Eur. J. Biochem., 250, 432-439(1997)) to obtain hollow capsules 39. Also an ultrasonic contrast medium 39 was prepared utilizing the hollow microcapsules 39.

The results of observation of the microcapsule particles under an optical microscope and an electron microscope are shown in Tab. 16.

Evaluation as in Example 140 confirmed that the principal component of the outer covering of the obtained hollow microcapsules 39 was PHA comprised of 3-hydroxyoctanoic acid unit. Also based on the analysis by gel permeation chromatography, the number-averaged molecular weight of PHA contained in the obtained hollow microcapsules 39 was 23,000.

Example 144

The process of Example 140 was reproduced under the identical conditions except that the purified enzyme liquid (1)

was replaced by purified enzyme liquid (3) and that (R)-3-hydroxybutyryl CoA was replaced by (R,S)-3-hydroxy-5-phenylvaleryl CoA (prepared by hydrolyzing 3-hydroxy-5-phenylvalerate ester obtained by a Reformatsky reaction, and then according to a method described in Eur. J. Biochem., 250, 432-439(1997)) to obtain hollow capsules 40. Also an ultrasonic contrast medium 40 was prepared utilizing the hollow microcapsules 40.

The results of observation of the microcapsule particles under an optical microscope and an electron microscope are shown in Tab. 16.

Evaluation as in Example 140 confirmed that the principal component of the outer covering of the obtained hollow microcapsules 40 was PHA comprised of 3-hydroxy-5-phenylvaleryl acid unit. Also based on the analysis by gel permeation chromatography, the number-averaged molecular weight of PHA contained in the obtained hollow microcapsules 40 was 20,000.

Example 145

The process of Example 140 was reproduced under the identical conditions except that the purified enzyme liquid (1) was replaced by crude enzyme liquid (3) and that (R)-3-hydroxybutyryl CoA was replaced by (R,S)-3-hydroxy-5-phenoxyvaleryl CoA (prepared by starting from 3-phenoxypropanal synthesized according to J. Org. Chem., 55, 1490-1492(1990) and ethyl bromoacetate, hydrolyzing 3-hydroxy-5-phenylvalerate ester obtained by a zinc-based Reformatsky reaction, and then according to a method described in Eur. J. Biochem., 250, 432-439(1997)) to obtain hollow microcapsules 41. Also an ultrasonic contrast medium 41 was prepared utilizing the hollow microcapsules 41.

The results of observation of the microcapsule particles under an optical microscope and an electron microscope are shown in Tab. 16.

Evaluation as in Example 140 confirmed that the principal component of the outer covering of the obtained hollow microcapsules 41 was PHA comprised of 3-hydroxy-5-phenoxyvaleric acid unit. Also based on the analysis by gel permeation chromatography, the number-averaged molecular weight of PHA contained in the obtained hollow microcapsules 41 was 24,000.

Example 146

The process of Example 140 was reproduced under the identical conditions except that the purified enzyme liquid (1) was replaced by crude enzyme liquid (4) and that (R)-3-hydroxybutyryl CoA was replaced by (R,S)-3-hydroxy-5-phenonylvaleryl CoA to start PHA synthesizing reaction. The reaction was conducted for 1 hour at room temperature, and, after addition of 1 g of (R,S)-3-hydroxy-5-phenoxyvaleryl CoA, was further conducted for 2 hours at room temperature. The process thereafter was conducted in the identical manner as in Example 140 to obtain hollow capsules 42. Also an ultrasonic contrast medium 42 was prepared utilizing the hollow microcapsules 42.

The results of observation of the microcapsule particles under an optical microscope and an electron microscope are shown in Tab. 16.

The mass of the polymer formed on the surface of the capsule construct was measured by a time-of-flight secondary ion mass spectrometer (TOF-SIMS IV, CAMECA). The obtained mass spectrum confirmed that PHA at the surface of the capsule construct was principally comprised of 3-hydroxy-5-phenoxyvaleryl acid unit. Also in the measurement of the similar TOF-SIMS mass spectrum gradually scraping the surface of the capsule construct by ion sputtering confirmed that the principal component of the monomer unit of PHA constituting the capsule construct changed to 3-hydroxy-5-phenylvaleric acid unit at a certain point. These results confirmed that the capsule construct of the present example had a desired two-layered structure in which poly (3-hydroxy-5-phenylvaleric acid) initially generated was covered by poly(3-hydroxy-5-phenoxyvaleric acid) generated in a later stage. Also based on the analysis by gel permeation chromatography, the number-averaged molecular weight of PHA contained in the obtained microcapsules 42 was 21,000.

Example 147

The process of Example 140 was reproduced under the identical conditions except that the purified enzyme liquid (1) was replaced by crude enzyme liquid (5) and that 1 g of (R)-3-hydroxybutyryl CoA was replaced by 800 mg of (R,S)-3-hydroxy-5-phenylvaleryl CoA and 200 mg of (R,S)-3-hydroxy-7,8-epoxyoctanoyl CoA (prepared by synthesizing 3-hydroxy-7-octenoic acid according to Int. J. Biol. Macromol., 12, 85-91(1990), then epoxylating an unsaturated portion thereof with 3-chlorobenzoic acid, and then preparing according to a method described in Eur. J. Biochem., 250, 432-439(1997)) to obtain hollow microcapsules 43. Also an ultrasonic contrast medium 43 was prepared utilizing the hollow microcapsules 43.

The results of observation of the microcapsule particles under an optical microscope and an electron microscope are shown in Tab. 16.

The result of 1H-NMR analysis (equipment: FT-NMR (Bruker DPX400); measured nuclide: 1H; solvent: $CDCl_3$ including TMS) indicated that the outer covering of the obtained hollow microcapsules 43 was PHA comprised of 3-hydroxy-5-phenylvaleric acid unit by 75%, and 3-hydroxy-7,8-epoxyoctanoic acid unit by 25%. Also based on the analysis by gel permeation chromatography, the number-averaged molecular weight of PHA contained in the obtained microcapsules 43 was 21,000.

Example 148

50 parts of the above-mentioned hollow microcapsules 43 were suspended in 50 parts of purified water. Then 0.5 parts of hexamethylene diamine were dissolved as a crosslinking agent in the suspension. After dissolution was confirmed, water was eliminated by lyophilization, and the mixture was reacted for 12 hours at 70° C. to obtain hollow microcapsules 44 having surface crosslinking. Also an ultrasonic contrast medium 44 was prepared utilizing the hollow crosslinked microcapsules 44.

The results of observation of the microcapsule particles under an optical microscope and an electron microscope are shown in Tab. 16.

Further, the infrared absorption was measured with the hollow microcapsules 44 (FT-IR; Perkin Elmer, 1720X). As a result, peaks of amine (at about 3340 $cm^{-1}$) and epoxy (at about 822 $cm^{-1}$) observed before heating disappeared in the hollow microcapsules 44. This indicates that the hollow microcapsules 44 covered with the crosslinked polymer were obtained by the reaction between PHA having an epoxy unit in the side chain with hexamethylene diamine.

Example 149

50 parts of the aforementioned hollow microcapsule 43 were added with 10 parts of end-amino-group modified polysiloxane (modified silicone oil TSF4700, GE-Toshiba Silicone Co.) and were reacted for 2 hours at 70° C. The reaction product was then washed and dried by repeated suspension in methanol and centrifugation (10,000×g, 4° C., 20 min.) to obtain hollow microcapsules 45 having a polysiloxane graft chain. Also an ultrasonic contrast medium 45 was prepared utilizing the hollow microcapsules 45.

The results of observation of the microcapsule particles under an optical microscope and an electron microscope are shown in Tab. 16.

The infrared absorption measured on the hollow microcapsules 45 (FT-IR; Perkin Elmer, 1720X) indicated that peaks of amine (about 3340 $cm^{-1}$) and epoxy (about 822 $cm^{-1}$) observed before heating, disappeared in the hollow microcapsules 45. This result indicates that the hollow microcapsules 45 having chemical modification by a polysiloxane graft chain were obtained by the reaction between PHA having an epoxy unit in the side chain and the end-amino group modified polysiloxane.

TABLE 16

| Example | Hollow capsule No. | Average particle size (μm) | Pore |
| --- | --- | --- | --- |
| 140 | 36 | 6.9 | none |
| 141 | 37 | 6.9 | none |
| 142 | 38 | 7.1 | none |
| 143 | 39 | 7.4 | none |
| 144 | 40 | 7.5 | none |
| 145 | 41 | 7.5 | none |
| 146 | 42 | 7.3 | none |
| 147 | 43 | 7.7 | none |
| 148 | 44 | 7.8 | none |
| 149 | 45 | 7.7 | none |

Experimental Example 16

In vitro Test of Ultrasnoic Contrast Effect

Ultrasonic contrast effect of the ultrasonic contrast medium utilizing the hollow microcapsules was investigated with a test apparatus shown in FIGURE. A polypropylene container 1 containing 100 ml of physiological saline was fixed in a water tank 2, and a stirrer bar 3 was placed in the container 1 to agitate the content using a magnetic stirrer. Each of the hollow microcapsule particles obtained in the foregoing Examples and Comparative Examples was suspended in 1 ml of an 1 w/v % Tween 80 aqueous solution at several concentrations and poured into the physiological saline in the container 1. Then an ultrasonic image diagnosis apparatus (SONOLAYER αSSH-140, Toshiba) equipped with a sector probe having a central frequency of 5 MHz was used to execute a scanning operation in such a manner that the container 1 was positioned at the center of the image. Then, in a still state of the contrast enhanced image, the luminance of the bright spots in front of the container 1 or in the entire container 1 as an index for the ultrasonic contrast effect.

One mililiter of respective solutions of ultrasonic contrast media 12 to 14, 23 to 25, 33 to 35, 43 to 45 and 15 utilizing the fine microcapsule particles obtained in Examples 117 to 119, 127 to 129, 137 to 139, 147 to 149 and Comparative Example 5 of different concentrations was added to 100 ml of the forementioned physiological saline to give different suspension density, and the change with time of the bright spot in front of the container 1 was studied.

As a result, with any of the ultrasonic contrast media 12 to 14, 23 to 25, 33 to 35 and 43 to 45, the averaged initial luminance of the bright spots was constant within a range of 25 to 30 when the added amount does not exceed 20 mg. On the other hand, the rate of attenuation with time varied depending on the added amount (suspended concentration), and the lower the suspension concentration, the higher the attenuation rate. For example, when the addition amount was 5 or 2.5 mg, the average luminance of the bright spots became lower than 20 in about 5 minutes after charging. On the other hand, when the addition amount was 10 or 20 mg, the average luminance of the bright spots was 20 or more even after 30 minutes from the charging.

On the other hand, when the addition amount of the hollow microcapsule particles was 40 mg or more, there was initial acoustic shadowing, and the initial luminance of the bright spots was about 23 which was lower than when 10 or 20 mg was added, but the luminance of the bright spots increased with time as dispersion proceeded after charging, and reached about 28 in about 10 minutes. Thereafter, the high luminance of the bright spots was retained for a while with a high suspension concentration of the particles (80 mg) or gradually attenuated with a lower suspension concentration (40 mg), but, with any concentration, the averaged luminance of the bright spots was 25 or higher even at 30 minutes after the luminance of the bright spots reached a peak.

Consequently a high contrast effect can be attained for a prolonged period by preparing the hollow PHA microcapsules of the present invention into an ultrasonic contrast medium to be used at a suspended concentration of 10 mg or higher per 1 ml of water.

On the other hand, in the ultrasonic contrast medium 15 utilizing the hollow microcapsules 15 prepared with poly-DL-lactic acid (average molecular weight 7000), in any suspended concentration, though the average luminance of the bright spots was initially 20 or higher, it rapidly attenuated thereafter to 10 or less after 5 minutes and about 5 after 10 minutes. Therefore, the continuity of the contrast effect after charging was inferior to that of the ultrasonic contrast medium of the present invention.

What is claimed is:

1. A particulate construct, comprising:

an external solid phase containing a first and a second polyhydroxyalkanoate that are different; and an internal phase incorporated in said external solid phase, wherein said internal phase is at least one of a solid phase, a liquid phase or a gaseous phase, wherein the external solid phase has a gradient structure in which the monomer unit composition of said polyhydroxyalkanoates changes along a direction from the inner side to the outer side of said particulate construct, and wherein said first polyhydroxyalkanoate comprises at least one monomer unit selected from the group consisting of monomer units represented by chemical formulae:

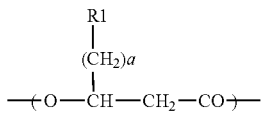

[1]

wherein R1 and a are selected from the group of combinations consisting of:

R1 is a hydrogen atom (H) and a is 0 or any of integers from 3 to 10;

R1 is a halogen atom and a is any of integers from 1 to 10;

R1 is a chromophore and a is any of integers from 1 to 10;

R1 is a carboxyl group or a salt thereof and a is any of integers from 1 to 10; and R1 is

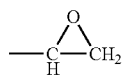

and a is any of integers from 1 to 7;

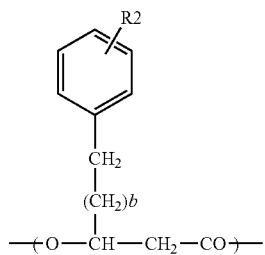 [2]

wherein b represents any of integers from 0 to 7 and R2 is selected from a group consisting of a hydrogen atom (H), a halogen atom, —CN, —NO$_2$, —CF$_3$, —C$_2$F$_5$, and —C$_3$F$_7$);

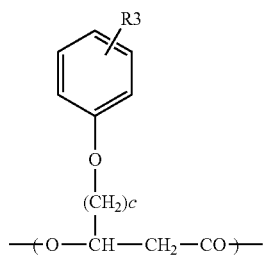 [3]

wherein c represents any of integers from 1 to 8 and R3 is selected from a group consisting of a hydrogen atom (H), a halogen atom, —CN, —NO$_2$, —CF$_3$, —C$_2$F$_5$, and —C$_3$F$_7$;

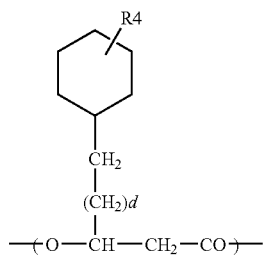 [4]

wherein d represents any of integers from 0 to 7 and R4 is selected from a group consisting of a hydrogen atom (H), a halogen atom, —CN, —NO$_2$, —CF$_3$, —C$_2$F$_5$, and —C$_3$F$_7$;

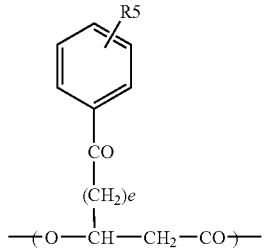 [5]

wherein e represents any of integers from 1 to 8 and R5 is selected from a group consisting of a hydrogen atom (H), a halogen atom, —CN, —NO$_2$, —CF$_3$, —C$_2$F$_5$, —C$_3$F$_7$, —CH$_3$, —C$_2$H$_5$, and —C$_3$H$_7$;

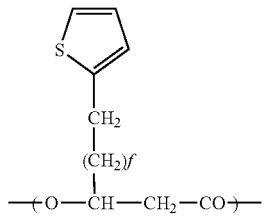 [6]

wherein f represents any of integers from 0 to 7;

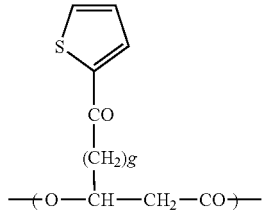 [7]

wherein g represents any of integers from 1 to 8;

[8]

wherein h represents any of integers from 1 to 7 and R6 is selected from a group consisting of a hydrogen atom (H), a halogen atom, —CN, —NO$_2$, —COOR', —SO$_2$R", CH$_3$, —C$_2$H$_5$, —C$_3$H$_7$, —CH(CH$_3$)$_2$, and —C(CH$_3$)$_3$, wherein R' is selected from a group consisting of a hydrogen atom (H), Na, K, —CH$_3$, and —C$_2$H$_5$, and R" is selected from a group consisting of —OH, —ONa, —OK, a halogen atom, —OCH$_3$, and —OC$_2$H$_5$;

[9]

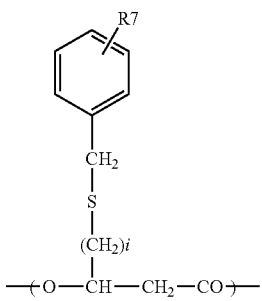

wherein i represents any of integers from 1 to 7 and R7 is selected from a group consisting of a hydrogen atom (H), a halogen atom, —CN, —$NO_2$, —COOR', —$SO_2$R", wherein R' is selected from a group consisting of a hydrogen atom (H), Na, K, —$CH_3$, and —$C_2H_5$, and R" is selected from a group consisting of —OH, —ONa, —OK, halogen atoms, —$OCH_3$, and —$OC_2H_5$; and

[10]

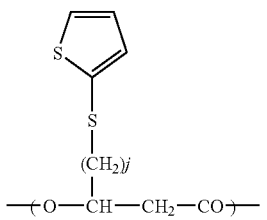

wherein j represents any of integers from 1 to 9.

2. A particulate construct according to claim 1, having the form of a microcapsule of a configuration incorporating a core portion in a shell, wherein said polyhydroxyalkanoates are contained in said shell, and at least a phase of said internal phase is contained in said core portion.

3. A particulate construct according to claim 1, wherein the number-averaged molecular weight of said first polyhydroxyalkanoate is 5,000 to 1,000,000.

4. A particulate construct according to claim 1, wherein at least a part of said first polyhydroxyalkanoate is chemically modified, and wherein said chemically modified polyhydroxyalkanoate has a graft chain made with a terminal amino-modified compound selected from a group consisting of polyvinylamine, polyethyleneimine, and terminal amino-modified polysiloxane.

5. A particulate construct according to claim 1, wherein at least a part of said polyhydroxyalkanoates are crosslinked.

6. A particulate construct according to claim 5, wherein said crosslinked polyhydroxyalkanoates are formed by crosslinking polyhydroxyalkanoate containing at least a monomer unit having an epoxy group.

7. A particulate construct according to claim 5, wherein said crosslinked polyhydroxyalkanoates are crosslinked by at least one selected from a group consisting of a diamine compound, succinic anhydride, 2-ethyl-4-imidazole and electron beam irradiation.

8. A particulate construct according to claim 1, wherein said internal phase contains a pharmaceutical component.

9. A pharmaceutical preparation comprising the particulate construct according to claim 8.

10. A particulate construct according to claim 1, wherein said internal phase contains an agricultural drug component.

11. An agricultural drug composition comprising the particulate construct according to claim 10.

12. A particulate construct according to claim 1, wherein said internal phase contains a gaseous phase.

13. A particulate construct according to claim 12, wherein said gaseous phase is filled with perfluorocarbon gas.

14. An ultrasonic contrast medium comprising the particulate construct according to claim 12.

15. A particulate construct according to claim 1, wherein said internal phase contains at least a dye or a pigment.

16. An ink composition comprising the particulate construct according to claim 15.

17. A particulate construct according to claim 1, wherein said internal phase contains hemoglobin.

18. A blood corpuscle composition comprising the particulate construct according to claim 17.

19. A particulate construct according to claim 1, wherein said internal phase contains a cosmetic component.

20. A cosmetic composition comprising the particulate construct according to claim 19.

21. A particulate construct according to claim 1, wherein said internal phase contains a fertilizer component.

22. A fertilizer composition comprising the particulate construct according to claim 21.

* * * * *

SEQUENCE LISTING

<160> NUMBER OF SEQ ID NOS: 14

<210> SEQ ID NO 1
<211> LENGTH: 30

<212> TYPE: DNA
<213> ORGANISM: Artificial Sequence
<220> FEATURE:
<223> OTHER INFORMATION: Primer for PCR multiplication

<400> SEQUENCE: 1
cgggatccag taacaagagt aacgatgagt                                    30

<210> SEQ ID NO 2
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 2
cgatctcgag ttaccgttcg tgcacgtacg                                    30

<210> SEQ ID NO 3
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 3
tgctggaact gatccagtac                                               20

<210> SEQ ID NO 4
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 4
gggttgagga tgctctggat gtg                                           23

<210> SEQ ID NO 5
<211> LENGTH: 1680
<212> TYPE: DNA
<213> ORGANISM: Pseudomonas cichorii YN2 ; FERM BP-7375

<400> SEQUENCE: 5
atgagtaaca agagtaacga tgagttgaag tatcaagcct ctgaaaacac              50
cttggggctt aatcctgtcg ttgggctgcg tggaaaggat ctactggctt              100
ctgctcgaat ggtgcttagg caggccatca agcaaccggt gcacagcgtc              150
aaacatgtcg cgcactttgg tcttgaactc aagaacgtac tgctgggtaa              200
atccgggctg caaccgacca gcgatgaccg tcgcttcgcc gatccggcct              250
ggagccagaa cccgctctat aaacgttatt tgcaaaccta cctggcgtgg              300
cgcaaggaac tccacgactg gatcgatgaa agtaacctcg cccccaagga              350
tgtggcgcgt gggcacttcg tgatcaacct catgaccgaa gccatggcgc              400
cgaccaacac cgcggccaac ccggcggcag tcaaacgctt tttcgaaacc              450
ggtggcaaaa gcctgctcga cggcctctcg cacctggcca aggatctggt              500
acacaacggc ggcatgccga gccaggtcaa catgggtgca ttcgaggtcg              550
gcaagagcct gggcgtgacc gaaggcgcgg tggtgtttcg caacgatgtg              600
ctggaactga tccagtacaa gccgaccacc gagcaggtat acgaacgccc              650

| | |
|---|---|
| gctgctggtg gtgccgccgc agatcaacaa gttctacgtt ttcgacctga | 700 |
| gcccggacaa gagcctggcg cggttctgcc tgcgcaacaa cgtgcaaacg | 750 |
| ttcatcgtca gctggcgaaa tcccaccaag gaacagcgag agtggggcct | 800 |
| gtcgacctac atcgaagccc tcaaggaagc ggttgatgtc gttaccgcga | 850 |
| tcaccggcag caaagacgtg aacatgctcg gcgcctgctc cggcggcatc | 900 |
| acttgcaccg cgctgctggg ccattacgcg gcgattggcg aaaacaaggt | 950 |
| caacgccctg accttgctgg tgagcgtgct tgataccacc ctcgacagcg | 1000 |
| atgttgccct gttcgtcaat gaacagaccc ttgaagccgc caagcgccac | 1050 |
| tcgtaccagg ccggcgtact ggaaggccgc gacatggcga aggtcttcgc | 1100 |
| ctggatgcgc cccaacgatc tgatctggaa ctactgggtc aacaattacc | 1150 |
| tgctaggcaa cgaaccgccg gtgttcgaca tcctgttctg gaacaacgac | 1200 |
| accacacggt tgcccgcggc gttccacggc gacctgatcg aactgttcaa | 1250 |
| aaataaccca ctgattcgcc cgaatgcact ggaagtgtgc ggcaccccca | 1300 |
| tcgacctcaa gcaggtgacg gccgacatct tttccctggc cggcaccaac | 1350 |
| gaccacatca ccccgtggaa gtcctgctac aagtcggcgc aactgtttgg | 1400 |
| cggcaacgtt gaattcgtgc tgtcgagcag cgggcatatc cagagcatcc | 1450 |
| tgaacccgcc gggcaatccg aaatcgcgct acatgaccag caccgaagtg | 1500 |
| gcggaaaatg ccgatgaatg gcaagcgaat gccaccaagc ataccgattc | 1550 |
| ctggtggctg cactggcagg cctggcaggc ccaacgctcg ggcgagctga | 1600 |
| aaaagtcccc gacaaaactg ggcagcaagg cgtatccggc aggtgaagcg | 1650 |
| gcgccaggca cgtacgtgca cgaacggtaa | 1680 |

<210> SEQ ID NO 6
<211> LENGTH: 1683
<212> TYPE: DNA
<213> ORGANISM: Pseudomonas cichorii YN2 ; FERM BP-7375

<400> SEQUENCE: 6

| | |
|---|---|
| atgcgcgata aacctgcgag ggagtcacta cccacccccg ccaagttcat | 50 |
| caacgcacaa agtgcgatta ccggcctgcg tggccgggat ctggtttcga | 100 |
| ctttgcgcag tgtcgccgcc catggcctgc gccaccccgt gcacaccgcg | 150 |
| cgacacgcct tgaaactggg tggtcaactg ggacgcgtgt tgctgggcga | 200 |
| cacccctgcat cccaccaacc cgcaagaccg tcgcttcgac gatccggcgt | 250 |
| ggagtctcaa tcccttttat cgtcgcagcc tgcaggcgta cctgagctgg | 300 |
| cagaagcagg tcaagagctg gatcgacgaa agcaacatga gcccggatga | 350 |
| ccgcgcccgt gcgcacttcg cgttcgccct gctcaacgat gccgtgtcgc | 400 |
| cgtccaacag cctgctcaat ccgctggcga tcaaggaaat cttcaactcc | 450 |
| ggcggcaaca gcctggtgcg cgggatcggc catctggtcg atgacctctt | 500 |
| gcacaacgat ggcttgcccc ggcaagtcac caggcatgca ttcgaggttg | 550 |
| gcaagaccgt cgccaccacc accggcgccg tggtgtttcg caacgagctg | 600 |
| ctggagctga tccaatacaa gccgatgagc gaaaagcagt attccaaacc | 650 |
| gctgctggtg gtgccgccac agatcaacaa gtactacatt tttgacctca | 700 |
| gcccccataa cagcttcgtc cagttcgcgc tcaagaacgg cctgcaaacc | 750 |

-continued

| | |
|---|---|
| ttcgtcatca gctggcgcaa tccggatgta cgtcaccgcg aatggggcct | 800 |
| gtcgacctac gtcgaagcgg tggaagaagc catgaatgtc tgccgggcaa | 850 |
| tcaccggcgc gcgcgaggtc aacctgatgg gcgcctgcgc tggcgggctg | 900 |
| accattgctg ccctgcaggg ccacttgcaa gccaagcgac agctgcgccg | 950 |
| cgtctccagc gcgacgtacc tggtgagcct gctcgacagc caactggaca | 1000 |
| gcccggccac actcttcgcc gacgaacaga ccctggaggc ggccaagcgc | 1050 |
| cgctcctacc agaaaggtgt gctggaaggc cgcgacatgg ccaaggtttt | 1100 |
| cgcctggatg cgccccaacg atttgatctg gagctacttc gtcaacaatt | 1150 |
| acctgatggg caaggagccg ccggcgttcg acattctcta ctggaacaat | 1200 |
| gacaacacac gcctgccggc cgccctgcat ggtgacttgc tggacttctt | 1250 |
| caagcacaac ccgctgagcc atccgggtgg cctggaagtg tgcggcaccc | 1300 |
| cgatcgactt gcaaaaggtc accgtcgaca gtttcagcgt ggccggcatc | 1350 |
| aacgatcaca tcacgccgtg ggacgcggtg tatcgctcaa ccctgttgct | 1400 |
| cggtggcgag cgtcgctttg tcctggccaa cagcggtcat gtgcagagca | 1450 |
| ttctcaaccc gccgaacaat ccgaaagcca actacctcga aggtgcaaaa | 1500 |
| ctaagcagcg accccagggc ctggtactac gacgccaagc ccgtcgacgg | 1550 |
| tagctggtgg acgcaatggc tgggctggat tcaggagcgc tcgggcgcgc | 1600 |
| aaaaagaaac ccacatggcc ctcggcaatc agaattatcc accgatggag | 1650 |
| gcggcgcccg ggacttacgt gcgcgtgcgc tga | 1683 |

<210> SEQ ID NO 7
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 7
ggaccaagct tctcgtctca gggcaatgg                                       29

<210> SEQ ID NO 8
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 8
cgagcaagct tgctcctaca ggtgaaggc                                       29

<210> SEQ ID NO 9
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 9
gtattaagct tgaagacgaa ggagtgttg                                       29

<210> SEQ ID NO 10
<211> LENGTH: 30
<212> TYPE: DNA

```
<213> ORGANISM: Artificial Sequence
<220> FEATURE:
<223> OTHER INFORMATION: Primer for PCR multiplication

<400> SEQUENCE: 10
catccaagct tcttatgatc gggtcatgcc                                    30

<210> SEQ ID NO 11
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 11
cgggatccag taacaagagt aacgatgagt                                    30

<210> SEQ ID NO 12
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 12
cgatctcgag ttaccgttcg tgcacgtacg                                    30

<210> SEQ ID NO 13
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 13
cgggatcccg cgataaacct gcgagggagt                                    30

<210> SEQ ID NO 14
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 14
cgatctcgag gcgcacgcgc acgtaagtcc                                    30
```